US006763836B2

(12) United States Patent
Tasto et al.

(10) Patent No.: US 6,763,836 B2
(45) Date of Patent: Jul. 20, 2004

(54) METHODS FOR ELECTROSURGICAL TENDON VASCULARIZATION

(75) Inventors: James P. Tasto, San Diego, CA (US); Jean Woloszko, Mountain View, CA (US); Michael A. Baker, Woodside, CA (US); James L. Pacek, Coto De Caza, CA (US); Philip E. Eggers, Dublin, OH (US); Hira V. Thapliyal, Los Altos, CA (US)

(73) Assignee: Arthrocare Corporation, Sunnyvale, CA (US)

( * ) Notice: Subject to any disclaimer, the term of this patent is extended or adjusted under 35 U.S.C. 154(b) by 0 days.

(21) Appl. No.: 10/174,266

(22) Filed: Jun. 18, 2002

(65) Prior Publication Data

US 2003/0055418 A1 Mar. 20, 2003

Related U.S. Application Data

(60) Continuation-in-part of application No. 09/845,034, filed on Apr. 27, 2001, which is a continuation-in-part of application No. 09/570,394, filed on May 12, 2000, now Pat. No. 6,595,990, which is a division of application No. 09/089,012, filed on Jun. 2, 1998, now Pat. No. 6,102,046.
(60) Provisional application No. 60/375,735, filed on Apr. 25, 2002, and provisional application No. 60/200,712, filed on Apr. 27, 2000.

(51) Int. Cl.[7] ................................................. A61N 5/00
(52) U.S. Cl. ........................................ 128/898; 606/41
(58) Field of Search ............................... 606/41, 42, 45, 606/48; 607/101, 102, 104, 105; 604/22, 114; 128/898

(56) References Cited

U.S. PATENT DOCUMENTS 2,056,377 A 10/1936 Wappler 3,828,780 A 8/1974 Morrison, Jr. et al.
3,901,242 A 8/1975 Storz
3,939,839 A 2/1976 Curtiss
3,970,088 A 7/1976 Morrison (List continued on next page.)

FOREIGN PATENT DOCUMENTS

| DE | 3930451 | 3/1991 | ........... A61B/17/39 |
| --- | --- | --- | --- |
| EP | 0650701 | 5/1995 | ........... A61B/17/39 |
| EP | 0 703 461 | 3/1996 | ........... G01R/27/02 |
| EP | 0 740 926 A2 | 11/1996 | ........... A61B/17/39 |
| EP | 0 754 437 | 1/1997 | ........... A61B/17/39 |

(List continued on next page.)

OTHER PUBLICATIONS

Pearce, John A. (1986) *Electrosurgery*, pp. 17, 69–75, 87, John Wiley & Sons, New York.

J.W. Ramsey et al. *Urological Research* vol. 13, pp. 99–102 (1985).

V.E. Elsasser et al. *Acta Medicotechnica* vol. 24, No. 4, pp. 129–134 (1976).

(List continued on next page.)

*Primary Examiner*—Michael Peffley
(74) *Attorney, Agent, or Firm*—John T. Raffle; Richard R. Batt

(57) ABSTRACT

Systems, apparatus, and methods are provided for promoting blood flow to a target tissue. In one variation, the invention involves creating a pattern of voids in connective tissue, or through a tissue having sparse vascularity, such as a tendon or a meniscus, in order to increase blood flow within the tissue. This also includes using a template device to assist in the creation of the pattern of voids. Also included is an electrosurgical device with a self-contained fluid supply for providing conductive fluid to the target tissue or to active electrodes of the device.

24 Claims, 32 Drawing Sheets

U.S. PATENT DOCUMENTS

| | | |
|---|---|---|
| 4,040,426 A | 8/1977 | Morrison, Jr. |
| 4,043,342 A | 8/1977 | Morrison, Jr. |
| 4,074,718 A | 2/1978 | Morrison, Jr. |
| 4,092,986 A | 6/1978 | Schneiderman |
| 4,116,198 A | 9/1978 | Roos |
| 4,181,131 A | 1/1980 | Ogiu |
| 4,184,492 A | 1/1980 | Meinke et al. |
| 4,202,337 A | 5/1980 | Hren et al. |
| 4,228,800 A | 10/1980 | Degler, Jr. et al. |
| 4,232,676 A | 11/1980 | Herczog |
| 4,248,231 A | 2/1981 | Herczog et al. |
| 4,326,529 A | 4/1982 | Doss et al. |
| 4,381,007 A | 4/1983 | Doss |
| 4,476,862 A | 10/1984 | Pao |
| 4,483,338 A | 11/1984 | Bloom et al. |
| 4,532,924 A | 8/1985 | Auth et al. |
| 4,548,207 A | 10/1985 | Reimels |
| 4,567,890 A | 2/1986 | Ohta et al. |
| 4,582,057 A | 4/1986 | Auth et al. |
| 4,593,691 A | 6/1986 | Lindstrom et al. |
| 4,660,571 A | 4/1987 | Hess et al. |
| 4,674,499 A | 6/1987 | Pao |
| 4,682,596 A | 7/1987 | Bales et al. |
| 4,706,667 A | 11/1987 | Roos |
| 4,727,874 A | 3/1988 | Bowers et al. |
| 4,765,331 A | 8/1988 | Petruzzi et al. |
| 4,805,616 A | 2/1989 | Pao |
| 4,823,791 A | 4/1989 | D'Amelio et al. |
| 4,832,048 A | 5/1989 | Cohen |
| 4,920,978 A | 5/1990 | Colvin |
| 4,931,047 A | 6/1990 | Broadwin et al. |
| 4,936,281 A | 6/1990 | Stasz |
| 4,936,301 A | 6/1990 | Rexroth et al. |
| 4,943,290 A | 7/1990 | Rexroth et al. |
| 4,966,597 A | 10/1990 | Cosman |
| 4,967,765 A | 11/1990 | Turner et al. |
| 4,976,711 A | 12/1990 | Parins et al. |
| 4,979,948 A | 12/1990 | Geddes et al. |
| 4,998,933 A | 3/1991 | Eggers et al. |
| 5,007,908 A | 4/1991 | Rydell |
| 5,009,656 A | 4/1991 | Reimels |
| 5,035,696 A | 7/1991 | Rydell |
| 5,037,421 A | 8/1991 | Boutacoff et al. |
| 5,047,026 A | 9/1991 | Rydell |
| 5,047,027 A | 9/1991 | Rydell |
| 5,078,717 A | 1/1992 | Parins et al. |
| 5,080,660 A | 1/1992 | Buelna |
| 5,084,044 A | 1/1992 | Quint |
| 5,085,659 A | 2/1992 | Rydell |
| 5,088,997 A | 2/1992 | Delahuerga et al. |
| 5,098,431 A | 3/1992 | Rydell |
| 5,099,840 A | 3/1992 | Goble |
| 5,102,410 A | 4/1992 | Dressel |
| 5,108,391 A | 4/1992 | Flachenecker et al. |
| 5,112,330 A | 5/1992 | Nishigaki et al. |
| 5,122,138 A | 6/1992 | Manwaring |
| 5,125,928 A | 6/1992 | Parins et al. |
| 5,147,354 A | 9/1992 | Boutacoff et al. |
| 5,167,659 A | 12/1992 | Ohtomo et al. |
| 5,171,311 A | 12/1992 | Rydell et al. |
| 5,176,528 A | 1/1993 | Fry et al. |
| 5,178,620 A | 1/1993 | Eggers et al. |
| 5,190,517 A | 3/1993 | Zieve et al. |
| 5,192,280 A | 3/1993 | Parins |
| 5,195,959 A | 3/1993 | Smith |
| 5,197,466 A | 3/1993 | Marchosky et al. |
| 5,197,963 A | 3/1993 | Parins |
| 5,207,675 A | 5/1993 | Canady |
| 5,217,457 A | 6/1993 | Delahuerga et al. |
| 5,217,459 A | 6/1993 | Kamerling |
| 5,230,334 A | 7/1993 | Klopotek |
| 5,267,994 A | 12/1993 | Gentelia et al. |
| 5,267,997 A | 12/1993 | Farin et al. |
| 5,273,524 A | 12/1993 | Fox et al. |
| 5,277,201 A | 1/1994 | Stern |
| 5,282,799 A | 2/1994 | Rydell |
| 5,290,282 A | 3/1994 | Casscells |
| 5,300,069 A | 4/1994 | Hunsberger et al. |
| 5,304,169 A | 4/1994 | Sand |
| 5,306,238 A | 4/1994 | Fleenor |
| 5,312,400 A | 5/1994 | Bales et al. |
| 5,314,406 A | 5/1994 | Arias et al. |
| 5,324,254 A | 6/1994 | Phillips |
| 5,330,470 A | 7/1994 | Hagen |
| 5,334,140 A | 8/1994 | Phillips |
| 5,342,357 A | 8/1994 | Nardella |
| 5,366,443 A | 11/1994 | Eggers et al. |
| 5,370,675 A | 12/1994 | Edwards et al. |
| 5,374,265 A | 12/1994 | Sand |
| 5,375,588 A | 12/1994 | Yoon |
| 5,380,277 A | 1/1995 | Phillips |
| 5,383,876 A | 1/1995 | Nardella |
| 5,383,917 A | 1/1995 | Desai et al. |
| 5,395,312 A | 3/1995 | Desai |
| 5,395,363 A | 3/1995 | Billings et al. |
| 5,417,687 A | 5/1995 | Nardella et al. |
| 5,419,767 A | 5/1995 | Eggers et al. |
| 5,423,810 A | 6/1995 | Goble et al. |
| 5,423,882 A | 6/1995 | Jackman et al. |
| 5,433,708 A | 7/1995 | Nichols et al. |
| 5,436,566 A | 7/1995 | Thompson et al. |
| 5,438,302 A | 8/1995 | Goble |
| 5,441,499 A | 8/1995 | Fritzsch |
| 5,451,224 A | 9/1995 | Goble et al. |
| 5,454,809 A | 10/1995 | Janssen |
| 5,458,596 A | 10/1995 | Lax et al. |
| 5,462,545 A | 10/1995 | Wang et al. |
| 5,496,312 A | 3/1996 | Klicek |
| 5,496,314 A | 3/1996 | Eggers |
| 5,496,317 A | 3/1996 | Goble et al. |
| 5,514,130 A | 5/1996 | Baker |
| 5,542,928 A | 8/1996 | Evans et al. |
| 5,556,397 A | 9/1996 | Long et al. |
| 5,562,703 A | 10/1996 | Desai |
| 5,569,242 A | 10/1996 | Lax et al. |
| 5,571,100 A | 11/1996 | Goble et al. |
| 5,584,872 A | 12/1996 | LaFontaine et al. |
| 5,609,151 A | 3/1997 | Mulier et al. |
| 5,626,576 A | 5/1997 | Janssen |
| 5,633,578 A | 5/1997 | Eggers et al. |
| 5,647,869 A | 7/1997 | Goble et al. |
| 5,662,680 A | 9/1997 | Desai |
| 5,676,693 A | 10/1997 | LaFontaine et al. |
| 5,681,282 A | 10/1997 | Eggers et al. |
| 5,683,366 A | 11/1997 | Eggers et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,725,524 A | 3/1998 | Mulier et al. |
| 5,766,153 A | 6/1998 | Eggers et al. |
| 5,785,705 A | 7/1998 | Baker |
| 5,807,395 A | 9/1998 | Mulier et al. |
| 5,810,764 A | 9/1998 | Eggers et al. |
| 5,810,809 A | 9/1998 | Rydell |
| 5,843,019 A | 12/1998 | Eggers et al. |
| 5,860,974 A | 1/1999 | Abele |
| 5,860,975 A | 1/1999 | Goble et al. |
| 5,871,469 A | 2/1999 | Eggers et al. |
| 5,871,524 A | 2/1999 | Knowlton |

| | | |
|---|---|---|
| 5,873,855 A | 2/1999 | Eggers et al. |
| 5,885,277 A | 3/1999 | Korth |
| 5,888,198 A | 3/1999 | Eggers et al. |
| 5,891,095 A | 4/1999 | Eggers et al. |
| 5,893,848 A | 4/1999 | Negus |
| 5,895,386 A | 4/1999 | Odell et al. |
| 5,897,553 A | 4/1999 | Mulier |
| 5,902,272 A | 5/1999 | Eggers et al. |
| 5,904,681 A | 5/1999 | West, Jr. |
| 5,944,715 A | 8/1999 | Goble et al. |
| 5,976,127 A | 11/1999 | Lax |
| 6,004,319 A | 12/1999 | Goble et al. |
| 6,013,076 A | 1/2000 | Goble et al. |
| 6,015,406 A | 1/2000 | Goble et al. |
| 6,024,733 A | 2/2000 | Eggers et al. |
| 6,027,501 A | 2/2000 | Goble et al. |
| 6,039,734 A | 3/2000 | Goble et al. |
| 6,045,532 A | 4/2000 | Eggers et al. |
| 6,056,746 A | 5/2000 | Goble et al. |
| 6,063,079 A | 5/2000 | Hovda et al. |
| 6,066,134 A | 5/2000 | Eggers et al. |
| 6,068,628 A | 5/2000 | Fanton et al. |
| 6,102,046 A * | 8/2000 | Weinstein et al. .......... 128/898 |
| 6,109,268 A | 8/2000 | Thapliyal et al. |
| 6,117,109 A | 9/2000 | Eggers et al. |
| 6,126,682 A | 10/2000 | Sharkey et al. |
| 6,142,992 A | 11/2000 | Cheng et al. |
| 6,149,620 A | 11/2000 | Baker et al. |
| 6,156,031 A | 12/2000 | Aita et al. |
| 6,159,194 A | 12/2000 | Eggers et al. |
| 6,159,208 A | 12/2000 | Hovda et al. |
| 6,168,593 B1 | 1/2001 | Sharkey et al. |
| 6,179,824 B1 | 1/2001 | Eggers et al. |
| 6,179,836 B1 | 1/2001 | Eggers et al. |
| 6,183,469 B1 | 2/2001 | Thapliyal et al. |
| 6,190,381 B1 | 2/2001 | Olsen et al. |
| 6,203,542 B1 | 3/2001 | Ellsberry et al. |
| 6,210,402 B1 | 4/2001 | Olsen et al. |
| 6,210,405 B1 | 4/2001 | Goble et al. |
| 6,224,592 B1 | 5/2001 | Eggers et al. |
| 6,234,178 B1 | 5/2001 | Goble et al. |
| 6,235,020 B1 | 5/2001 | Cheng et al. |
| 6,238,391 B1 | 5/2001 | Olsen et al. |
| 6,254,600 B1 | 7/2001 | Willink et al. |
| 6,264,652 B1 | 7/2001 | Eggers et al. |
| 6,267,757 B1 | 7/2001 | Aita et al. |
| 6,277,112 B1 | 8/2001 | Underwood et al. |
| 6,283,961 B1 | 9/2001 | Underwood et al. |
| 6,296,636 B1 | 10/2001 | Cheng et al. |
| 6,296,638 B1 | 10/2001 | Davison et al. |
| 6,312,408 B1 | 11/2001 | Eggers et al. |
| 6,315,774 B1 | 11/2001 | Daniel et al. |
| 6,322,549 B1 | 11/2001 | Eggers et al. |
| 6,355,006 B1 * | 3/2002 | Ryaby et al. .................. 601/2 |
| 6,355,032 B1 | 3/2002 | Hovda et al. |
| 6,363,937 B1 | 4/2002 | Hovda et al. |
| 6,379,350 B1 | 4/2002 | Sharkey et al. |
| 6,379,351 B1 | 4/2002 | Thapliyal et al. |
| 6,391,025 B1 | 5/2002 | Weinstein et al. |
| 6,391,028 B1 | 5/2002 | Fanton et al. |
| 6,416,507 B1 | 7/2002 | Eggers et al. |
| 6,416,508 B1 | 7/2002 | Eggers et al. |
| 6,432,103 B1 | 8/2002 | Ellsberry et al. |
| 6,468,274 B1 | 10/2002 | Alleyne et al. |
| 6,514,250 B1 | 2/2003 | Jahns et al. |
| 6,530,922 B2 | 3/2003 | Cosman |
| 6,557,559 B1 | 5/2003 | Eggers et al. |
| 6,595,990 B1 * | 7/2003 | Weinstein et al. ............. 606/41 |
| 6,602,248 B1 | 8/2003 | Sharps et al. |
| 2002/0026186 A1 | 2/2002 | Woloszko et al. |
| 2002/0029036 A1 | 3/2002 | Goble et al. |
| 2002/0049438 A1 | 4/2002 | Sharkey et al. |
| 2002/0068930 A1 * | 6/2002 | Tasto et al. .................... 606/32 |
| 2003/0171743 A1 * | 9/2003 | Tasto et al. .................... 606/32 |

FOREIGN PATENT DOCUMENTS

| | | | |
|---|---|---|---|
| EP | 0650701 | 3/1999 | ........... A61B/17/39 |
| EP | 0774926 | 6/1999 | ........... A61B/17/39 |
| EP | 923907 | 6/1999 | ........... A61B/17/39 |
| EP | 0923907 | 6/1999 | ........... A61B/17/39 |
| EP | 0 694 290 | 11/2000 | ........... A61B/18/04 |
| EP | 1149564 | 10/2001 | ........... A61B/18/14 |
| FR | 2313949 | 1/1977 | ........... A61N/3/02 |
| GB | 2 308 979 | 7/1997 | ........... A61B/17/36 |
| GB | 2 308 980 | 7/1997 | ........... A61B/17/36 |
| GB | 2 308 981 | 7/1997 | ........... A61B/17/36 |
| GB | 2 327 350 | 1/1999 | ........... A61B/17/39 |
| GB | 2 327 351 | 1/1999 | ........... A61B/17/39 |
| GB | 2 327 352 | 1/1999 | ........... A61B/17/39 |
| GB | 2379878 | 3/2003 | ........... A61B/18/04 |
| JP | 57-57802 | 4/1982 | ........... A61B/1/00 |
| JP | 57-117843 | 7/1982 | ........... A61B/17/39 |
| WO | 90/03152 | 4/1990 | ........... A61B/17/39 |
| WO | WO 90/07303 | 7/1990 | ........... A61B/17/39 |
| WO | 92/21278 | 12/1992 | ........... A61B/5/04 |
| WO | WO 93/13816 | 7/1993 | ........... A61B/17/36 |
| WO | 93/20747 | 10/1993 | ........... A61B/5/00 |
| WO | WO 94/04220 | 3/1994 | ........... A61N/1/06 |
| WO | 94/08654 | 4/1994 | ........... A61M/37/00 |
| WO | 94/26228 | 11/1994 | ........... A61G/17/36 |
| WO | 95/05781 | 3/1995 | ........... A61B/17/39 |
| WO | 95/05867 | 3/1995 | ........... A61N/1/05 |
| WO | 95/30373 | 11/1995 | ........... A61B/17/00 |
| WO | WO 95/34259 | 12/1995 | ........... A61F/5/48 |
| WO | 96/00042 | 1/1996 | ........... A61B/17/39 |
| WO | 96/07360 | 3/1996 | ........... A61B/17/39 |
| WO | 96/34568 | 11/1996 | ........... A61B/17/36 |
| WO | 97/00646 | 1/1997 | ........... A61B/17/39 |
| WO | 97/00647 | 1/1997 | ........... A61B/17/39 |
| WO | 97/15238 | 5/1997 | ........... A61B/17/39 |
| WO | 97/24073 | 7/1997 | ........... A61B/17/39 |
| WO | WO 97/24074 | 7/1997 | ........... A61B/17/39 |
| WO | 97/24992 | 7/1997 | ........... A61B/17/38 |
| WO | 97/24993 | 7/1997 | ........... A61B/17/39 |
| WO | 97/24994 | 7/1997 | ........... A61B/17/39 |
| WO | 97/41786 | 11/1997 | ........... A61B/17/39 |
| WO | 97/48345 | 12/1997 | ........... A61B/17/39 |
| WO | 97/48346 | 12/1997 | ........... A61B/17/39 |
| WO | 98/07468 | 2/1998 | ........... A61N/1/40 |
| WO | 98/14131 | 4/1998 | ........... A61B/18/14 |
| WO | 98/27879 | 7/1998 | ........... A61B/17/36 |
| WO | 98/27880 | 7/1998 | ........... A61B/17/39 |
| WO | 99/51155 | 10/1999 | ........... A61B/17/36 |
| WO | 99/51158 | 10/1999 | ........... A61B/17/39 |
| WO | 03/024339 | 3/2003 | ........... A61B/17/32 |

OTHER PUBLICATIONS

P.C. Nardella (1989) *SPIE* 1068:42–49 Radio Frequency Energy and Impedance Feedback.

R. Tucker et al., Abstract P14–11, p. 248, "A Bipolar Electrosurgical Turp Loop".

R. Tucker et al. *J. of Urology* vol. 141, pp. 662–665, (1989).

R. Tucker et al. *Urological Research* vol. 18, pp. 291–294 (1990).

Kramolowsky et al. *J. of Urology* vol. 143, pp. 275–277 (1990).

Kramolowsky et al. *J. of Urology* vol. 146, pp. 669–674 (1991).

Slager et al. *Z. Kardiol.* 76:Suppl. 6, 67–71 (1987).

Slager et al. *JACC* 5(6):1382–6 (1985).

Olsen MD, Bipolar Laparscopic Cholecstectomy Lecture (marked confidential), Oct. 7, 1991.

Codman & Shurtleff, Inc. "The Malis Bipolar Electrosurgical System CMC–III Instruction Manual" Jul. 1991.

Valley Forge's New Products, Clinica, 475, 5, Nov. 6, 1991.

Valley Forge Scientific Corp., "Summary of Safety and Effective Information from 510K," 1991.

Codman & Shurtleff, Inc. "The Malis Bipolar Coagulating and Bipolar Cutting System CMC–II" brochure, early 1991.

L. Malis, "The Value of Irrigation During Bipolar Coagulation" See ARTC 21602, early Apr. 9, 1993.

L. Malis, "Excerpted from a seminar by Leonard I. Malis, M.D. at the 1995 American Association of Neurological Surgeons Meeting," 1995.

L. Malis, "Electrosurgery, Technical Note," *J. Neursurg.*, vol. 85, 970–975, Nov. 1996.

Ian E. Shuman, "Bipolar Versus Monopolar Electrosurgery: Clinical Applications," *Dentistry Today*, vol. 20, No. 12, Dec. 2001.

Protell et al., "Computer–Assisted Electrocoagulation: Bipolar v. Monopolar in the Treatment of Experimental Canine Gastric Ulcer Bleeding," *Gastroenterology* vol. 80, No. 3, pp. 451–455.

Cook and Webster, "Therapeutic Medical Devices: Application and Design," 1982.

Valleylab SSE2L Instruction Manual, Jan. 6, 1983.

Robert D. Tucker et al., "Demodulated Low Frequency Currents from Electrosurgical Procedures," *Surgery, Gynecology and Obstetrics*, 159:39–43, 1984.

Lu, et al., "Electrical Thermal Angioplasty: Catheter Design Features, In Vitro Tissue Ablation Studies and In Vitro Experimental Findings," *Am J. Cardiol* vol. 60, pp. 1117–1122.

Selikowitz & LaCourse, "Electric Current and Voltage Recordings on the Myocardium During Electrosurgical Procedures in Canines," *Surgery, Gynecology & Obstetrics*, vol. 164, 219–224, Mar. 1987.

J. O'Malley, Schaum's Outline of Theory and Problems of Basic Circuit Analysis, McGraw–Hill, $2^{nd}$ Ed., 1992, pp. 3–5.

Arnaud Wattiez et al., "Electrosurgery in Operative Endoscopy," Electrosurgical Effects, Blackwell Science, pp. 85–93, 1995.

Leslie A. Geddes, "Medical Device Accidents: With Illustrative Cases" CRC Press, 1998.

Wyeth, "Electrosurgical Unit" pp. 1181–1202.

C.P. Swain, et al., *Gut* vol. 25, pp. 1424–1431 (1984).

Piercey et al., *Gastroenterology* vol. 74 (3) , pp. 527–534 (1978).

A.K. Dobbie *Bio–Medical Engineering* vol. 4, pp. 206–216 (1969).

B. Lee et al. JACC vol. 13(5) , pp. 1167–1175 (1989).

K. Barry et al. *American Heart Journal* vol. 117, pp. 332–341 (1982).

W. Honig *IEEE* pp. 58–65 (1975).

Jacob Kline, *Handbook of Biomedical Engineering*, Academic Press Inc. , N.Y., pp. 98–113, 1988.

M.B. Dennis et al. "Evolution of Electrofulguration in Control of Bleeding of Experimental Gastric Ulcers," Digestive Diseases and Sciences, vol. 24, No. 11, 845–848.

Letter from Department of Health to Jerry Malis dated Apr. 15, 1985.

Letter from Jerry Malis to FDA dated Jul. 25, 1985.

Letter from Department of Health to Jerry Malis dated Apr. 22, 1991.

Leonard Malis, "Instrumenation for Microvascular Neurosurgery" *Cerebrovascular Surgery*, vol. 1, 245–260, 1985.

\* cited by examiner

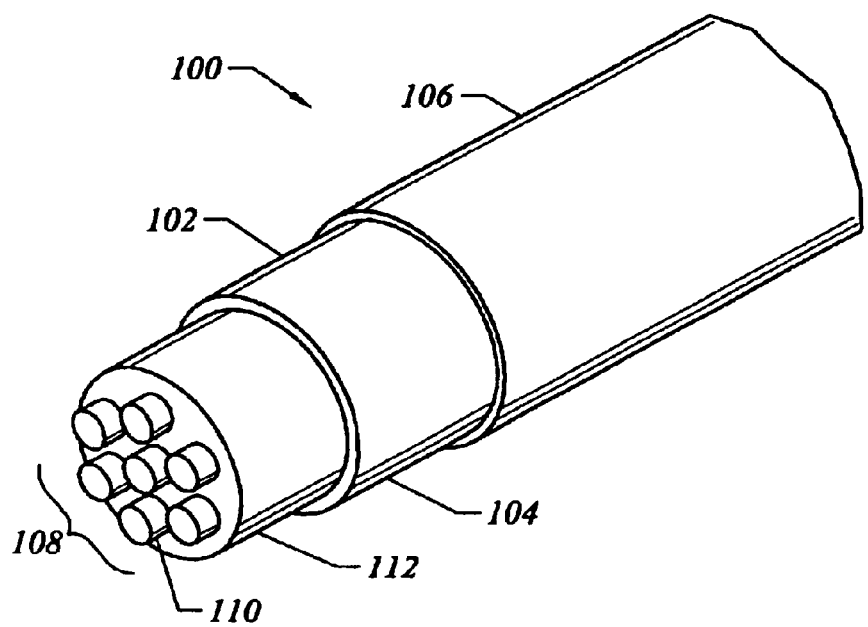
FIG. 3
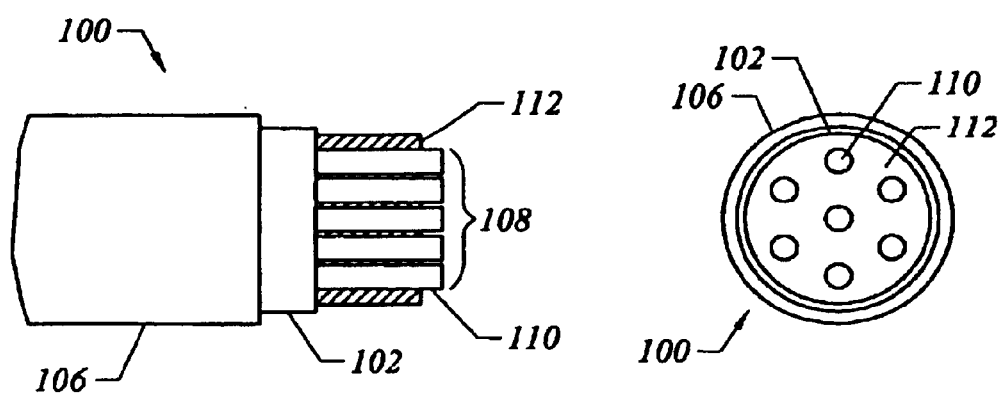
FIG. 4A  FIG. 4B

METHODS FOR ELECTROSURGICAL TENDON VASCULARIZATION

CROSS-REFERENCE TO RELATED APPLICATIONS

The present invention is a non-provisional of U.S. Provisional Application No. 60/375,735 filed Apr. 25, 2002. This application is also a continuation-in-part of U.S. patent application Ser. No. 09/845,034, filed Apr. 27, 2001, which is a non-provisional of U.S. Provisional Application No. 60/200,712, filed Apr. 27, 2000, and which is a continuation-in-part of U.S. patent application Ser. No. 09/570,394, filed May 12, 2000, now U.S. Pat. No. 6,595,990 which is a divisional of U.S. patent application Ser. No. 09/089,012, filed Jun. 2, 1998 now U.S. Pat. No. 6,102,046, the complete disclosures of all of which are incorporated herein by reference for all purposes.

The present invention is related to commonly assigned U.S. patent application Ser. No. 08/990,374, filed Dec. 15, 1997 now U.S. Pat. No. 6,109,268, which is a continuation-in-part of U.S. patent application Ser. No. 08/485,219, filed on Jun. 7, 1995, now U.S. Pat. No. 5,697,281, U.S. patent application Ser. Nos. 09/058,571, 08/874,173 and 09/002,315, filed on Apr. 10, 1998, Jun. 13, 1997, and Jan. 2, 1998, respectively and now U.S. Pat. Nos. 6,142,992; 6,179,824; 6,183,469 respectively, and U.S. patent application Ser. No. 09/054,323, filed on Apr. 2, 1998 now U.S. Pat. No. 6,063,079, U.S. patent application Ser. No. 09/010,382, filed Jan. 21, 1998 now U.S. Pat. No. 6,190,381, and U.S. patent application Ser. No. 09/032,375, filed Feb. 27, 1998 now U.S. Pat. No. 6,355,032, U.S. patent application Ser. No. 08/977,845, filed on Nov. 25, 1997 now U.S. Pat. No. 6,210,402, Ser. No. 08/942,580, filed on Oct. 2, 1997 now U.S. Pat. No. 6,159,194, Ser. No. 09/026,851, filed Feb. 20, 1998 now U.S. Pat. No. 6,277,112, U.S. patent application Ser. No. 08/753,227, filed on Nov. 22, 1996 now U.S. Pat. No. 5,873,855, U.S. patent application Ser. No. 08/687,792, filed on Jul. 18, 1996 now U.S. Pat. No. 5,843,019, and PCT International Application, U.S. National Phase Serial No. PCT/US94/05168, filed on May 10, 1994, now U.S. Pat. No. 5,697,909, which was a continuation-in-part of U.S. patent application Ser. No. 08/059,681, filed on May 10, 1993 now abandoned, which was a continuation-in-part of U.S. patent application Ser. No. 07/958,977, filed on Oct. 9, 1992, now U.S. Pat. No. 5,366,443, which was a continuation-in-part of U.S. patent application Ser. No. 07/817,575, filed on Jan. 7, 1992, now abandoned, the complete disclosures of which are incorporated herein by reference for all purposes.

BACKGROUND OF THE INVENTION

The present invention relates generally to the field of electrosurgery and, more particularly, to surgical devices and methods that employ high frequency electrical energy to increase the flow of blood to a target tissue.

Coronary artery disease, the build up of atherosclerotic plaque on the inner walls of the coronary arteries, causes the narrowing or complete closure of these arteries resulting in insufficient blood flow to the heart. A number of approaches have been developed for treating coronary artery disease. In less severe cases, it is often sufficient to treat the symptoms with pharmaceuticals and lifestyle modification to lessen the underlying causes of the disease. In more severe cases a coronary artery blockage can often be treated using endovascular techniques, such as balloon angioplasty, laser recanalization, placement of stents, and the like.

In cases where pharmaceutical treatment and endovascular approaches have failed or are likely to fail, it is often necessary to perform a coronary artery bypass graft (CABG) procedure using open or thoracoscopic surgical methods. For example, many patients still require bypass surgery due to such conditions as the presence of extremely diffuse stenotic lesions, the presence of total occlusions and the presence of stenotic lesions in extremely tortuous vessels. However, some patients are too sick to successfully undergo bypass surgery. For other patients, previous endovascular and/or bypass surgery attempts have failed to provide adequate revascularization of the heart muscle.

Laser myocardial revascularization (LMR) is a recent procedure developed with the recognition that myocardial circulation occurs through arterioluminal channels and myocardial sinusoids in the heart wall, as well as through the coronary arteries. In LMR procedures, artificial channels are formed in the myocardium with laser energy to provide blood flow to ischemic heart muscles by utilizing the heart's ability to perfuse itself from these artificial channels through the arterioluminal channels and myocardial sinusoids. In one such procedure, a $CO_2$ laser is utilized to vaporize tissue and produce channels in the heart wall from the epicardium through the endocardium to promote direct communication between blood within the ventricular cavity and that of existing myocardial vasculature. The laser energy is typically transmitted from the laser to the epicardium by an articulated arm device. Recently, a percutaneous method of LMR has been developed in which an elongated flexible laser apparatus is attached to a catheter and guided endoluminally into the patient's heart. The inner wall of the heart is irradiated with laser energy to form a channel from the endocardium into the myocardium for a desired distance.

While recent techniques in LMR have been promising, they also suffer from a number of drawbacks inherent with laser technology. One such drawback is that the laser energy must be sufficiently concentrated to form channels through the heart tissue, which reduces the diameter of the channels formed by LMR. In addition, free beam lasers generally must completely form each artificial lumen or revascularizing channel during the still or quiescent period of the heart beat. Otherwise, the laser beam will damage surrounding portions of the heart as the heart beats and thus moves relative to the laser beam. Consequently, the surgeon must typically form the channel in less than about 0.08 seconds, which requires a relatively large amount of energy. This further reduces the size of the channels that may be formed with a given amount of laser energy. Applicant has found that the diameter or minimum lateral dimension of these artificial channels may have an effect on their ability to remain open. Thus, the relatively small diameter channels formed by existing LMR procedures (typically on the order of about 1 mm or less) may begin to close after a brief period of time, which reduces the blood flow to the heart tissue.

Another drawback with current LMR techniques is that it is difficult to precisely control the location and depth of the channels formed by lasers. For example, the speed in which the revascularizing channels are formed often makes it difficult to determine when a given channel has pierced the opposite side of the heart wall. In addition, the distance to which the laser beam extends into the heart tissue is difficult to control, which can lead to laser irradiation with heating or vaporization of blood or heart tissue within the ventricular cavity. For example, when using the LMR technique in a pericardial approach (i.e., from the outside surface of the heart to the inside surface), the laser beam may not only pierce through the entire wall of the heart but may also irradiate blood within the heart cavity. As a result, one or more blood thromboses or clots may be formed which can lead to vascular blockages elsewhere in the circulatory system. Alternatively, when using the LMR technique in an endocardial approach (i.e., from the inside surface of the heart toward the outside surface), the laser beam may not only pierce the entire wall of the heart but may also irradiate and damage tissue surrounding the outer boundary of the heart.

The promotion of blood flow to tissue, e.g., via canalization, vascularization or revascularization, is desirable in areas of the body other than the heart. The degenerative changes in the musculoskeletal system can be attributed to aging, trauma, overuse, and diminished focal blood supply. Degenerative changes of the musculoskeletal system are ubiquitous, particularly in the shoulder, knee, elbow, or the like. Conditions such as rotator cuff tendinitis, patellar tendinitis, tennis elbow, and plantar fasciitis are extremely common, and yet have no well-defined minimally invasive treatment protocol. Typically, the treatment consists of physical therapy, non-steroidal anti-inflammatories, and occasionally surgery. Recently in Europe, surgeons have begun using lithotrypsy, receiving only equivocal results.

One example of an area of the body that would benefit from vascularization is the meniscus tissue. The meniscus tissue, a C-shaped piece of fibrocartilage located at the peripheral aspect of the joint, typically has very little blood supply (particularly the inner portions of the meniscus). For that reason, when damaged, the meniscus is unable to undergo the normal healing process that occurs in most other tissues of the body. In addition, with age, the meniscus begins to deteriorate, often developing degenerative tears. Typically, when the meniscus is damaged, the torn pieces begins to move in an abnormal fashion inside the joint. Because the space between the bones of the joint is very small, as the abnormally mobile piece of meniscal tissue (meniscal fragment) moves, it may become caught between the bones of the joint (femur and tibia). When this happens, the knee becomes painful, swollen and difficult to move.

Another example of an area of the body that would benefit from vascularization is the tendons. When a tendon is damaged, the tendon usually forms tiny tears which allow collagen to leak from the injured areas. The collagen leakage causes inflammation of the tendon that can cut off the flow of blood and pinch the surrounding nerves. Because tendons are inherently poorly vascularized, and receive less oxygen, nutrients, and blood flow, as compared with other tissues and organs, tendons tend to heal much more slowly than other tissues of the body. Accordingly, there is a need for apparatus and methods to canalize, vascularize, revascularize, and/or increase blood flow to tendons that have been torn or otherwise damaged, so as to stimulate, expedite, or facilitate the healing process.

SUMMARY OF THE INVENTION

The present invention provides systems, apparatus and methods for selectively applying electrical energy to structures within or on the surface of a patient's body. The systems, apparatus, and methods of the present invention are particularly useful for treating acute and chronic musculoskeletal or neurological injuries and disorders, such as strains, sprains, tendinitis, fasciitis, arthritis, bursitis and tenosynovitis. In particular, the systems and methods of the present invention are useful for increasing blood flow to a target tissue, by canalization of tissue, stimulating the body's wound healing responses, such as inducing vascularization of tissue, stimulating collagen growth, altering cellular function, or other metabolic or physiologic events that promote healing and regeneration of injured tissue.

Systems and apparatus according to the present invention generally include an electrosurgical probe or catheter having a shaft with proximal and distal ends, one or more active electrode(s) at the distal end, and one or more connectors for coupling the active electrode(s) to a source of high frequency electrical energy. The distal end portion of the shaft will usually have a diameter of less than 3 mm, preferably less than 1 mm. The active electrode(s) are preferably supported within an electrically insulating support member typically formed of an inorganic material, such as a ceramic, a silicone rubber, or a glass.

In one method of the present invention, an active electrode is positioned in close proximity to tissue at a target site, and a high frequency voltage difference is applied between an active electrode and a return electrode to volumetrically remove or ablate tissue at the target site. The active electrode(s) may be translated or otherwise moved relative to the body structure during or after the application of electrical energy to form a void within the body structure, such as a hole, channel, stripe, crater, divot, surface damage, or the like. In some embodiments, the active electrode(s) are axially moved toward the body structure to volumetrically remove one or more channel(s), divot(s) or hole(s) through a portion of the structure. In other embodiments, the active electrode(s) are moved across the body structure to remove one or more stripe(s) or channel(s) of tissue. In most embodiments, electrically conductive fluid, such as isotonic saline, is located between the active electrode(s) and the body structure. In the bipolar modality, the conductive fluid generates a current flow path between the active electrode(s) and one or more return electrode(s). High frequency voltage is then applied between the active electrode(s) and the return electrode(s) through the current flow path created by the electrically conductive fluid.

In one aspect of the invention, a method is provided for vascularization or revascularization of a tendon, ligament, or meniscus. The present invention may be useful for acute muscle or tendon injury, iliotibial band syndrome, tendinitis, fasciitis, bursitis, tenosynovitis, strains, sprains and the like. In one embodiment of the present invention, artificial channels, holes, craters, or lumens are created during this procedure to vascularize the tendon and/or facilitate the healing process. In another embodiment, sufficient RF energy is applied to the tendon to vascularize a region around the target site without creating a hole, channel, crater or the like, in the tendon. According to the present invention, one or more active electrodes can be positioned adjacent to the tendon, and a voltage applied between the active electrode(s) and one or more return electrode(s). In an exemplary configuration, a high frequency voltage heats, damages, and/or ablates, (i.e. volumetrically removes) at least a portion of the tissue to be treated. The active electrode(s) can be advanced axially into the space vacated by the removed tissue to bore a channel through the tissue.

In one specific configuration, a void, hole, or crater is formed in the tendon by molecular dissociation or disintegration of tissue components. In these embodiments, the high frequency voltage applied to the active electrode(s) is sufficient to vaporize an electrically conductive fluid (e.g., a gel or isotonic saline) between the active electrode(s) and the tissue. Within the vaporized fluid, an ionized plasma is formed and charged particles (e.g., electrons) cause the molecular breakdown or disintegration of the tissue, perhaps to a depth of several cell layers. This molecular dissociation of tissue components is accompanied by the volumetric removal of the tissue. This process can be precisely controlled to effect the volumetric removal of tissue to a depth in the range of from about 10 microns to 150 microns, with minimal heating of, or damage to, surrounding or underlying tissue. A more complete description of this phenomenon is described in commonly assigned U.S. Pat. No. 5,683,366, the complete disclosure of which is incorporated by reference herein.

One of the advantages of the present invention, particularly over previous methods involving lasers, is that the surgeon can more precisely control the location, depth, and diameter of the vascularizing channels formed in the tissue. The ability to precisely control the volumetric removal of tissue results in a field of tissue ablation or removal that is very defined, consistent, and predictable. This precise control of tissue treatment also helps to minimize, or completely eliminate, damage to healthy tissue structures, such as muscles, cartilage, bone, and/or nerves, which may be adjacent to the target tissue. In addition, any severed blood vessels at the target site may be simultaneously cauterized and sealed as the tissue is removed to continuously maintain hemostasis during the procedure. This increases the surgeon's field of view, and expedites the procedure. In one embodiment, the active electrode can remain in contact with the tendon tissue as the high frequency voltage ablates this tissue (or at least substantially close to the tissue, e.g., usually on the order of about 0.1 mm to 2.0 mm, and preferably about 0.1 mm to 1.0 mm). This preserves tactile sense and allows the surgeon to more accurately determine when to terminate cutting of a given channel so as to minimize damage to surrounding tissues and/or to minimize bleeding.

In open procedures, or in procedures in "dry" fields, the apparatus may further include a fluid delivery element for delivering electrically conductive fluid to the active electrode(s) and the target site. The fluid delivery element may be located on the probe, e.g., in the form of a fluid lumen or tube, or it may be part of a separate instrument. In arthroscopic procedures, however, the surgical area surrounding the tendon will typically be filled with electrically conductive fluid (e.g., isotonic saline) so that the apparatus need not have a fluid delivery element. In both embodiments, the electrically conductive fluid will preferably generate a current flow path between the active electrode(s) and one or more return electrode(s). In an exemplary embodiment, the return electrode is located on the probe and spaced a sufficient distance from the active electrode(s) to substantially avoid or minimize current shorting therebetween and to shield the return electrode from tissue at the target site.

According to one aspect of the invention, there is provided an electrosurgical system including a probe having a shaft and an electrode assembly disposed on the shaft; an arthroscope for passing at least a distal end portion of the shaft therethrough; and a sensing unit adapted for determining a boundary of a target tissue. The sensing unit may include an element, such as an ultrasonic transducer, located on the shaft distal end, and an ultrasonic generator. The system may further include an adjustable mechanical stop for limiting the maximum travel of the shaft within a target tissue. The electrode assembly typically includes at least one active electrode and a return electrode. The system further includes a high frequency power supply for applying a high frequency voltage between the active and return electrodes. In one embodiment, the sensing unit may be coupled to the power supply, and the system configured to shut off power from the power supply according to a location of the shaft distal end in relation to a target tissue.

In one aspect, the invention provides a method for treating a damaged or poorly vascularized tissue, such as a meniscus of a joint, or a tendon. In one embodiment one or more channels or voids are formed in a target tissue via selective electrosurgical ablation of the tissue. One or more implants may be inserted in the one or more channels. In one embodiment, at least one channel bridges a lesion in the target tissue, and an implant inserted in the channel serves as a splint. In another embodiment, an implant is inserted in a channel to maintain patency in the channel, the channel serving as a conduit for blood flow within the target tissue, and the implant serving as a stent. In a further embodiment, an implant is inserted in a channel to promote hemostasis of the channel. In yet another embodiment, a stent is inserted in a distal portion of a channel, and a hemostasis plug is inserted in a proximal portion of the channel.

In another aspect, the invention provides a method for increasing blood flow to a target tissue by eliciting a wound healing response in the target tissue. In one embodiment, the wound healing response is elicited by the controlled application of heat thereto. Typically, the target tissue is heated using an electrosurgical probe to deliver high frequency, or radio frequency (RF), electrical energy thereto. Usually, the target tissue is heated to a temperature less than about 150° C.

The present invention includes methods for inducing a controlled inflammatory response in tissue by positioning an active electrode in close proximity to target tissue, removing a void in the tissue by applying a high frequency voltage to the active electrode, and forming a pattern of voids by repeating the positioning and applying acts. The pattern may be selected as needed and include such patterns as a grid, a circle, at least two circles, at least two concentric circles, a helical pattern, a linear pattern, a non-linear pattern, a random pattern, and a combination thereof.

The present invention also includes placing a template adjacent to the target tissue prior to the positioning step, wherein the template comprises a plurality of holes arranged in a layout similar to the pattern. The template may be used to guide the active electrode to create the voids or it may be used to mark locations for the voids. The template may further be used to separate tissue adjacent to the target tissue.

The invention further includes a template device for use in applying therapy to tissue, the template comprising a proximal surface and a distal surface, the distal surface being placed adjacent to tissue, a plurality of openings forming a pattern, the holes extending from the proximal surface to the distal surface, wherein at least the proximal surface and distal surface are bio-compatible and electrically non-conductive, and wherein the pattern comprises a pattern selected from a group consisting of a grid, a circle, at least two circles, at least two concentric circles, a helical pattern, a linear pattern, a non-linear pattern, a random pattern, and a combination thereof. The template device may also have a tissue retractor portion adapted to separate tissue.

Another variation of the invention includes the an electrosurgical device as described herein, further comprising a fluid delivery lumen extending at least through a portion of said instrument shaft and having an opening adjacent to an active electrode, and a self-contained fluid supply unit coupled to the fluid delivery element, the self-contained fluid supply comprising a reservoir, a fluid driving member, and a connector lumen, wherein the fluid driving member is moveably located in the fluid reservoir and the connector lumen fluidly couples the reservoir to the fluid delivery lumen.

The invention may also include kits including the template device, an electrosurgical device, and a self-contained fluid supply, all as described herein.

For a further understanding of the nature and advantages of the invention, reference should be made to the following description taken in conjunction with the accompanying drawings.

BRIEF DESCRIPTION OF THE DRAWINGS

FIG. 3 is a perspective view of the distal tip of another electrosurgical probe that does not incorporate a fluid lumen for delivering electrically conductive fluid to the target site;

FIG. 4A is an enlarged, cross-sectional view of the distal tip of the electrosurgical probe of FIG. 3 illustrating an electrode array;

FIG. 4B is an end view of the distal tip of the electrosurgical probe of FIG. 3;

DESCRIPTION OF THE INVENTION

Figure 1:
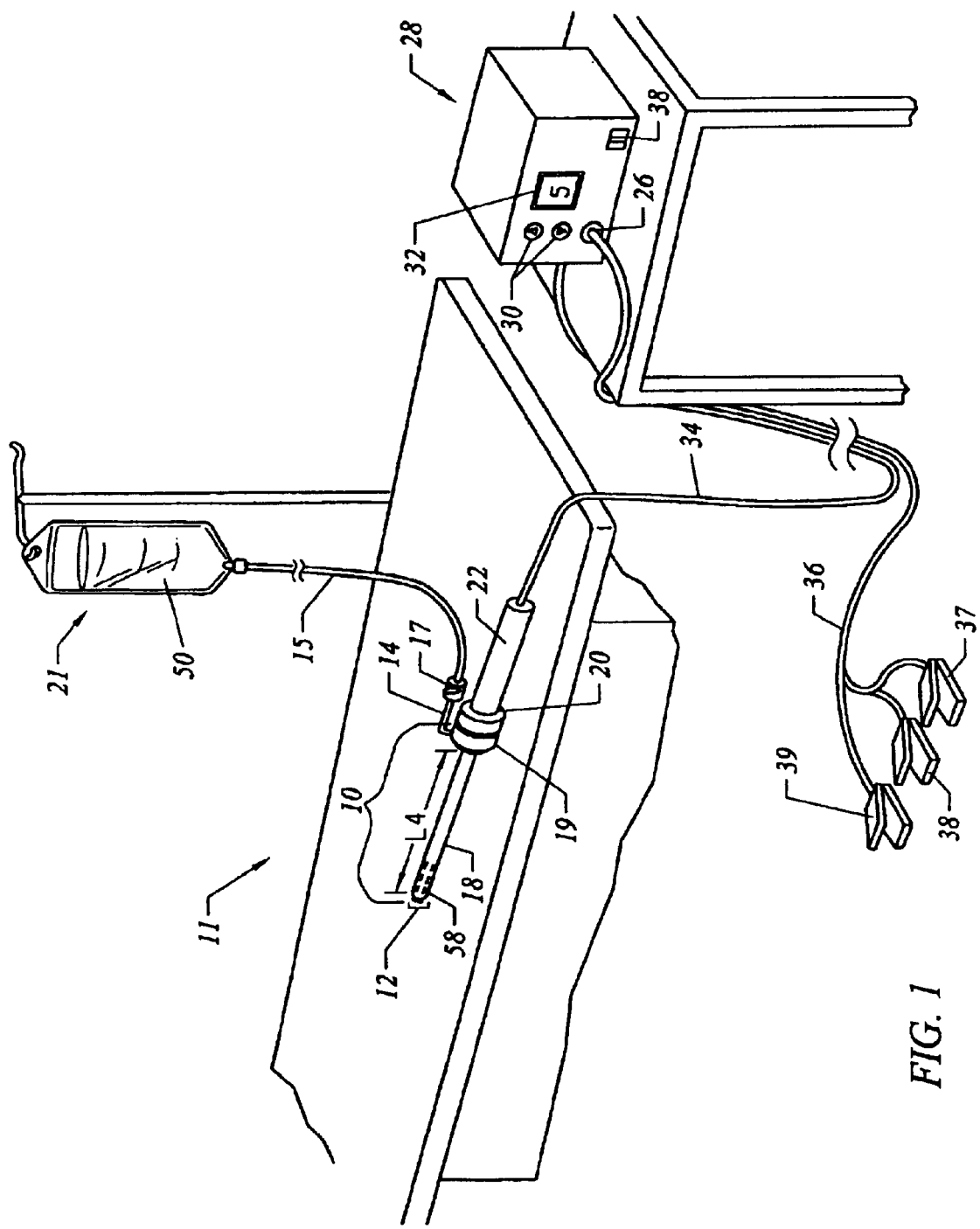
FIG. 1 is a perspective view of an electrosurgical system, including an electrosurgical probe, a fluid supply unit, and an electrosurgical power supply, constructed in accordance with the principles of the present invention.

The present invention provides systems, apparatus and methods for selectively applying electrical energy to a target location within or on a patient's body. In particular, the present invention provides systems, devices and methods for vascularizing a target tissue and for increasing blood flow to a region of tissue. In one aspect of the invention, blood flow within the heart is increased by creating lesions, such as artificial channels or lumens, within the myocardium. In another aspect of the invention, musculoskeletal injuries and disorders, such as strains, sprains, tendinitis, fasciitis, arthritis, bursitis and tenosynovitis, are treated by stimulating the body's wound healing response at the area treated. This wound healing response can include the stimulation of greater blood flow, collagen growth, as well as alteration of cellular function or of other metabolic events that promote healing and regeneration of injured tissue through a number of physiologic effects. In one specific embodiment, blood flow is increased to inner aspects of the meniscus by creating damage such as artificial channels or lumens from the outer aspect of the meniscus (which usually has a blood supply). In another specific embodiment, blood flow in a tendon is increased by creating damage to the tendon to invoke a would healing response.

It should be appreciated that the systems, devices, and methods of the invention can be applied equally well to procedures involving other tissues of the body, as well as to other procedures including open procedures, intravascular procedures, urological, laparoscopic, arthroscopic, thoracoscopic or other cardiac procedures, as well as dermatological, orthopedic, gynecological, otorhinolaryngological, spinal, and neurologic procedures, oncology and the like. For convenience, the remaining disclosure will be directed primarily to the revascularization of the heart, and to vascularization of meniscus tissue, and tendons.

In the present invention, high frequency (RF) electrical energy is applied to one or more active electrodes in the presence of electrically conductive fluid to remove and/or modify the structure of tissue structures. Depending on the specific procedure, the present invention may be used to: (1) create controlled damage to tissue; (2) volumetrically remove tissue, including bone and cartilage (i.e., ablate or effect molecular dissociation of the tissue structure); (3) form holes, channels, divots, or other spaces within tissue (4) cut or resect tissue; (5) shrink or contract collagen-containing connective tissue; and/or (6) coagulate severed blood vessels.

In one method, a target tissue is volumetrically removed or ablated. In this procedure, a high frequency voltage difference is applied between one or more active electrode(s) and one or more return electrode(s) to develop high electric field intensities in the vicinity of the target tissue. The high electric field intensities adjacent the active electrode(s) lead to electric field induced molecular breakdown of target tissue by molecular dissociation of tissue components (rather than by thermal evaporation or carbonization). Applicant believes that the tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of water from within the cells of the tissue, as is typically the case with conventional electrosurgical desiccation and vaporization.

The high electric field intensities may be generated by applying a high frequency voltage that is sufficient to vaporize an electrically conductive fluid over at least a portion of the active electrode(s) in the region between the distal tip of the active electrode(s) and the target tissue. The electrically conductive fluid may be a liquid, such as isotonic saline or blood, delivered to the target site, or a viscous fluid, such as a gel, applied to the target site. Since the vapor layer or vaporized region has a relatively high electrical impedance, it minimizes current flow into the electrically conductive fluid. This ionization, under the conditions described herein, induces the discharge of energetic electrons and photons from the vapor layer and to the surface of the target tissue. A more detailed description of this phenomenon, termed Coblation™, can be found in commonly assigned U.S. Pat. No. 5,683,366 the complete disclosure of which is incorporated herein by reference.

The present invention applies high frequency, or radio frequency (RF), electrical energy in an electrically conductive fluid environment to remove (i.e., resect, cut, or ablate) a target tissue structure, and to seal transected vessels within the region of the target tissue. The present invention is particularly useful for sealing larger arterial vessels, e.g., on the order of 1 mm or greater. In some embodiments, a high frequency power supply is provided having an ablation mode, wherein a first voltage is applied to an active electrode sufficient to effect molecular dissociation or disintegration of the tissue, and a coagulation mode, wherein a second, lower voltage is applied to an active electrode (either the same or a different electrode) sufficient to achieve hemostasis of severed vessels within the tissue. In other embodiments, an electrosurgical instrument is provided having one or more coagulation electrode(s) configured for sealing a severed vessel, such as an arterial vessel, and one or more active electrodes configured for either contracting collagen fibers within the tissue or removing (ablating) the tissue, e.g., by applying sufficient energy to the tissue to effect molecular dissociation of the tissue components. In the latter embodiments, the electrosurgical system or apparatus may be configured such that a single voltage can be applied to coagulate with the coagulation electrode(s), and to ablate target tissue with the active electrode(s). In other embodiments, the power supply is combined with the electrosurgical instrument such that the coagulation electrode is used when the power supply is in the coagulation mode (low voltage), and the active electrode(s) are used when the power supply is in the ablation mode (higher voltage).

The present invention is also useful for removing or ablating tissue around nerves, such as spinal, visceral, or cranial nerves, e.g., the olfactory nerve on either side of the nasal cavity, the optic nerve within the optic and cranial canals, the palatine nerve within the nasal cavity, soft palate, uvula and tonsil, etc. One of the significant drawbacks with prior art mechanical cutters and lasers is that these devices do not differentiate between the target tissue and the surrounding nerves or bone. Therefore, the surgeon must be extremely careful during these procedures to avoid damage to the bone or nerves within and around the nasal cavity. In the present invention, the Coblation™ process for removing tissue completely avoids damage to non-target tissue, or results in extremely small depths of collateral tissue damage, as discussed above. This allows the surgeon to remove tissue close to a nerve without causing collateral damage to the nerve fibers. A more complete description of this phenomenon can be found in co-pending U.S. patent application Ser. No. 09/032,375, filed Feb. 27, 1998, the complete disclosure of which is incorporated herein by reference.

In one method of the present invention, one or more active electrodes are brought into close proximity to tissue at a target site, and the power supply is activated in the ablation mode such that sufficient voltage is applied between the active electrodes and the return electrode to volumetrically remove the tissue via molecular dissociation, as described below. During this process, vessels within the tissue may be severed. Smaller vessels will be automatically sealed with the system and method of the present invention. Larger vessels, and those with a higher flow rate, such as arterial vessels, may not be automatically sealed while the system is operating in the ablation mode. In these cases, the severed vessels may be sealed by activating a control (e.g., a foot pedal) to reduce the voltage of the power supply into the coagulation mode. In this mode, the active electrodes may be pressed against the severed vessel to provide sealing and/or coagulation of the vessel. Alternatively, a coagulation electrode located on the same or a different instrument may be pressed against the severed vessel. Once the vessel is adequately sealed, the surgeon may activate a control (e.g., another foot pedal) to increase the voltage of the power supply back into the ablation mode.

The electrosurgical instrument will comprise a shaft having a proximal end and a distal end which supports an active electrode. The shaft may assume a wide variety of configurations, with the primary purpose being to mechanically support one or more active electrode and to permit the surgeon to manipulate the electrode(s) from the proximal end of the shaft. Usually, an electrosurgical probe shaft will be a narrow-diameter rod or tube, more usually having dimensions which permit it to be introduced into a body cavity, such as the thoracic cavity, through an associated trocar or cannula in a minimally invasive procedure, such as arthroscopic, laparoscopic, thoracoscopic, and other endoscopic procedures. Thus, the probe shaft will typically have a length of at least 5 cm for open procedures and at least 10 cm, more typically being 20 cm, or longer for endoscopic procedures. The probe shaft will typically have a diameter of at least about 0.5 mm, and will frequently be in the range from about 1 mm to 10 mm.

The electrosurgical probe may be delivered percutaneously (endoluminally) by insertion through a conventional or specialized guide catheter, or the invention may include a catheter having an active electrode array integral with its distal end. A shaft of the catheter may be rigid or flexible, with flexible shafts optionally being combined with a generally rigid external tube to provide mechanical support. Flexible shafts may be combined with pull wires, shape memory actuators, and other mechanisms for effecting selective deflection of the distal end of the shaft to facilitate positioning of the electrode or electrode array. Such mechanisms are known to the skilled artisan. The shaft of the probe or catheter will usually include a plurality of wires or other conductive elements running axially therethrough to permit connection of the electrode or electrode array and the return electrode to a connector at the proximal end of the shaft. Specific shaft designs will be described in detail in connection with the figures hereinafter.

The active electrode(s) are preferably supported within or by an electrically insulating support positioned near the distal end of the instrument shaft, e.g., a catheter body. The return electrode may be located on the instrument shaft, on another instrument, or on the external surface of the patient (i.e., a dispersive pad). When the present invention is used in close proximity to the heart, a bipolar design is more preferable because this minimizes the current flow through heart tissue. Accordingly, the return electrode is preferably either integrated with the catheter body, or with another instrument located in close proximity to the distal end of the catheter body. The proximal end of the catheter will include the appropriate electrical connections for coupling the return electrode(s) and the active electrode(s) to a high frequency power supply, such as an electrosurgical generator.

The current flow path between the active electrodes and the return electrode(s) may be generated by submerging the tissue site in an electrically conductive fluid (e.g., a viscous fluid, such as an electrically conductive gel), or by directing an electrically conductive fluid through a fluid outlet along a fluid path to the target site (i.e., a liquid, such as isotonic saline, or a gas, such as argon). The conductive gel may also be delivered to the target site to achieve a slower more controlled delivery rate of conductive fluid. In addition, the viscous nature of the gel may allow the surgeon to more easily contain the gel around the target site (e.g., as compared with containment of a liquid, such as isotonic saline). A more complete description of an exemplary method of directing electrically conductive fluid between active and return electrodes is described in U.S. Pat. No. 5,697,281, the contents of which are incorporated by reference herein in their entirety. Alternatively, the body's natural conductive fluids, such as blood, may be sufficient to establish a conductive path between the return electrode(s) and the active electrode(s), and to provide the conditions for establishing a vapor layer, as described above. Advantageously, a liquid electrically conductive fluid (e.g., isotonic saline) may be used to concurrently "bathe" the target tissue surface, to provide an additional means for removing any resected tissue fragments, and to cool the tissue at the target site during ablation.

In some embodiments, the electrode support and the fluid outlet may be recessed from an outer surface of the instrument or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the active electrode(s) and the return electrode(s) to maintain the conductive path therebetween. In addition, this will help to maintain a vapor layer and subsequent plasma layer between the active electrode(s) and the tissue at the treatment site throughout the procedure, which reduces the thermal damage that might otherwise occur if the vapor layer were extinguished due to a lack of conductive fluid. Provision of the electrically conductive fluid around the target site also helps to maintain the tissue temperature at desired levels.

The electrically conductive fluid should possess an electrical conductivity value above a minimum threshold level, in order to provide a suitable conductive path between the return electrode and the active electrode(s). The electrical conductivity of the fluid (in units of milliSiemens per centimeter or mS/cm) will usually be greater than about 0.2 mS/cm, typically will be greater than about 2 mS/cm and more typically greater than about 10 mS/cm. In an exemplary embodiment, the electrically conductive fluid is isotonic saline, which has a conductivity of about 17 mS/cm.

In some procedures, it may also be necessary to retrieve or remove, e.g., aspirate, any excess electrically conductive fluid and/or ablation by-products from the surgical site. For example, in procedures in and around the heart, or within blood vessels, it may be desirable to aspirate the fluid so that it does not enter the circulatory system. In addition, it may be desirable to aspirate small pieces of tissue fragments that are not completely disintegrated by the high frequency energy, or other fluids at the target site, such as blood, mucus, etc. Accordingly, the system of the present invention may include one or more suction lumen(s) in the instrument, or on another instrument, coupled to a suitable vacuum source for aspirating fluids from the target site. In some embodiments, the instrument also includes one or more aspiration electrode(s) coupled to the aspiration lumen for inhibiting clogging during aspiration of tissue fragments from the surgical site. A more complete description of these embodiments can be found in commonly assigned co-pending Application No. 09/010,382, filed Jan. 21, 1998, the complete disclosure of which is incorporated herein by reference for all purposes.

As an alternative to, or in addition to suction, it may be desirable to contain the excess electrically conductive fluid, tissue fragments and/or gaseous products of ablation at or near the target site with a containment apparatus, such as a basket, retractable sheath or the like. This embodiment has the advantage of ensuring that the conductive fluid, tissue fragments or ablation by-products do not flow into the heart or lungs. In addition, it may be desirable to limit the amount of suction to limit the undesirable effect suction may have on hemostasis of severed blood vessels within heart tissue.

The present invention may use a single electrode or an electrode array distributed over a distal contact surface of the electrosurgical instrument. In both configurations, the circumscribed area of the electrode or electrode array will generally depend on the desired diameter of the revascularizing channel. For example, applicant has found that smaller diameter channels tend to remain patent for a shorter period of time than larger diameter channels. Thus, a relatively large diameter channel (on the order of about 1.5 mm to 3.0 mm) may be desired to improve lumen patency. The ability to select the diameter of the artificial channels is one of the advantages of the present invention over existing laser procedures, which are typically limited by the concentration of light that is required to generate sufficient energy to ablate the tissue during the still or quiescent period of the heart (i.e., about 0.08 seconds). Usually, the area of the electrode array is in the range of from about 0.25 mm2 to 20 mm2, preferably from about 0.5 mm2 to 10 mm2, and more preferably from about 0.5 mm2 to 5.0 mm2. In addition, the shape of the array and the distal end of the instrument shaft will also depend on the desired surface area of the channel. For example, the ratio of the perimeter of the electrode array to the surface area of the electrodes may be maximized to increase blood flow from the channel to the surrounding myocardial tissue. Each electrode may take the form of a solid round wire, or a wire having other solid cross-sectional shapes such as squares, rectangles, hexagons, triangles, star-shaped, or the like, to provide a plurality of edges around the distal perimeter of the electrodes. Alternatively, each electrode may be in the form of a hollow metal tube having a cross-sectional shape which is round, square, hexagonal, rectangular or the like. The envelop or effective diameter of the individual electrode(s) ranges from about 0.05 mm to 3 mm, preferably from about 0.1 mm to 2 mm.

The electrode array will usually include at least one isolated active electrode, and in some embodiments may include at least four active electrodes, sometimes at least six active electrodes, and often 50 or more active electrodes, disposed over the distal contact surface(s) on the shaft. By bringing the electrode array(s) on the contact surface(s) in close proximity with the target tissue and applying high frequency voltage between the array(s) and an additional common or return electrode in direct or indirect contact with the patient's body, the target tissue is selectively damaged, ablated or cut, permitting selective removal of portions of the target tissue while desirably minimizing the depth of necrosis to surrounding tissue.

As described above, the present invention may use a single active electrode or an electrode array distributed over a distal contact surface of an electrosurgical instrument, such as a probe, a catheter or the like. The electrode array usually includes a plurality of independently current-limited and/or power-controlled active electrodes to apply electrical energy selectively to the target tissue while limiting the unwanted application of electrical energy to the surrounding tissue and environment resulting from power dissipation into surrounding electrically conductive fluids, such as blood, normal saline, and the like. The active electrodes may be independently current-limited by isolating the electrodes from each other and connecting each electrode to a separate power source that is isolated from the other active electrodes. Alternatively, the active electrodes may be connected to each other at either the proximal or distal ends of the probe to form a single wire that couples to a power source.

In one configuration, each individual active electrode in the electrode array is electrically insulated from all other active electrodes in the array within said instrument and is connected to a power source which is isolated from each of the other active electrodes in the array or to circuitry which limits or interrupts current flow to the active electrode when low resistivity material (e.g., blood, electrically conductive saline irrigant or electrically conductive gel) causes a lower impedance path between the return electrode and the individual active electrode. The isolated power sources for each individual active electrode may be separate power supply circuits having internal impedance characteristics which limit power to the associated active electrode when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the active electrodes through independently actuatable switches, or by independent current limiting elements, such as inductors, capacitors, resistors and/or combinations thereof. The current limiting elements may be provided in the instrument, connectors, cable, power supply, or elsewhere along the conductive path from the power supply or controller to the distal tip of the instrument. Alternatively, the resistance and/or capacitance may occur on the surface of the active electrode(s) due to oxide layers which form selected active electrodes (e.g., titanium or a resistive coating on the surface of metal, such as platinum).

The tip region of the instrument may comprise many independent active electrodes designed to deliver electrical energy in the vicinity of the tip. The selective application of electrical energy to the conductive fluid is achieved by connecting each individual active electrode and the return electrode to a power source having independently controlled or current limited channels. The return electrode(s) may comprise a single tubular member of conductive material proximal to the electrode array at the tip which also serves as a conduit for the supply of the electrically conductive fluid between the active and return electrodes. Alternatively, the instrument may comprise an array of return electrodes at the distal tip of the instrument (together with the active electrodes) to maintain the electric current at the tip. The application of high frequency voltage between the return electrode(s) and the electrode array results in the generation of high electric field intensities at the distal tips of the active electrodes with conduction of high frequency current from each individual active electrode to the return electrode. The current flow from each individual active electrode to the return electrode(s) is controlled by either active or passive means, or a combination thereof, to deliver electrical energy to the surrounding conductive fluid while minimizing energy delivery to surrounding (non-target) tissue.

The application of a high frequency voltage between the return electrode(s) and the active electrode(s) for appropriate time intervals effects cutting, removing, ablating, shaping, contracting or otherwise modifying the target tissue. The tissue volume over which energy is dissipated (i.e., over which a high current density exists) may be precisely controlled, for example, by the use of a multiplicity of small active electrodes whose effective diameters or principal dimensions range from about 5 mm to 0.01 mm, preferably from about 2 mm to 0.05 mm, and more preferably from about 1 mm to 0.1 mm. Electrodes (both circular and non-circular electrodes) will typically have a contact area (per active electrode) below about 25 mm2 for electrode arrays, and as large as 75 mm2 for single electrode embodiments, preferably being in the range from 0.0001 mm2 to 1 mm2, and more preferably from 0.005 mm2 to 0.5 mm2. The circumscribed area of the electrode array is in the range from 0.25 mm2 to 75 mm2, preferably from 0.5 mm2 to 40 mm2, and will usually include at least one, often at least two, isolated active electrodes, often at least five active electrodes, often greater than 10 active electrodes, and even 50 or more active electrodes, disposed over the distal contact surfaces on the shaft. The use of small diameter active electrodes increases the electric field intensity and reduces the extent or depth of tissue heating as a consequence of the divergence of current flux lines which emanate from the exposed surface of each active electrode.

The area of the tissue treatment surface can vary widely, and the tissue treatment surface can assume a variety of geometries, with particular areas and geometries being selected for specific applications. The active electrode surface(s) can have area(s) in the range from about 0.25 mm2 to 75 mm2, usually being from about 0.5 mm2 to 40 mm2. The geometries can be planar, concave, convex, hemispherical, conical, linear "in-line" array, or virtually any other regular or irregular shape. Most commonly, the active electrode(s) or active electrode array(s) will be formed at the distal tip of the electrosurgical instrument shaft, frequently being planar, disk-shaped, or hemispherical surfaces for use in reshaping procedures, or being linear arrays for use in cutting. Alternatively or additionally, the active electrode(s) may be formed on lateral surfaces of the electrosurgical instrument shaft (e.g., in the manner of a spatula), facilitating access to certain body structures in endoscopic procedures.

In one embodiment, an electrosurgical catheter or probe comprises a single active electrode that extends from an electrically insulating member, e.g., comprising a silicone rubber, a glass, or a ceramic, at the distal end of the shaft. In one embodiment, the insulating member comprises a tubular structure that separates the active electrode from a tubular or annular return electrode positioned proximal to the insulating member and the active electrode. In another embodiment, the catheter or probe includes a single active electrode that can be rotated relative to the rest of the catheter body, or the entire catheter may be rotated related to the lead. The single active electrode can be positioned adjacent the abnormal tissue (e.g., calcified deposits), energized, and rotated as appropriate to remove this tissue.

It should be clearly understood that the invention is not limited to electrically isolated active electrodes, or even to a plurality of active electrodes. For example, the array of active electrodes may be connected to a single lead that extends through the instrument shaft to a power source of high frequency current. Alternatively, the instrument may incorporate a single electrode that extends directly through the catheter shaft or is connected to a single lead that extends to the power source. The active electrode(s) may have ball shapes (e.g., for tissue vaporization and desiccation), twizzle shapes (for vaporization and needle-like cutting), spring shapes (for rapid tissue debulking and desiccation), twisted metal shapes, annular or solid tube shapes, or the like. Alternatively, the electrode(s) may comprise a plurality of filaments, rigid or flexible brush electrode(s) (for debulking a tumor, such as a fibroid, bladder tumor or a prostate adenoma), side-effect brush electrode(s) on a lateral surface of the shaft, coiled electrode(s), or the like.

The power supply may include a fluid interlock for interrupting power to the active electrode(s) when there is insufficient electrically conductive fluid around the active electrode(s). This ensures that the instrument will not be activated when conductive fluid is not present, minimizing the tissue damage that may otherwise occur. A more complete description of such a fluid interlock can be found in commonly assigned, co-pending U.S. Application No. 09/058,336, filed Apr. 10, 1998, the complete disclosure of which is incorporated herein by reference.

The voltage difference applied between the return electrode(s) and the active electrode(s) will be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the active electrode size, the operating frequency and the operation mode of the particular procedure or desired effect on the tissue (e.g., contraction, coagulation, cutting or ablation). Typically, the peak-to-peak voltage for ablation or cutting of tissue will be in the range of from about 10 volts to 2000 volts, usually in the range of 200 volts to 1800 volts, and more typically in the range of about 300 volts to 1500 volts, often in the range of about 500 volts to 900 volts peak to peak (again, depending on the electrode size, the operating frequency and the operation mode). Lower peak-to-peak voltages will be used for tissue coagulation or collagen contraction and will typically be in the range from 50 to 1500, preferably from about 100 to 1000, and more preferably from about 120 to 600 volts peak-to-peak.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 Hz to 20 Hz). In addition, the duty cycle (i.e., cumulative time in any one-second interval that energy is applied) is on the order of about 50% for the present invention, as compared with pulsed lasers which typically have a duty cycle of about 0.0001%. With the above voltage and current ranges, applicant has found that the electrosurgical instrument will usually bore a channel completely through the heart wall in about 0.5 seconds to 20.0 seconds, preferably about 1.0 second to 3.0 seconds in the continuous mode, and preferably about 10 seconds to 15 seconds in the pulsed mode. It has been found that channels that are approximately 0.5 mm to 3.0 mm in diameter and approximately 1 cm to 4 cm deep may be easily and efficiently formed in the heart wall by this method, and that the revascularization procedure dramatically improves the flow of blood to the heart muscle.

The capability to form the desired channel over a longer period of time significantly reduces the amount of instantaneous power required to complete the channel. By way of example, CO2 lasers used for LMR typically deliver the power for each channel within an elapsed time of 0.08 seconds. By contrast, the present invention can be used to complete the canalization of the same sized channel within about 1.0 second. As a result, the laser requires about 500 watts to 700 watts to form a 1 mm diameter channel while the present invention requires only 1/12 that amount of power, or about 42 watts to 58 watts, to form the same channel. If larger channels are required, the power requirements increase by the square of the ratio of the diameter. Hence, to produce a 2 mm channel in 0.08 seconds using a CO2 laser, the required power will be four-fold higher or 2000 watts to 2800 watts, which requires a very large and very expensive laser. In contrast, the present invention can form a 2 mm diameter channel (of the same length as that cited above) in 1 second with an applied power of about 168 watts to 232 watts.

The preferred power source of the present invention delivers a high frequency current selectable to generate average power levels ranging from several milliwatts to tens of watts per electrode, depending on the volume of target tissue being treated, and/or the maximum allowed temperature selected for the instrument tip. The power source allows the user to select the voltage level according to the specific requirements of a particular cardiac surgery, arthroscopic surgery, dermatological procedure, ophthalmic procedure, open surgery, or other endoscopic surgery procedure. For cardiac procedures, the power source may have an additional filter, for filtering leakage voltages at frequencies below 100 kHz, particularly voltages around 60 kHz. A description of a suitable power source can be found in co-pending U.S. patent application Ser. Nos. 09/058,571 and 09/058,336, filed Apr. 10, 1998, the complete disclosure of both of which are incorporated herein by reference for all purposes.

The power source may be current limited or otherwise controlled so that undesired heating of the target tissue or surrounding (non-target) tissue does not occur. In a presently preferred embodiment of the present invention, current limiting inductors are placed in series with each independent active electrode, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current limiting resistors may be selected. Preferably, these resistors will have a large positive temperature coefficient of resistance so that, as the current level begins to rise for any individual active electrode in contact with a low resistance medium (e.g., saline irrigant or blood), the resistance of the current limiting resistor increases significantly, thereby minimizing the power delivery from said active electrode into the low resistance medium (e.g., saline irrigant or blood).

In yet another aspect of the invention, the control system is "tuned" so that it will not apply excessive power to the blood (e.g., in the ventricle), once the electrosurgical instrument crosses the wall of the heart and enters the chamber of the left ventricle. This minimizes the formation of a thrombus in the heart (i.e., the system will not induce thermal coagulation of the blood). The control system may include an active or passive architecture, and will typically include a mechanism for sensing resistance between a pair(s) of active electrodes at the distal tip, or between one or more active electrodes and a return electrode, to sense when the electrode array has entered into the blood-filled chamber of the left ventricle. Alternatively, current limiting means may be provided to prevent sufficient joulean heating in the lower resistivity blood to cause thermal coagulation of the blood. In another alternative embodiment, an ultrasound transducer at the tip of the instrument can be used to detect the boundary between the target tissue and adjacent non-target tissue, e.g., between blood in the ventricle and the heart wall; or between a layer of abnormal tissue and underlying healthy tissue.

Referring now to the drawings in detail, wherein like numerals indicate like elements, an electrosurgical system 11 is shown in FIG. 1 constructed according to the principles of the present invention. Electrosurgical system 11 generally comprises an electrosurgical instrument or probe or catheter 10 connected to a power supply 28 for providing high frequency voltage to electrosurgical instrument 10 and a fluid source 21 for supplying electrically conductive fluid 50 to probe 10.

In an exemplary embodiment as shown in FIG. 1, electrosurgical probe 10 includes an elongated shaft 13 which may be flexible or rigid, with flexible shafts optionally including support cannulas or other structures (not shown). It will be recognized that the probe shown in FIG. 1 will generally be employed in open or thoracoscopic procedures through intercostal penetrations in the patient. For endoluminal procedures into the ventricle, a delivery catheter 200 (FIGS. 6 and 11) will typically be employed, as discussed below. Probe 10 includes a connector 19 at its proximal end and a single active electrode (not shown) or an array 12 of active electrodes 58 disposed on the distal tip of shaft 13. A connecting cable 34 has a handle 22 with a connector 20 which can be removably connected to connector 19 of probe 10. The proximal portion of cable 34 has a connector 26 to removably couple probe 10 to power supply 28. The active electrodes 58 are electrically isolated from each other and each of the electrodes 58 is connected to an active or passive control network within power supply 28 by means of a plurality of individually insulated conductors 42 (see FIG. 2A). Power supply 28 can have a selection means 30 to change the applied voltage level. Power supply 28 can also include an element or device for energizing the electrodes 58 of probe 10 through the depression of a pedal 39 in a foot pedal 37 positioned close to the user. The foot pedal 37 may also include a second pedal (not shown) for remotely adjusting the voltage level applied to electrodes 58. The specific design of a power supply which may be used with the electrosurgical probe of the present invention is described in parent application PCT U.S. application Ser. No. 94/051,168, the full disclosure of which is incorporated herein by reference.

Figure 2A:
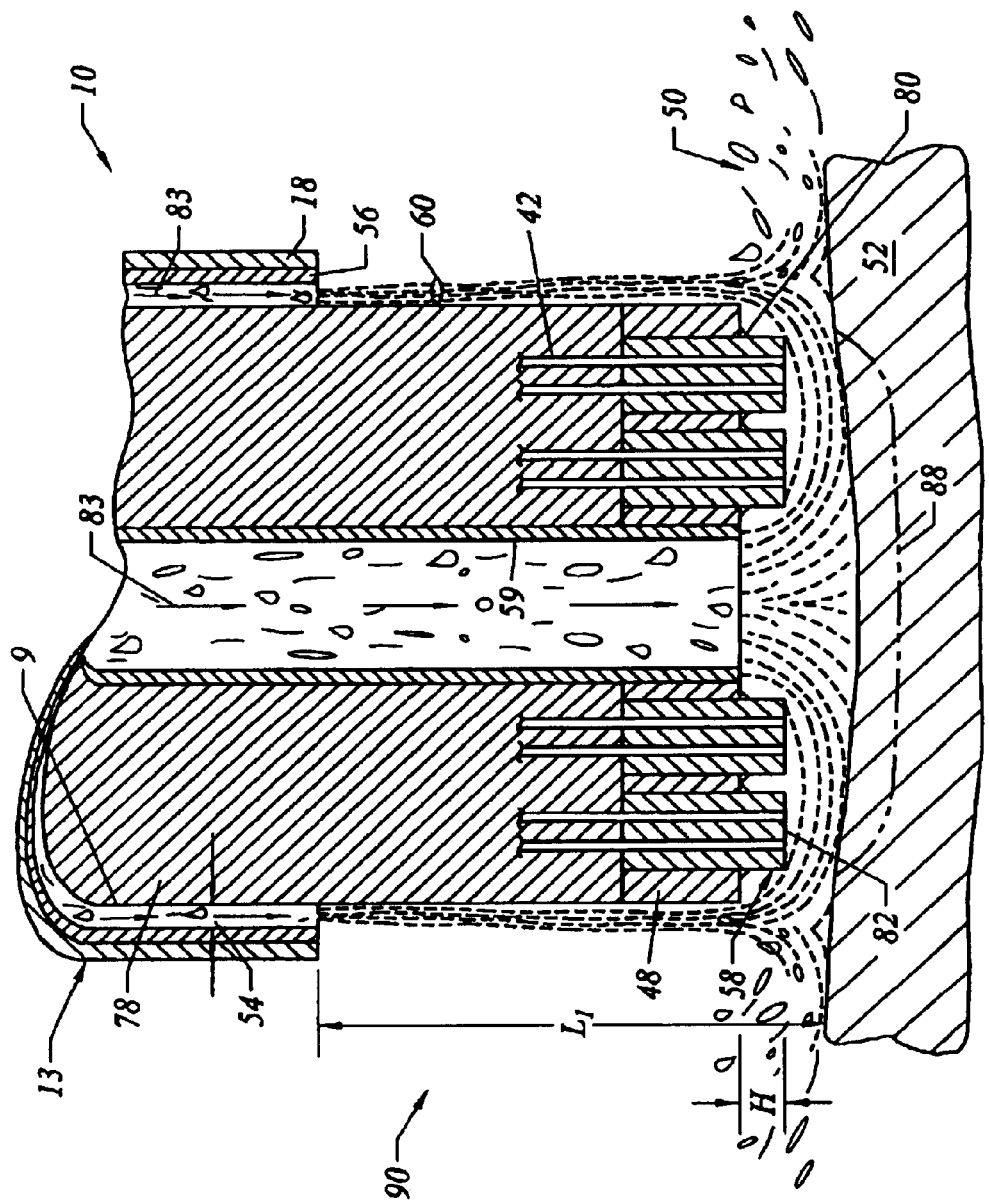
FIG. 2A is an enlarged cross-sectional view of the distal tip of an electrosurgical probe, according to one embodiment of the invention.
Figure 2B:
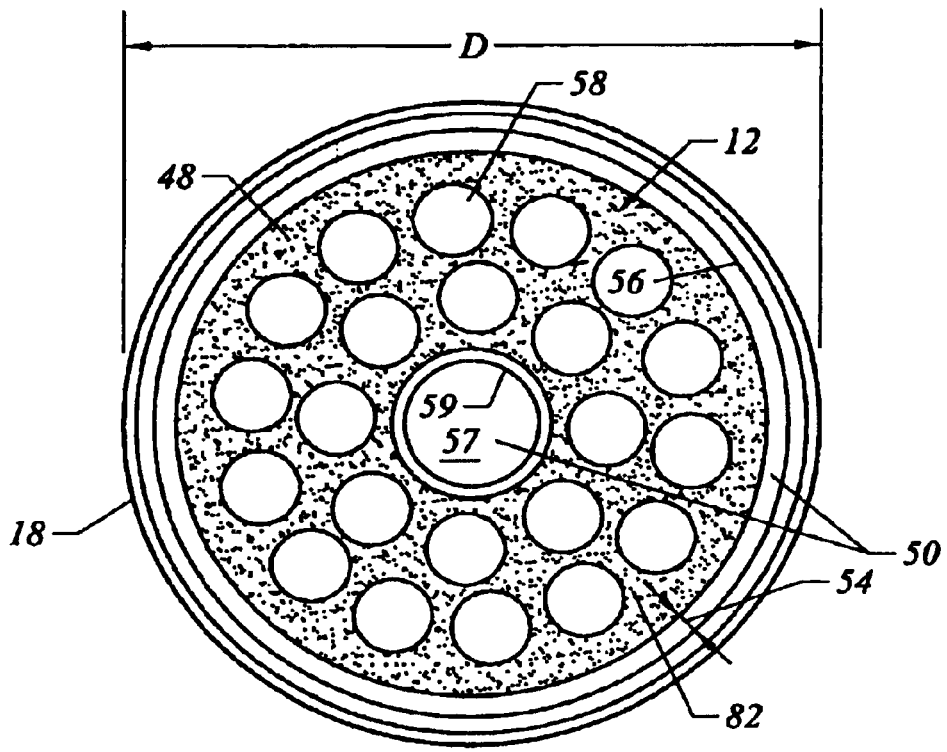
FIG. 2B is an end view of the electrosurgical probe of FIG. 2A.
Figure 8:
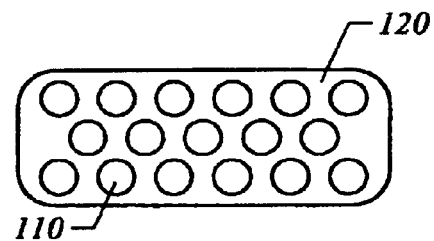

Referring to FIGS. 2A and 2B, the electrically isolated active electrodes 58 are spaced-apart over an electrode array surface 82. The electrode array surface 82 and individual active electrodes 58 will usually have dimensions within the ranges set forth above. In the preferred embodiment, the electrode array surface 82 has a circular cross-sectional shape with a diameter D (FIG. 2B) in the range of from about 0.3 mm to 4 mm. Electrode array surface 82 may also have an oval or rectangular shape, having a length L in the range of 1 mm to 20 mm and a width W in the range from 0.3 mm to 7 mm, as shown in FIG. 8 (discussed below). The individual active electrodes 58 can protrude over the electrode array surface 82 by a distance (H) from 0 mm to 2 mm, preferably from 0 mm to 1 mm (see FIG. 2A).

The active electrodes 58 are preferably composed of an electrically conductive metal or alloy, such as platinum, titanium, tantalum, tungsten, niobium, stainless steel, and the like. One preferred material for electrodes 58 is tungsten because of its known biocompatibility and resistance to erosion under the application of high voltages. As shown in FIG. 2B, the active electrodes 58 are anchored in a support matrix 48 of suitable insulating material (e.g., ceramic, glass/ceramic, or glass material, such as alumina, silica glass, and the like) which could be formed at the time of manufacture in a flat, hemispherical or other shape according to the requirements of a particular procedure. In an exemplary embodiment, the support matrix 48 will comprise an inorganic insulator, such as ceramic, glass, glass/ceramic, or a high resistivity material, such as silicon or the like. An inorganic material is generally preferred for the construction of the support matrix 48 since organic or silicone based polymers are known to rapidly erode during sustained periods of the application of high voltages between active electrodes 58 and the return electrode 56 during tissue ablation. However, for situations in which the total cumulative time of applied power is less than about one minute, organic or silicone based polymers may be used without significant erosion and loss of material of the support matrix 48 and, therefore, without significant reduction in ablation performance.

As shown in FIG. 2A, the support matrix 48 is adhesively joined to support member 9, which extends most or all of the distance between matrix 48 and the proximal end of probe 10. In a particularly preferred construction technique, support matrix 48 comprises a plurality of glass or ceramic hollow tubes 400 (FIG. 2D) extending from the distal end of shaft 13. In this embodiment, active electrodes 58 are each inserted into the front end of one of the hollow tubes 400 and adhered to the hollow tubes 400 so that the electrodes 58 extend distally from each hollow tube 400 by the desired distance, H. The electrodes 58 are preferably bonded to the hollow tubes 400 by a sealing material 402 (e.g., epoxy) selected to provide effective electrical insulation, and good adhesion to both the hollow tubes 400 and the active electrodes 58. Alternatively, hollow tubes 400 may be comprised of a glass having a coefficient of thermal expansion similar to that of active electrode 58 and may be sealed around the active electrode 58 by raising the temperature of the glass tube to its softening point according to the procedures commonly used to manufacture glass-to-metal seals. Referring to FIG. 2D, lead wires 406, such as insulation 408 covered copper wires, are inserted through the back end of the hollow tubes 400 and coupled to the electrodes 58 with a suitable conductive adhesive 404. The glass tube/active electrode assembly is then placed into the distal end of support member 9 to form the electrode array as shown in FIG. 2E. Alternatively, the lead wire 406 and active electrode 58 may be constructed of a single wire (e.g., stainless steel or nickel alloy) with insulation 408 removed over the length of the wire inserted into the hollow tube 400. As before, sealing material 402 is used to seal annular gaps between hollow tube 400 and active electrode 58 and to adhesively join active electrode 58 to hollow tube 400. Other features of construction are discussed below and shown in FIG. 2E.

In the embodiment shown in FIGS. 1, 2A and 2B, probe 10 includes a return electrode 56 for completing the current path between active electrodes 58 and power supply 28. Shaft 13 preferably comprises an electrically conducting material, usually metal, which is selected from the group consisting of stainless steel alloys, platinum or its alloys, titanium or its alloys, molybdenum or its alloys, and nickel or its alloys. The return electrode 56 may be composed of the same metal or alloy which forms the active electrodes 58 to minimize any potential for corrosion or the generation of electrochemical potentials due to the presence of dissimilar metals contained within an electrically conductive fluid 50, such as isotonic saline (discussed in greater detail below).

Figure 2C:
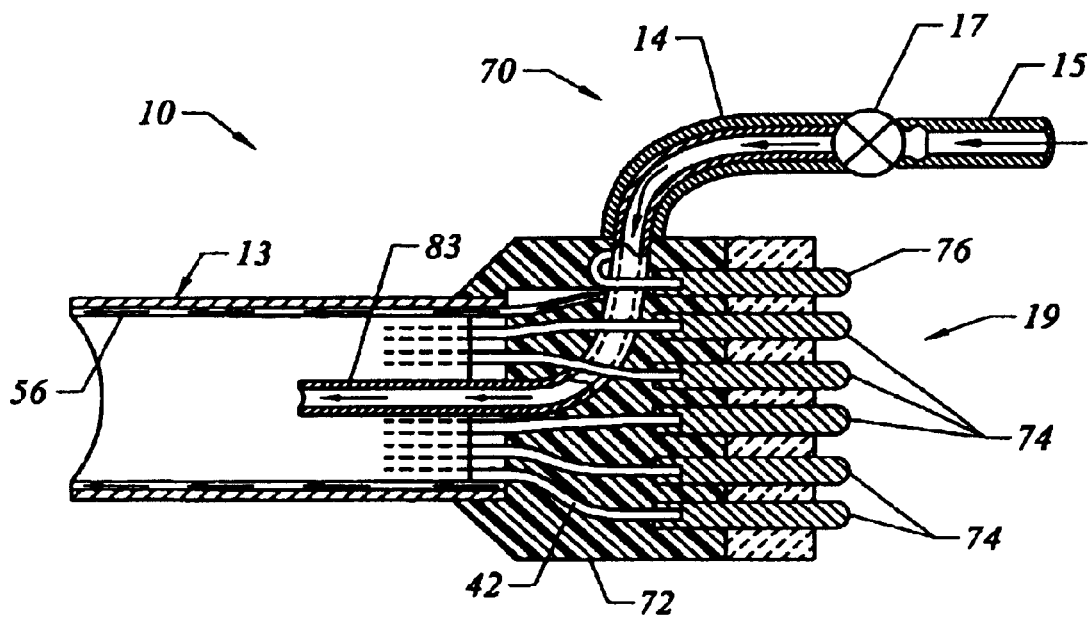
FIG. 2C is a cross-sectional view of the proximal end of the electrosurgical probe of FIG. 2A, illustrating an arrangement for coupling the probe to the electrically conductive fluid supply of FIG. 1.
Figure 2D:
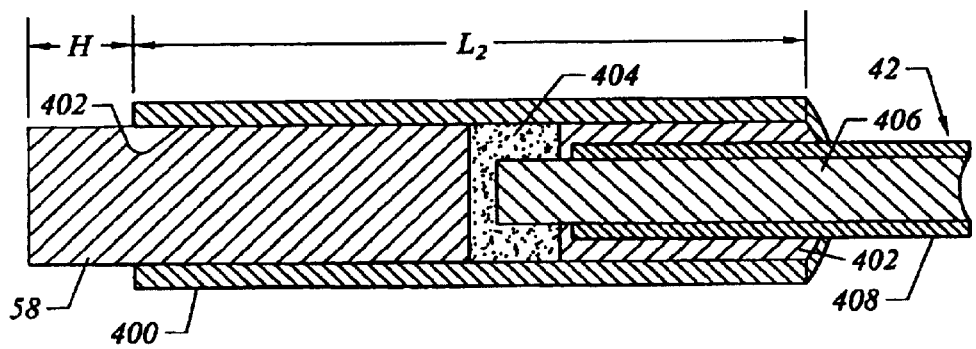
FIGS. 2D and 2E are cross-sectional views of the distal end of the electrosurgical probe of FIG. 2A, illustrating one method of manufacturing the active electrodes and insulating matrix of the probe.
Figure 2E:
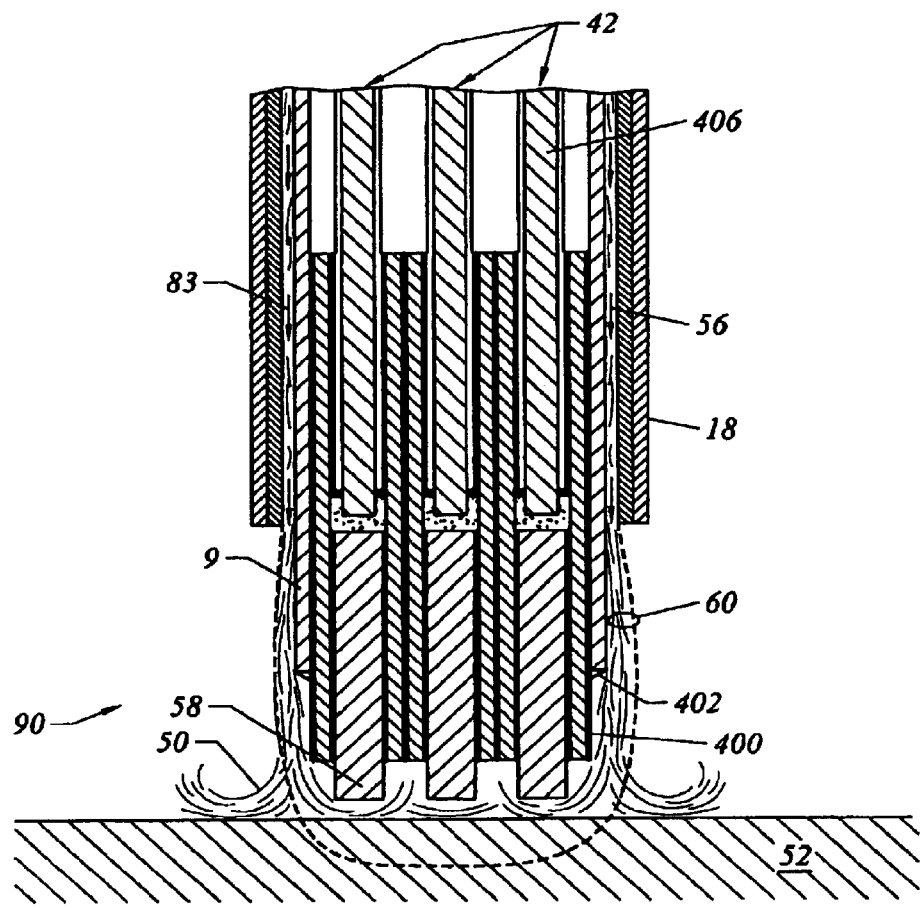

As shown in FIGS. 2A, 2B, and 2C, return electrode 56 extends from the proximal end of probe 10, where it is suitably connected to power supply 28 via connectors 19, to a point slightly proximal of electrode array surface 82, typically about 0.5 mm to 10 mm, and more preferably about 1 mm to 10 mm, proximal to surface 82. Shaft 13 is disposed within an electrically insulative jacket 18, which is typically formed as one or more electrically insulative sheaths or coatings, such as polyester, polytetrafluoroethylene, polyimide, and the like. The provision of the electrically insulative jacket 18 over shaft 13 prevents direct electrical contact between shaft 13 and any adjacent body structure or the surgeon. Such direct electrical contact between a body structure and an exposed return electrode 56 could result in unwanted heating of the structure at the point of contact causing necrosis.

In the embodiment shown in FIGS. 2A–2C, return electrode 56 is not directly connected to active electrodes 58. To complete this current path so that electrodes 58 are electrically connected to return electrode 56 via target tissue 52, electrically conductive fluid 50 (e.g., isotonic saline) is caused to flow along fluid paths 83. A fluid path 83 is formed by annular gap 54 between outer return electrode 56 and tubular support member 78. An additional fluid path 83 may be formed between an optional inner lumen 57 within an inner tubular member 59. The electrically conductive fluid 50 delivered to the distal end of instrument 10 provides a pathway for electrical current flow between target tissue 52 and return electrode 56, as illustrated by the current flux lines 60 in FIG. 2A. When a voltage difference is applied between electrode array 12 and return electrode 56, high electric field intensities will be generated at the distal tips of electrodes 58 with current flow from array 12 through the target tissue to return electrode 56, the high electric field intensities causing ablation of tissue 52 in zone 88.

FIG. 2C illustrates the proximal or connector end 70 of probe 10 in the embodiment of FIGS. 2A and 2B. Connector 19 comprises a plurality of individual connector pins 74 positioned within a housing 72 at the proximal end 70 of probe 10. Active electrodes 58 and the attached insulating conductors 42 extend proximally to connector pins 74 in connector housing 72. Return electrode 56 extends into housing 72, where it can bend radially outward to exit probe 10. As shown in FIG. 1, a fluid supply tube 15 can be removably coupled to fluid source 21, (e.g., a bag of electrically conductive fluid elevated above the surgical site or having a pumping device) and a control valve 17 located proximal to return electrode 56. Preferably, an insulating jacket 14 covers at least a portion of return electrode 56. One of the connector pins 76 is electrically connected to return electrode 56 to couple electrode 56 to power supply 28 via cable 34. A control valve 17 allows the surgical team to regulate the flow of electrically conductive fluid 50.

FIGS. 3, 4A, and 4B illustrate another preferred embodiment of the present invention. In this embodiment, a probe 100 does not include a fluid channel for directing electrically conductive fluid to the target site. Applicant has found that the fluids in the patient's heart tissue, such as blood, usually have a sufficient amount of electrical conductivity to complete the electrical path between the active electrode array and the return electrodes. In addition, these fluids will often have the requisite properties discussed above for establishing a vapor layer, creating regions of high electric fields around the edges of active electrodes 58 and inducing the discharge of energetic electrons and photons from the vapor layer to the surface of the target tissue to effect ablation.

As shown in FIG. 3, electrosurgical probe 100 typically has a shaft 102 with an exposed distal end 104 and a proximal end (not shown) similar to the proximal end shown in FIG. 2C. Aside from exposed distal end 104, which functions as the return electrode in this embodiment, the entire shaft 102 is preferably covered with an electrically insulative jacket 106, which is typically formed as one or more electrically insulative sheaths or coatings, such as polyester, polytetrafluoroethylene, polyimide, and the like, to prevent direct electrical contact between shaft 102 and any adjacent body structure or the surgeon. Similar to the embodiments described hereinabove, probe 100 typically includes an array 108 of active electrodes 110 having substantially the same applied potential. Electrodes 110 extend from an insulating inorganic matrix 112 attached to distal end 104 of shaft 102. As discussed above, matrix 112 is only shown schematically in the drawings, and preferably comprises an array of glass or ceramic tubes extending from distal end 104 or is a ceramic spacer through which active electrodes 110 extend.

The electrode array may have a variety of different configurations other than the one shown in FIGS. 3, 4A, and 4B. For example, as shown in FIG. 8, the distal end of the shaft 102 and/or the insulating matrix may have a substantially rectangular shape with rounded corners so as to maximize the perimeter length to cross-sectional area ratio of the distal tip of the probe. As shown, electrode array surface 120 (FIG. 8) has a rectangular shape having a width in the range of from about 2 mm to 5 mm and a length in the range of from about 1 mm to 2 mm. Increasing the perimeter of an artificial channel formed in a tissue may have advantages in that blood flowing through the artificial channel will have a greater area to pass into the tissue for a given cross-sectional area. Thus, this configuration can be a more efficient method of increasing blood flow to a region of tissue.

Figure 9:
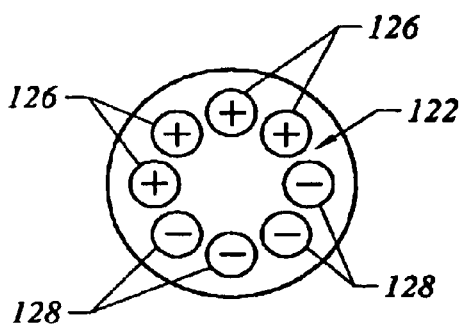
Figure 10:
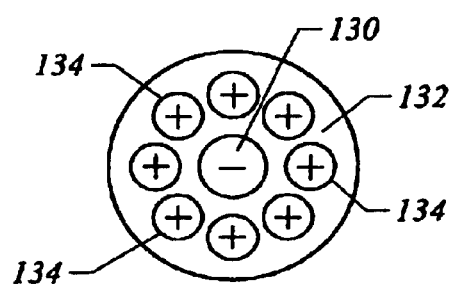

In another embodiment, the return electrode is positioned on the front or distal face of the probe. This configuration inhibits current flow within the tissue on the sides of the probe as it forms the revascularizing channel. In one configuration, for example (shown in FIG. 9), the electrode array surface 122 includes multiple pairs of electrodes, with each pair of electrodes including an active electrode 126 and a return electrode 128. Thus, as shown, the high frequency current passes between the pairs across the distal surface 122 of the probe. In another configuration (shown in FIG. 10), the return or common electrode 130 is positioned in the center of the distal probe surface 132 and the active electrodes 134 are positioned at its perimeter. In this embodiment, the electrosurgical current will flow between active electrodes 134 at the perimeter of distal surface 132 and return electrode 130 at its center to form the revascularizing channel. This allows the surgeon to more precisely control the diameter of the revascularizing channel because the current will generally flow radially from the outer active electrodes 134 to the return electrode 130. For this reason, electrodes 134 will preferably be positioned on the perimeter of distal surface 132 (i.e., further radially outward than shown in FIG. 10) to avoid tearing of non-ablated tissue by the perimeter of the probe shaft.

Figure 6:
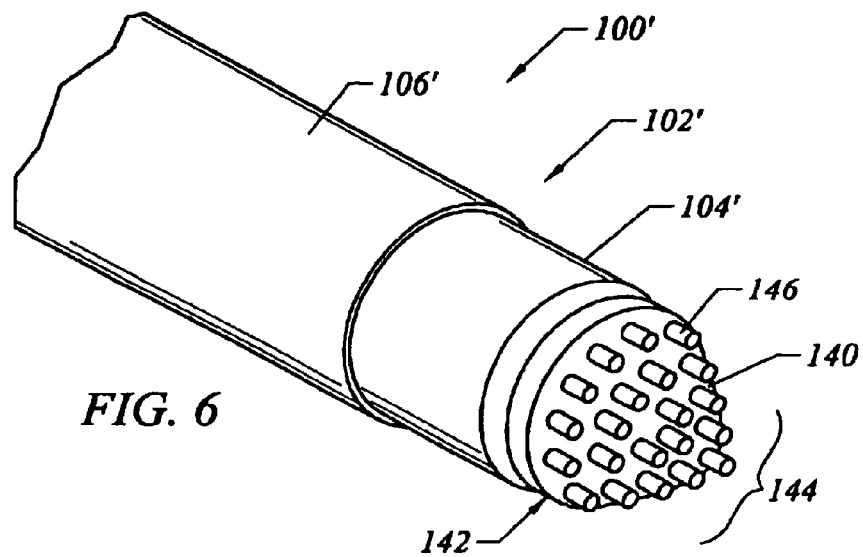
FIGS. 6–10 illustrate alternative electrode arrangements for the probes of FIGS. 1–4 or the catheter of FIG. 5.
Figure 7:
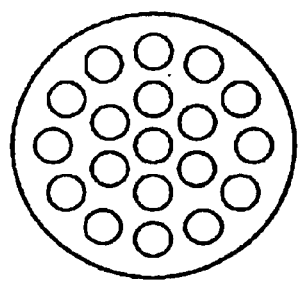

FIG. 6 illustrates yet another embodiment of an electrosurgical probe 100' according to the present invention. In this embodiment, the distal tip of the probe has a conical shape and includes an array of active electrodes along the conical surface 140. A conical shape provides less resistance to the advancement of the probe through dense tissue. As shown in FIG. 6, insulating matrix 142 tapers in the distal direction to form conical distal surface 140. The electrode array 144 extends from distal surface 140, with each active electrode 146 arranged to protrude axially from the conical surface 140 (i.e., rather than protruding perpendicularly from the surface 140). With this configuration, the electrodes 146 do not extend radially outward from the conical surface 140, which reduces the risk of electric current flowing radially outward to heart tissue surrounding the revascularizing channel. In addition, the high electric field gradients generated by the electric current concentrate near the active electrode surfaces and taper further away from these surfaces. Therefore, this configuration places these high electric field gradients within the diameter of the desired channel to improve ablation of the channel, while minimizing ablation of tissue outside of the desired channel.

Figure 5:
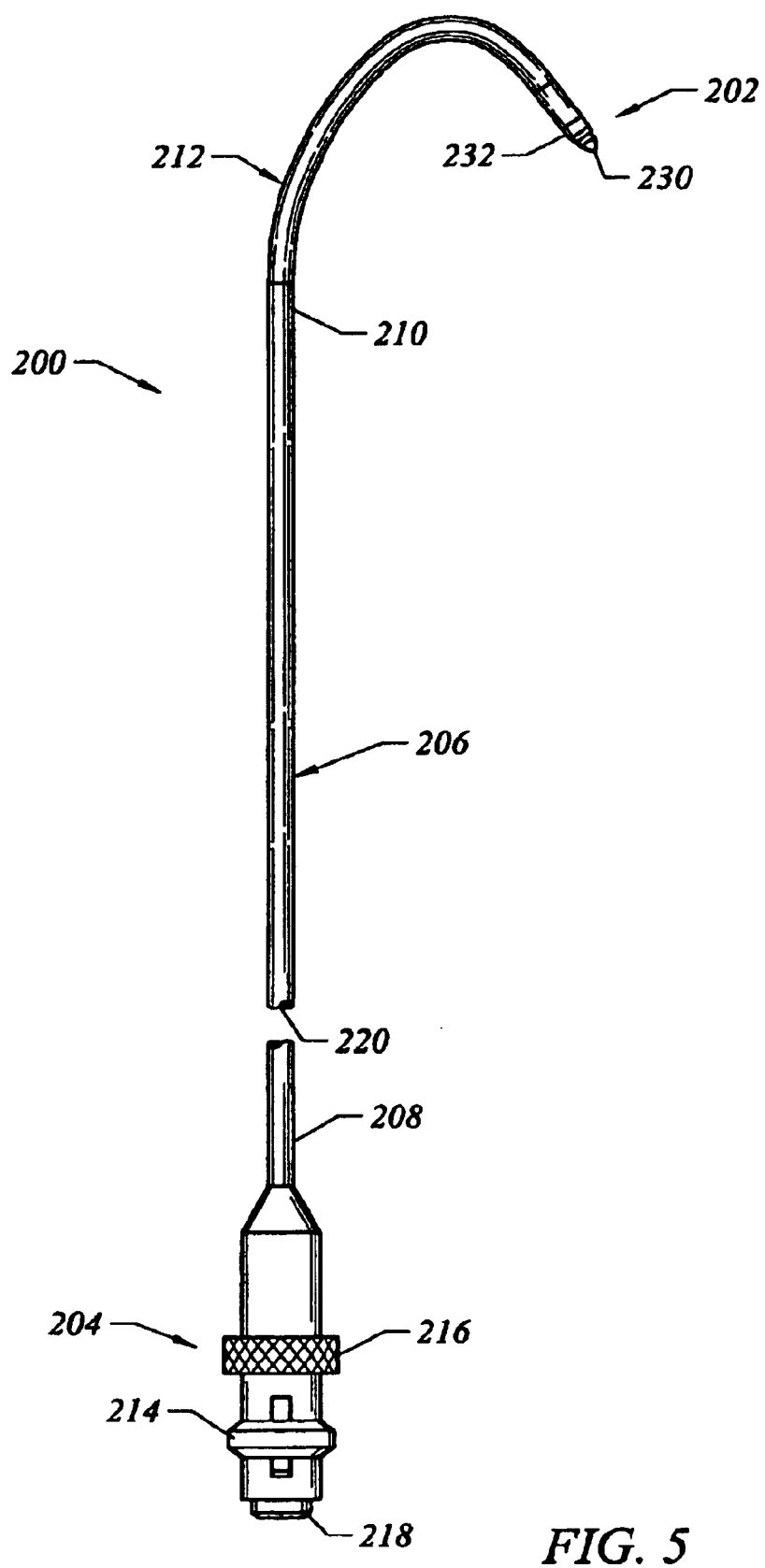
FIG. 5 is a perspective view of a catheter having a shaft with an electrosurgical arrangement at its distal end.

FIG. 5 illustrates a preferred delivery catheter 200 for introducing an electrosurgical probe 202 through a percutaneous penetration in the patient, and endoluminally delivering probe 202 to the target site (e.g., a ventricle of the heart as described in detail below). Catheter 200 generally includes a shaft 206 having a proximal end 208 and a distal end 210. Catheter 200 includes a handle 204 secured to proximal end 208, and preferably a deflectable tip 212 coupled to distal end 210 of shaft 206. Probe 202 typically has a length in the range of from about 100 cm to 200 cm. Handle 204 includes a variety of actuation mechanisms for manipulating tip 212 within the patient's heart, such as a tip actuation slide 214 and a torque ring 216, as well as an electrical connector 218. Catheter shaft 206 will generally define one or more inner lumens 220, and one or more manipulator wires and electrical connections (not shown) may extend through lumens (22) to probe 202.

In a first aspect, with reference to FIGS. 11–23, the present invention provides methods for increasing the blood flow to the heart through a transmyocardial revascularization procedure to form artificial channels through the heart wall to perfuse the myocardium. These procedures are an alternative to coronary artery bypass surgery for treating coronary artery disease. The channels allow oxygen enriched blood flowing into the ventricular cavity to directly flow into the myocardium, rather than exiting the heart and then flowing back into the myocardium through the coronary arteries.

Figure 11:
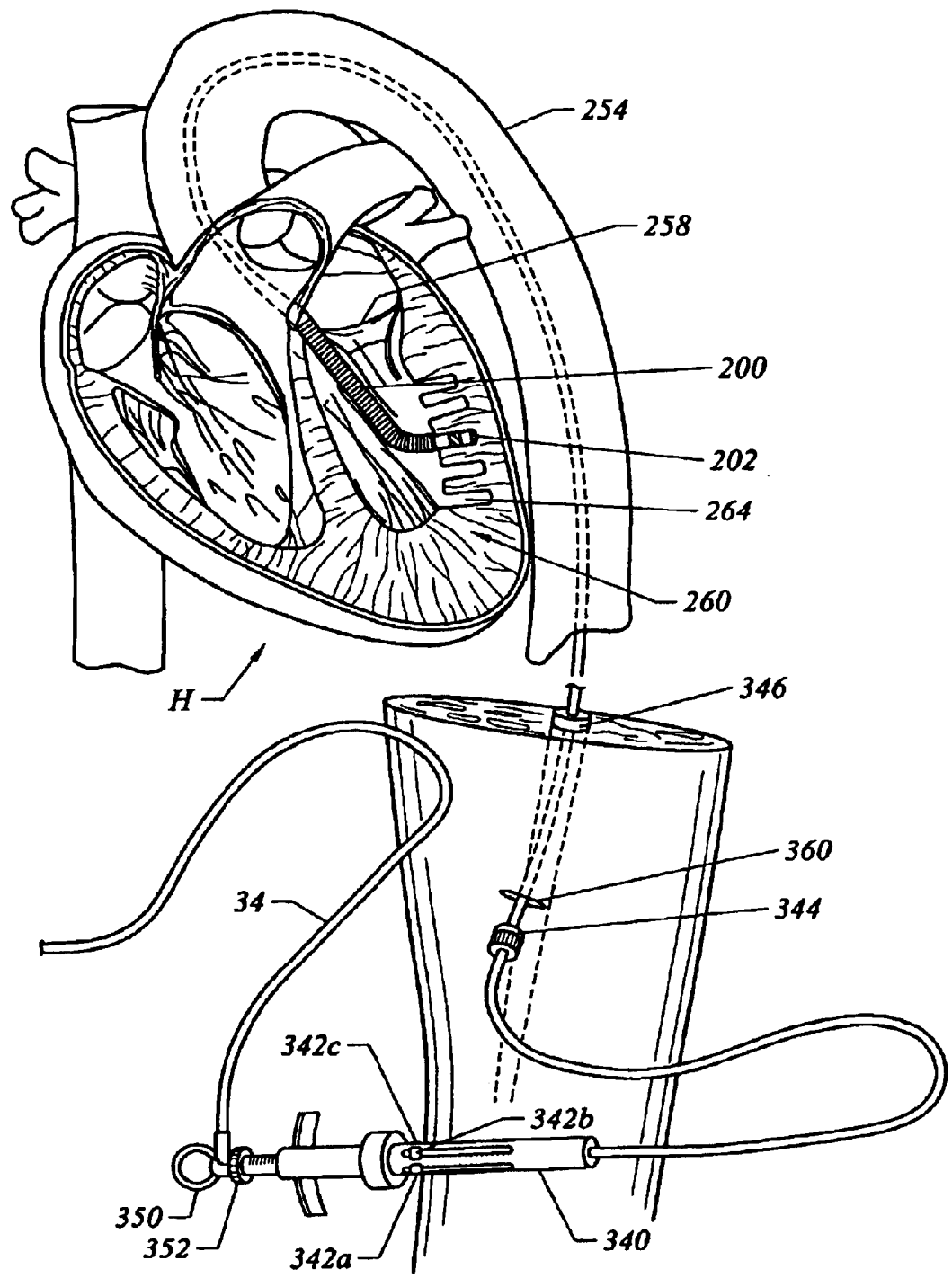
FIG. 11 is a sectional view of the human heart, illustrating the electrosurgical catheter of FIG. 5 within the ventricular cavity for performing a transmyocardial revascularization procedure.

As shown in FIG. 11, electrosurgical probe 202 is positioned into the left ventricular cavity 258 of the heart. Electrosurgical probe 202 may be introduced into the left ventricle 258 in a variety of procedures that are well known in the art, such as a percutaneous, minimally invasive procedure. In the representative embodiment, probe 202 is introduced into the vasculature of the patient through a percutaneous penetration 360 and axially translated via delivery catheter 200 through one of the major vessels, such as the femoral artery 346, through the aorta 254 to the left ventricular cavity 258. A viewing scope (not shown) may also be introduced through a percutaneous position to a position suitable for viewing the target location in the left ventricle 258.

Figure 13:
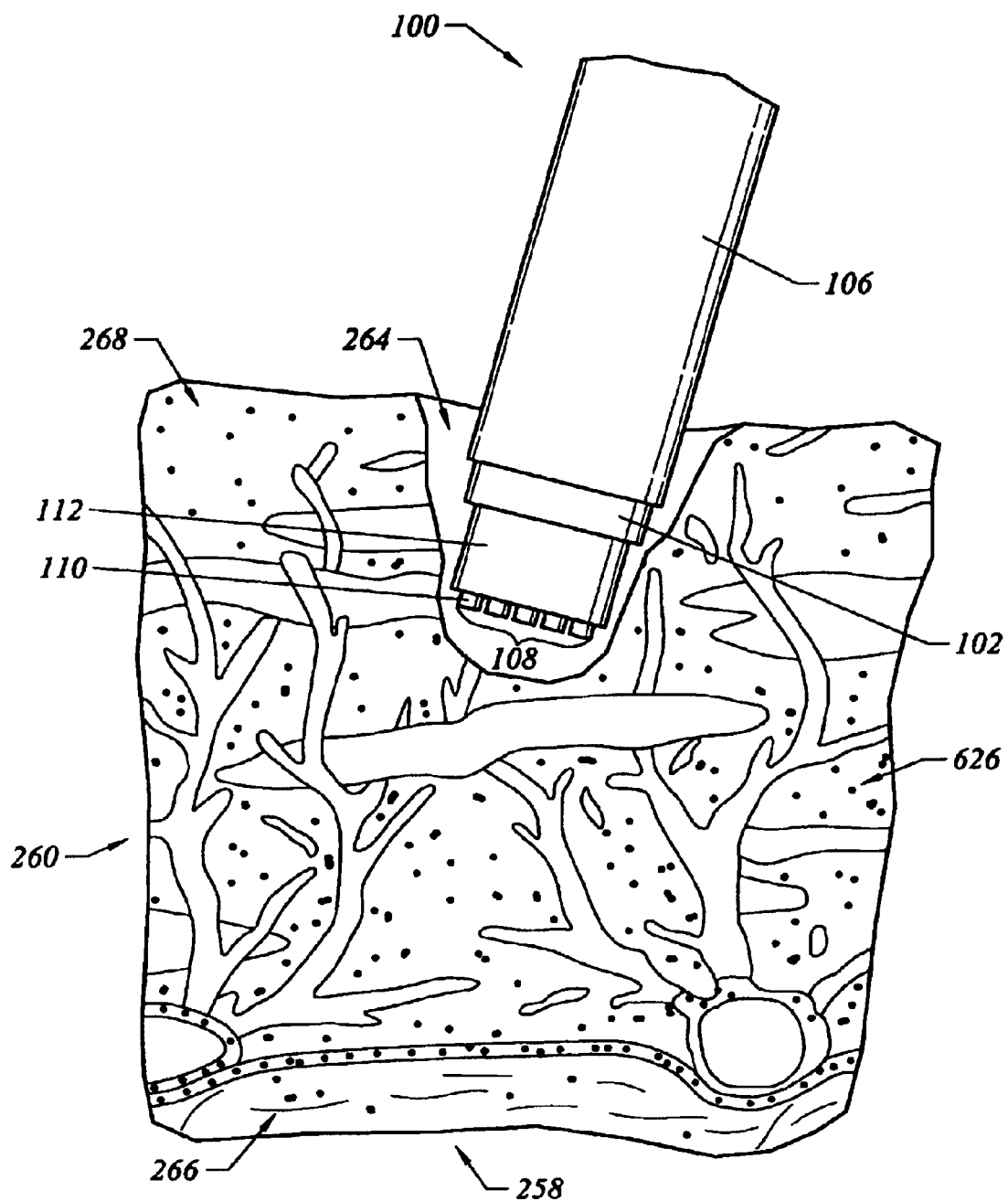
FIG. 13 is a cross-sectional view of the probe of FIGS. 3, 4A and 4B boring a channel through the myocardium.
Figure 14:
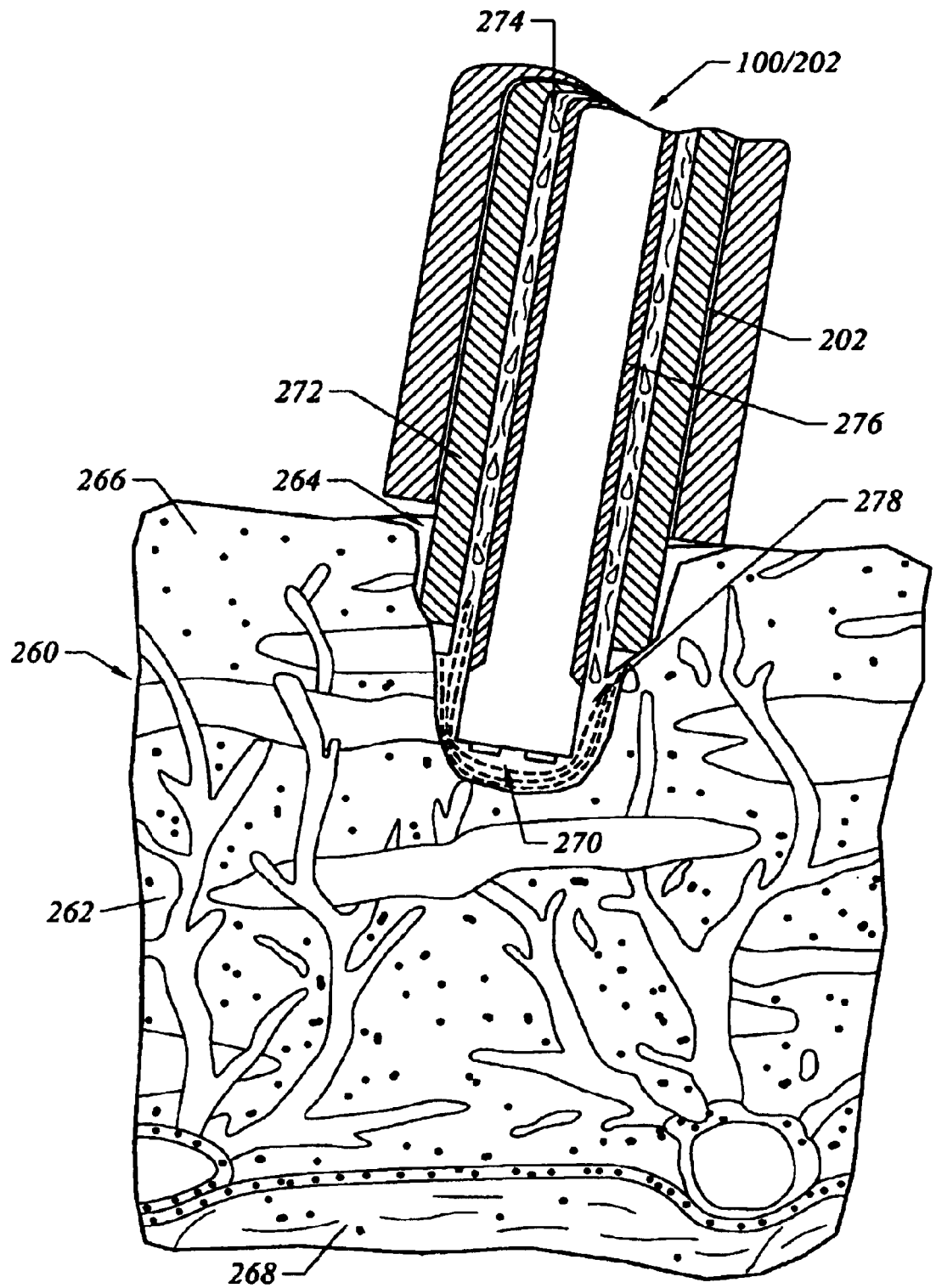
FIG. 14 is a cross-sectional view of the probe of FIG. 1 boring a channel through the myocardium.

Once positioned within the patient's ventricle 258, probe 202 is aligned with the heart wall 260 to form one or more artificial channels 264 for increasing blood flow to the myocardium 262 (e.g., FIG. 13). As shown in FIG. 14, the channels 264 will preferably extend from the endocardium 266 a desired distance through the myocardium 262, without perforating the exterior of the epicardium 268. Preferably, the surgeon will employ a detection or instrument guidance system 350, (discussed below in reference to FIGS. 16, 18, 19, and 20) on probe 202, or another instrument, to determine the location of the probe within the myocardium relative to the epicardium 268. The location of channels 264 may be selected based on familiar endocardial anatomic landmarks. Alternatively, instrument guide system 350 may be used to select target sites on the heart wall, as discussed below.

As shown in FIG. 14, guide catheter 200 is positioned adjacent the inner endocardial wall and probe 202 is axially translated so that the active electrode 270 at its distal end is positioned proximate the heart tissue. In this embodiment, the probe 202 includes a single, annular electrode 270 at its distal tip for ablation of the heart tissue. However, it will be readily recognized that the probe may include an array of active electrodes as described in detail above. While viewing the region with an endoscope (not shown), voltage can be applied from power supply 28 (see FIG. 1) between active electrode 270 and annular return electrode 272. The boring of channel 264 is achieved by engaging active electrode 270 against the heart tissue or positioning active electrode 270 in close proximity to the heart tissue while simultaneously applying voltage from power supply 28 and axially displacing probe 202 through channel 264. To complete the current path between the active electrode 270 and return electrode 272, electrically conductive irrigant (e.g., isotonic saline) will preferably be delivered from fluid supply 21 to the target site via annular fluid path 274, the latter located external to return electrode 272 and tubular shaft 200. Alternatively, the site may already be submerged in fluid, or the fluid may be delivered through a separate instrument. The electrically conductive fluid provides a pathway for electrical current flow between the heart tissue and return electrode 272, as illustrated by the current flux lines 278 in FIG. 15.

Figure 15:
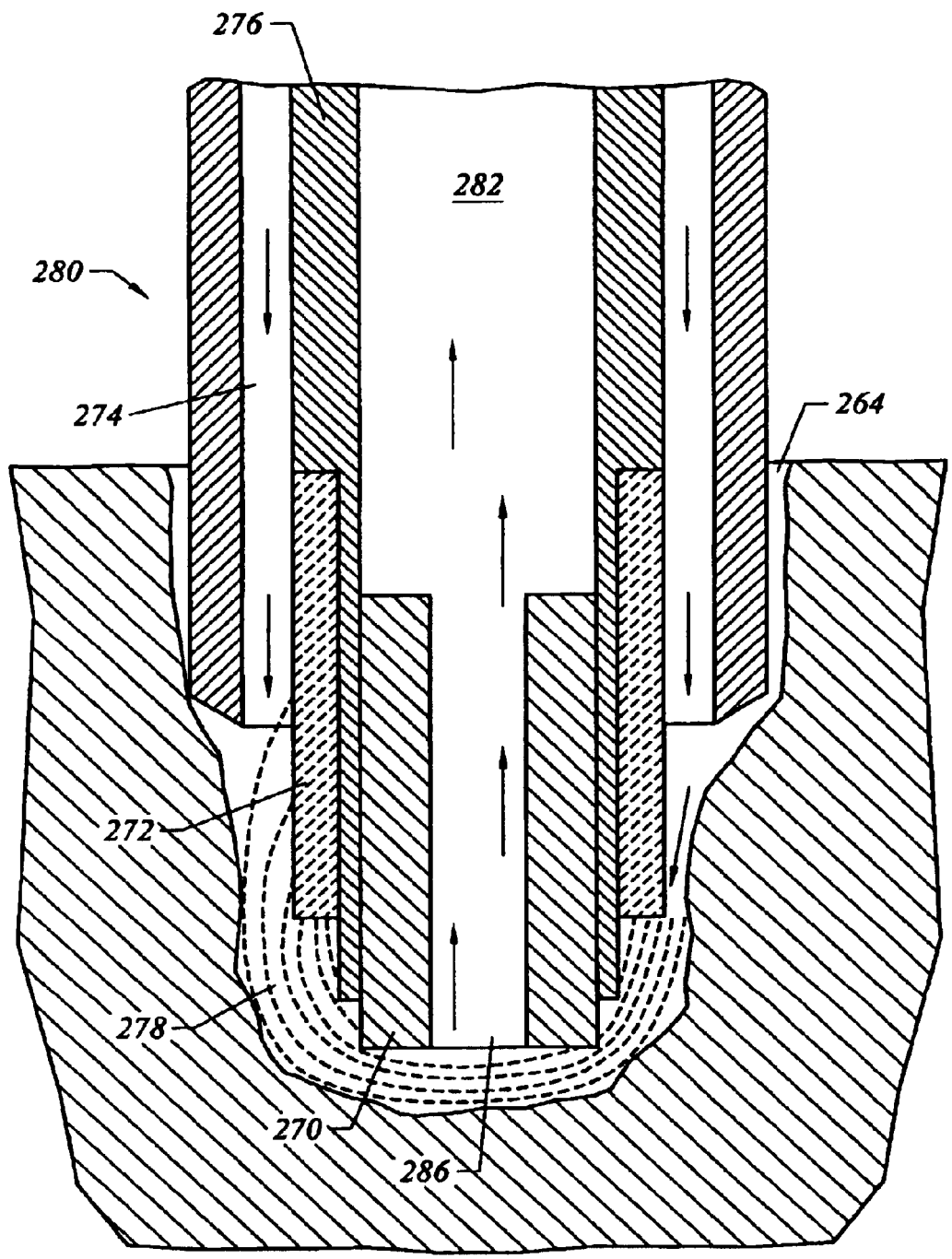
FIG. 15 depicts an alternative embodiment of the probe of FIG. 14 having an outer lumen for delivering electrically conductive fluid to the target site, and an inner lumen for aspirating fluid and gases from the transmyocardial channel.

FIG. 15 illustrates an alternative embodiment of a probe for use in conjunction with catheter 200. In this embodiment, the probe 280 includes a central lumen 282 having a proximal end attached to a suitable vacuum source (not shown) and an open distal end 286 for aspirating the target site. To complete the current path between the active electrode 270 and return electrode 272, electrically conductive irrigant (e.g., isotonic saline) will preferably be delivered from fluid supply 21 (shown in FIG. 1) through annular fluid path 274 between return electrode 272 and tubular shaft 200 to the target site. The active electrode is preferably a single annular electrode 270 surrounding the open distal end 286 of central lumen 282. Central lumen 282 is utilized to aspirate or otherwise remove the ablation by-products (e.g., fluids and gases) generated at the target site and excess electrically conductive irrigant during the procedure.

Figure 23:
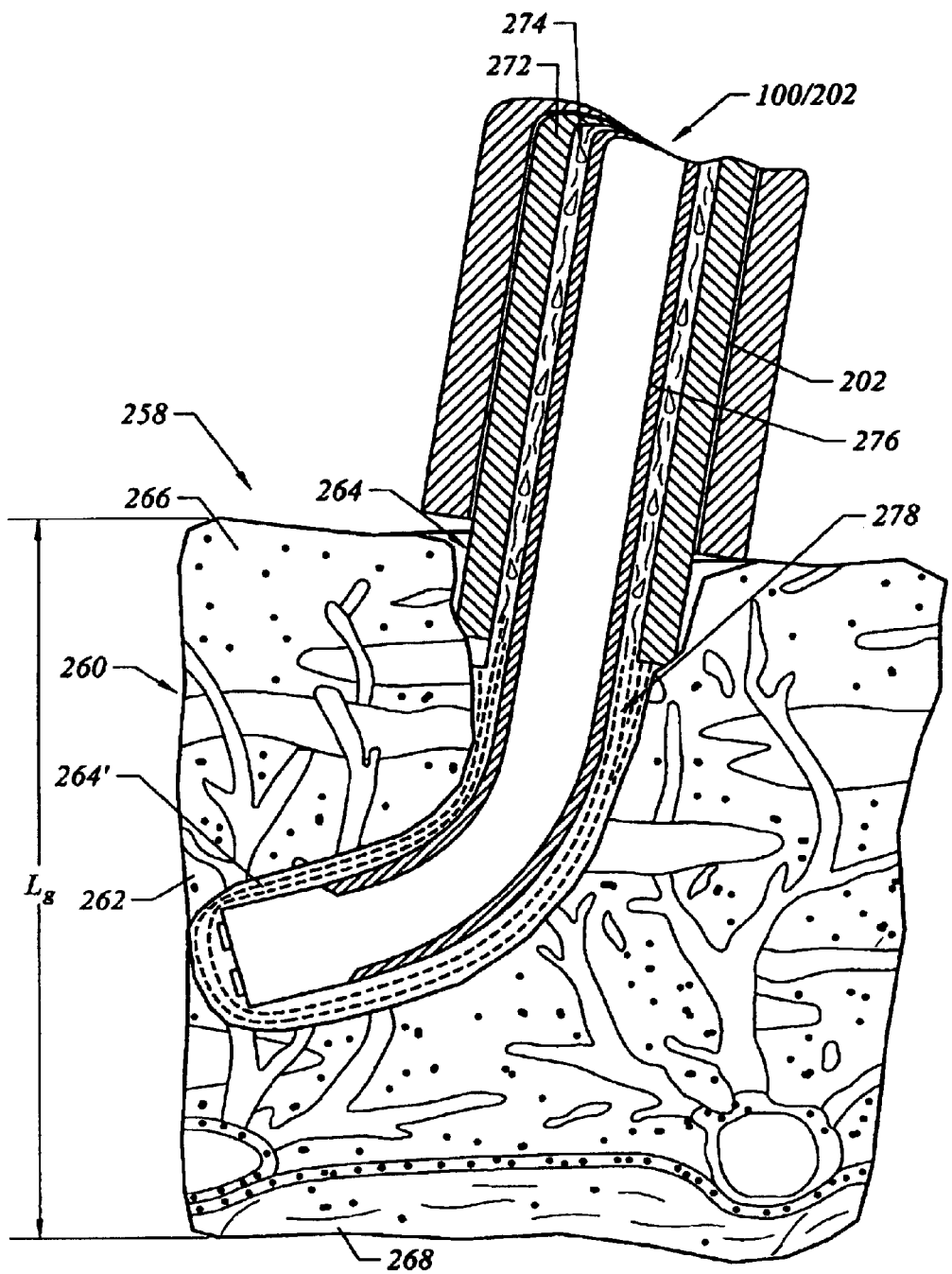
FIG. 23 schematically illustrates a curved revascularizing channel formed by one of the electrosurgical instruments of the present invention.

An alternative embodiment of the percutaneous, endocardial canalization approach is shown in FIG. 23. In this embodiment, electrosurgical instrument 100/catheter 200 can be guided by the surgeon or surgical assistant during the canalization of channel 264 using external handpiece 340 (FIG. 11). In this embodiment, the distal portion of the electrosurgical catheter 200/probe 202 can be caused to follow a curved path to effect a curved artificial channel 264'. By forming a curved artificial channel 264', the total surface area of the artificial channel can be extended so that the channel is longer than the total thickness L9 of the heart wall 260. In addition, by forming a curved artificial channel 264' of proper curvature as shown in FIG. 23, the penetration of the epicardium 268 can be avoided. Still further, the curved artificial channel 264' can be continued forming a complete "U" shaped channel which reenters the ventricular cavity 258 providing one continuous channel which penetrates the endocardium at two locations but does not penetrate through the epicardium 268.

Figure 12:
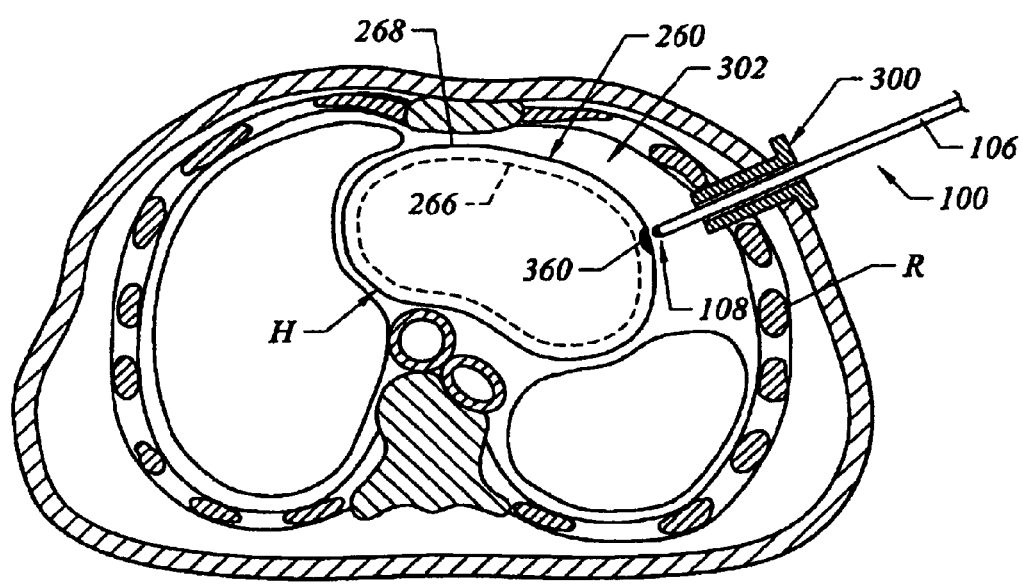
FIG. 12 is a sectional view of the thoracic cavity, illustrating the electrosurgical probe of FIGS. 3, 4A and 4B in a thoracoscopic revascularization procedure.

FIG. 12 illustrates a thoracoscopic procedure for revascularizing the myocardium from the outer wall or epicardium 268 inward to the endocardium 266. At least one intercostal penetration is made in the patient for introduction of electrosurgical probe 100 (FIG. 3) into the thoracic cavity 302. The term "intercostal penetration" as used herein refers to any penetration between the ribs of a patient. Typically, such a penetration is in the form of a small cut, incision, hole or cannula, trocar sleeve or the like, through the chest wall between two adjacent ribs. Usually, such a penetration does not require cutting, removing, or significantly displacing or retracting the ribs or sternum. Usually, the intercostal penetration will require a puncture or incision of less than about 5 cm in length. In one embodiment, the intercostal penetration may be via a trocar sleeve 300 having a length in the range from about 2 cm to 15 cm, and an internal diameter in the range from 1 mm to 15 mm, commonly known as thoracic trocars. Suitable trocar sleeves are available, for example, from United States Surgical Corp. of Norwalk, Conn., under the brand name "Thoracoport"TM. A viewing scope (not shown) may also be introduced through a trocar sleeve to a position suitable for viewing the target location on the heart wall 260. A viewing scope (not shown) may also be introduced through the same or another intercostal penetration into the thoracic cavity 302 to a position suitable for viewing the target location 360 on the surface of the epicardium 268 of the heart. The viewing scope can be a conventional laparoscope or thoracoscope, which typically comprise a rigid elongated tube containing a lens system and an eyepiece or camera mount at the proximal end of the tube. A small video camera is preferably attached to the camera mount and connected to a video monitor to provide a video image of the procedure. This type of scope is commercially available, for example, from Baxter Healthcare Corporation of Deerfield, Ill., or from United States Surgical Corporation of Norwalk, Conn.

As shown in FIGS. 12 and 13, one or more artificial channels 264 are formed by the electrosurgical probe 100 from the outer wall or epicardium 268 through the myocardium 262 and the inner wall or endocardium 266 into the ventricular cavity 258. Similar to the above described method, electrode array 108 is positioned in close proximity to the heart tissue while simultaneously applying voltage from power supply 28 and axially displacing probe 100 through channel 264. In this embodiment, however, electrically conductive fluid is not supplied to the target site to complete the current path between the active electrodes 110 and return electrode 102. Applicant has found that the fluids in the patient's heart tissue, such as blood, usually have a sufficient amount of electrical conductivity to complete the electrical path between the active electrode array and the return electrodes. In addition, these fluids will often have the requisite properties discussed above for establishing a vapor layer and inducing the discharge of energetic electrons and photons from the vapor layer to the surface of the target tissue, as well as the creation of high electric fields to effect the ablation of tissue.

To inhibit blood from flowing through channels 264 into the thoracic cavity, the channels 264 will preferably be sealed at the epicardium 268 as soon as possible after they have been formed. One method for sealing the artificial channel 264 at the epicardium 268 is to insert a collagen hemostasis device 480 (shown in FIG. 21) using a trocar 300, a cannula 484 and a syringe-like delivery system 486. The collagen, unaffected by antiplatelet or anticoagulant agents that may be present in the patient's blood stream, attracts and activates platelets from the blood 482, rapidly forming a "glue"-like plug near the surface of the epicardium 268 of the newly formed channel 264. Suitable collagen hemostasis devices are available from, for example, Datascope Corporation, Montval, N.J. under the brand name "VasoSeal™". The deployment of the collagen hemostasis device 480 is accomplished with the aid of a viewing scope (not shown) which may also be introduced through a trocar sleeve to a position suitable for viewing the target location on the heart wall 260.

To facilitate this sealing procedure, an electrosurgical probe (e.g., probe 354, FIG. 16) will preferably include a guidance system 350 for determining when the probe is close to the inner surface of the endocardium 266, so that the surgeon can prepare to withdraw the probe and seal the channel 264.

In both of the above embodiments, the present invention provides localized ablation or disintegration of heart tissue to form a revascularization channel 264 of controlled diameter and depth. Usually, the diameter will be in the range of from about 0.5 mm to 3 mm, preferably from about 1 mm to 2 mm. Preferably, the radio frequency voltage will be in the range of 300 volts to 2400 volts peak-to-peak to provide controlled rates of tissue ablation and hemostasis while minimizing the depth of necrosis of tissue surrounding the desired channel. This voltage will typically be applied continuously throughout the procedure until the desired length of the channel 264 is completely formed. However, the heartbeat may be monitored and the voltage applied in pulses that are suitably timed with the contractions (systole) of the heart.

Ablation of the tissue may be facilitated by axially reciprocating and/or rotating the electrosurgical probe a distance of between about 1 mm to 5 mm. This axial reciprocation or rotation allows the electrically conductive fluid (FIG. 14) to flow over the tissue surface being canalized, thereby cooling this tissue and preventing significant thermal damage to the surrounding tissue cells.

Figure 16:
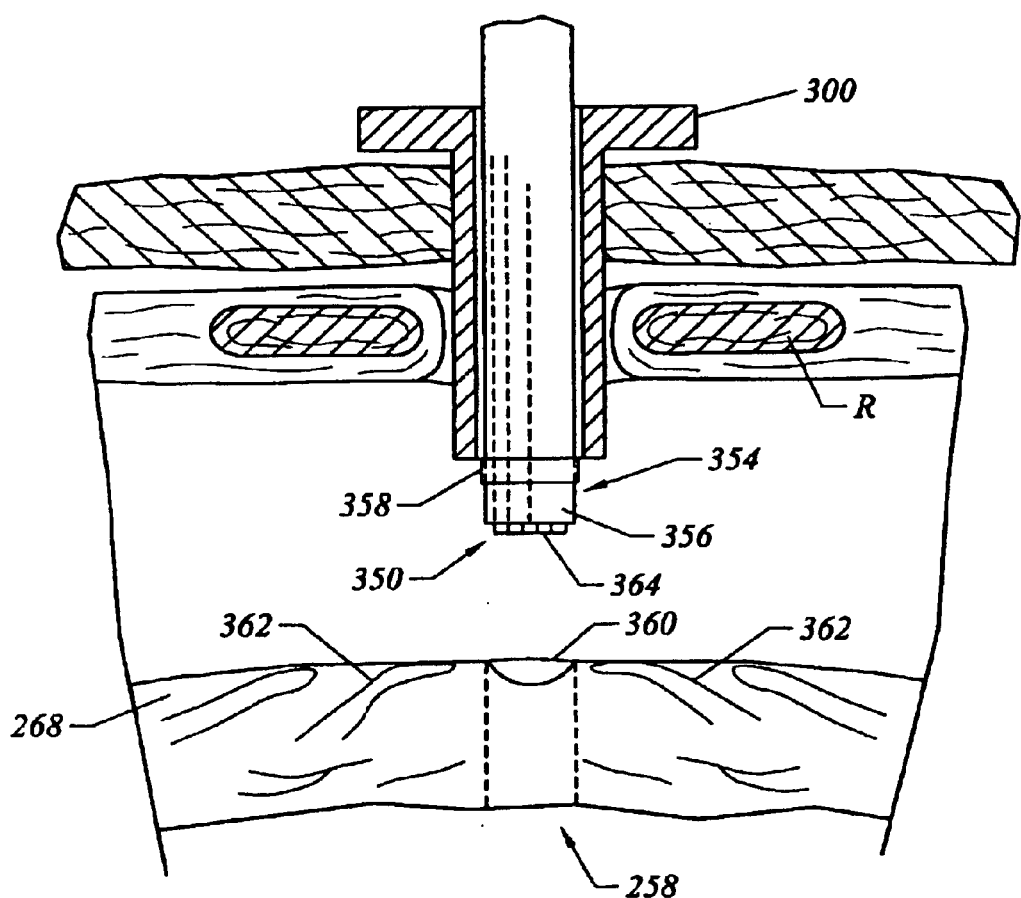
FIG. 16 is a side view of an electrosurgical probe incorporating a fiberoptic viewing device and a light generator for sighting the probe onto a target site on the heart tissue.

FIG. 16 illustrates one representative guidance system 350 for guiding an electrosurgical probe 354 to target sites on the heart wall. Guidance system 350 is provided for detecting an "end point" for each artificial channel and/or for determining appropriate target sites on the heart wall for forming the artificial channels. The instrument guidance system 350 will preferably allow a surgeon to determine when the electrosurgical probe 354 (or an electrosurgical catheter) is near the other end of the heart wall (i.e., the outer edge of the epicardium or the inner edge of the endocardium). The guidance system 350 indicates to the surgeon to stop axially translating the probe 354 so that the probe does not form a channel completely through a heart wall, which limits bleeding and/or reduces damage to surrounding tissue structures or blood. Alternatively or in addition, the guidance system 354 can allow the surgeon to determine an appropriate target site 360 on the heart wall at which to form the channel to avoid accidental puncturing of relatively large vessels in the heart wall.

In the embodiment shown in FIG. 16, the instrument guidance system 350 includes a fiberoptic viewing cable 356 within electrosurgical probe 354, and a visible light generator 358, such as a laser beam, integral with the probe, for illuminating a target site 360 on the heart wall. Note that both light generator 358 and fiberoptic cable 356 may be coupled to an instrument other than probe 354. The fiberoptic viewing cable 356 sites the target site 360 illuminated by the visible light generator 358 to locate where the probe 354 can bore the hole. This allows the surgeon to avoid puncturing larger blood vessels 362 on the heart wall (e.g., coronary arteries or veins). Visible light generator 358 may also be used to determine when the distal end 364 of probe 354 is close to the opposite side of the heart wall, or when the probe 354 has completely penetrated through the heart wall into, or out of, the ventricular cavity 258.

In a second embodiment, the detection system can be an ultrasound guidance system that transmits sound waves onto the heart wall to facilitate canalization of the heart.

Figure 18:
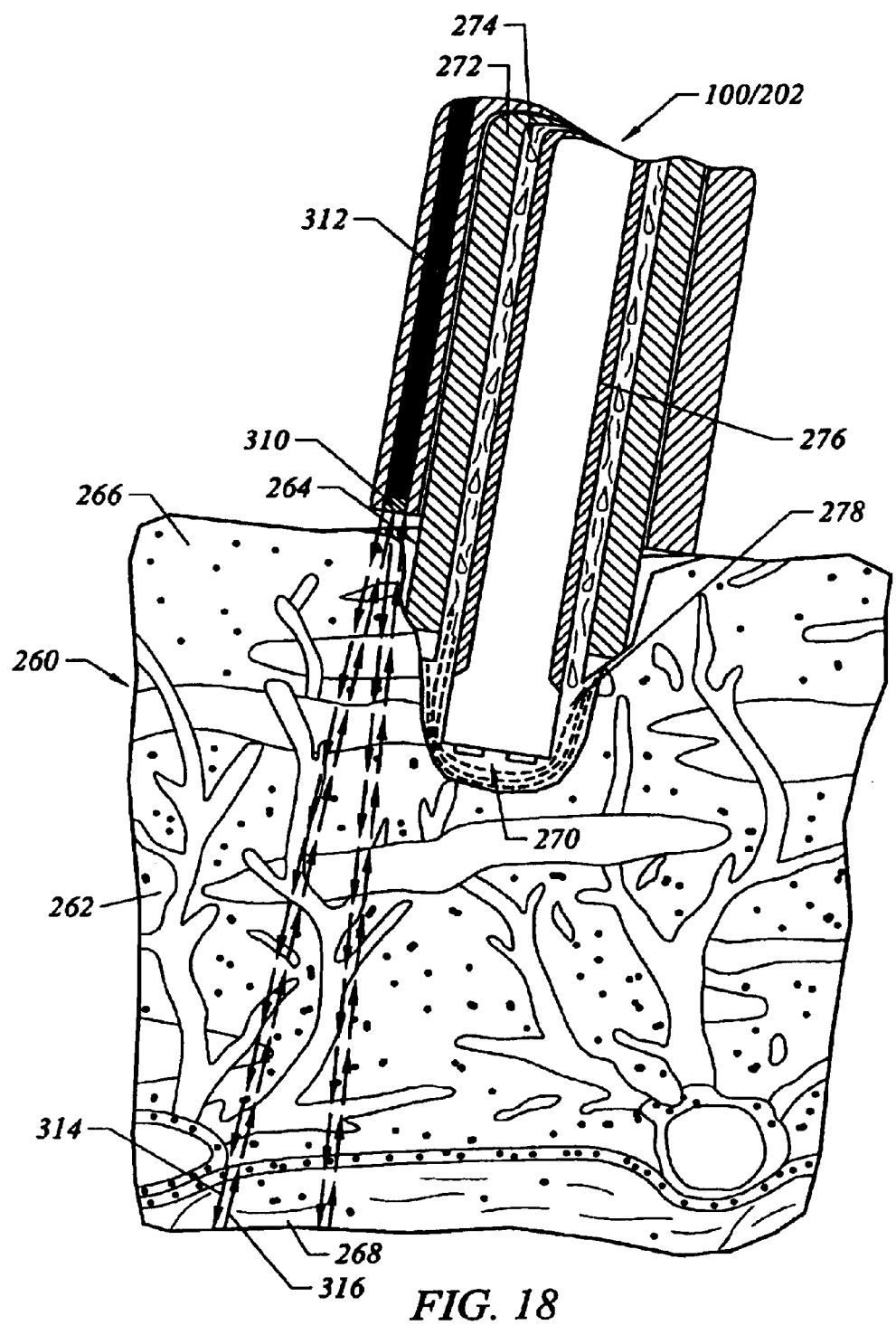
FIG. 18 is a cross-sectional view of the probe of FIG. 1 boring a channel into the myocardium with an ultrasound tissue thickness measuring device located on a guide catheter.
Figure 19:
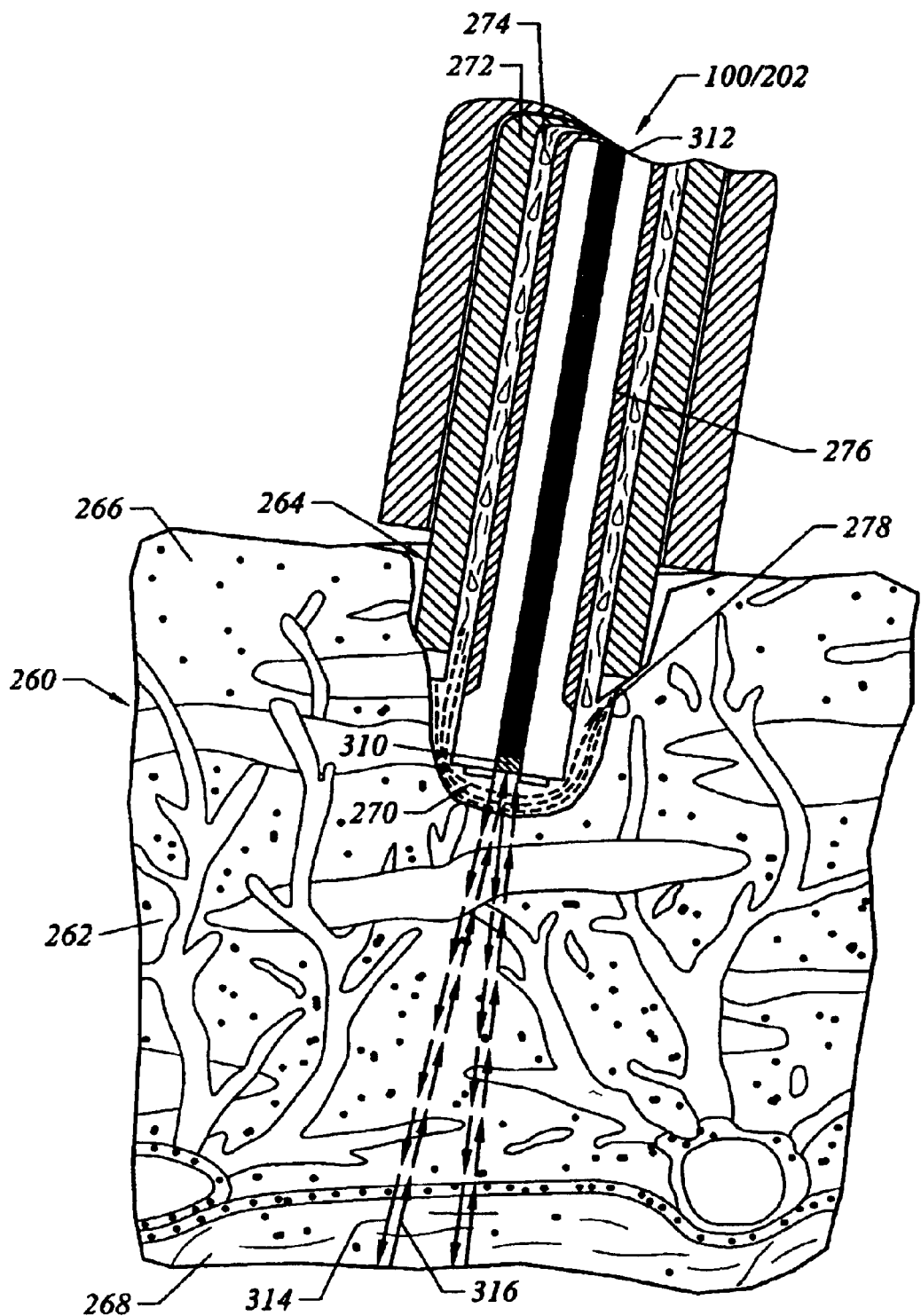
FIG. 19 is a cross-sectional view of the probe of FIG. 1 boring a channel into the myocardium with an ultrasound tissue thickness measuring device located on an electrosurgical catheter.

Referring to FIGS. 18 and 19, an ultrasound tissue thickness measuring system may be incorporated within an electrosurgical instrument of the invention, e.g., probe 100 or catheter 200, to measure the thickness of the heart wall 260 adjacent to active electrode 270, and thereby allow the surgeon to pre-set the depth of each channel using adjustable stop 352 on handpiece 340 (FIG. 11) before energizing catheter 200/probe 100 and ablating the heart tissue. In the embodiment shown in FIG. 18, an ultrasonic transducer 310, affixed to the distal end of the instrument, and connected to an external ultrasonic generator and sensing system (not shown) via lead 312, transmits pulses of ultrasound into the heart tissue in the form of emitted ultrasound signal 314, and the ultrasound generator and sensing system measures the delay time for reflected ultrasound signal 316 to return from the boundary of the heart wall at the surface of epicardium 268 to the sensing system. This delay time can be translated into a thickness of the entire heart wall and allow the surgeon to adjust the maximum travel distance of catheter 200/probe 100 using mechanical stop 352 (FIG. 11) to prevent the length of channel 264 from extending through the outer surface of the epicardium 268. The surgeon can choose to stop the canalization of the heart at any selected distance of the epicardium which may typically be in the range from about 1 mm to 10 mm.

A third embodiment is shown in FIG. 19 wherein an ultrasonic transducer 310 is affixed to the distal end of electrosurgical catheter 200/probe 100, and connected to an external ultrasonic generator and sensing system (not shown) via leads 312, and transmits pulses of ultrasound into the heart tissue in the form of emitted ultrasound signal 314. The ultrasound generator and sensing system measures the delay time for reflected ultrasound signal 316 to return from the boundary of the heart wall at the surface of epicardium 268 to the sensing system. This measured delay time can be translated into the distance between active electrode 270 and the surface of the epicardium 268. In this arrangement, the surgeon can observe where the channel 264 reaches the preferred distance from the epicardium 268, and can interrupt the application of power and advancement of catheter 200/probe 100. In one embodiment, the preferred minimum thickness of the uncanalized heart wall 260 (i.e., the minimum distance from the bottom of channel 264 to the surface of the epicardium 268) can be preselected by the surgeon. When this distance is reached based on the thickness of the uncanalized heart wall measured using the ultrasonic generator and sensor system, the ultrasonic generator and sensor system provides an electrical signal to the power source to interrupt the voltage applied to catheter 200/probe 100, thereby ending the canalization process and limiting the depth of channel formed. In this manner, the surgeon may hear an audible tone and will "feel" the catheter advancement stop at the moment the applied voltage is interrupted.

Figure 20:
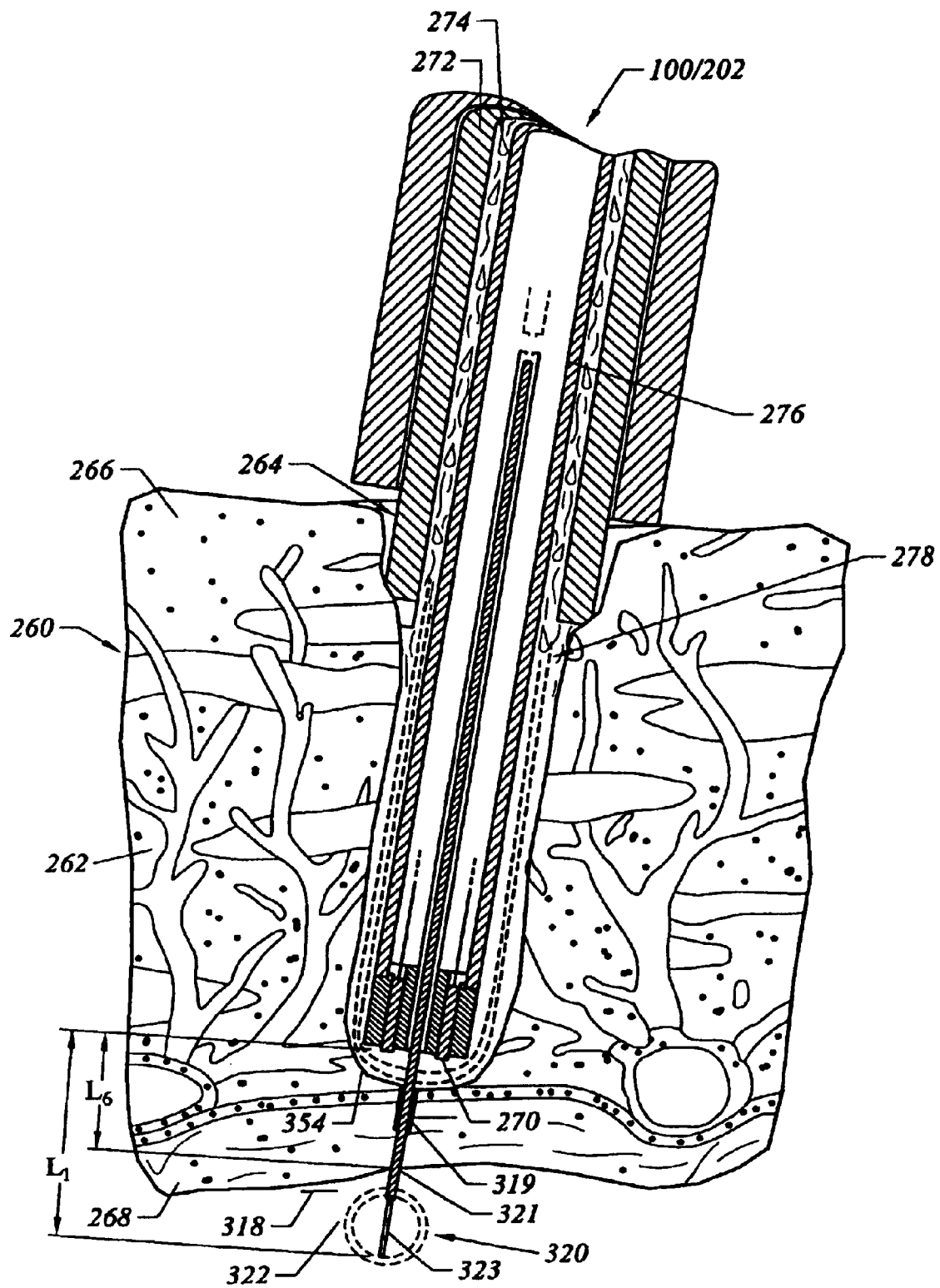
FIG. 20 is a cross-sectional view of the probe of FIG. 1 boring a channel into the myocardium with an electrical impedance sensor located on an electrosurgical catheter, to detect crossing through a surface of the heart, at a distance L1 distal to the electrode array.

A fourth embodiment is shown in FIG. 20, in which an electrosurgical instrument, e.g., probe 100/202 includes a small diameter tissue electrical impedance measurement sensor 319 which extends distally from active electrode(s) 270 by a distance L1. Impedance measurement sensor 319 detects the outer surface of the epicardium 268 as sensor 319 enters a region of different electrical impedance (viz, the fluid-filled cavity surrounding the heart). In the present embodiment, a sensor tip 320 may include a first impedance measurement electrode 321 and a second impedance measurement electrode 323. A small, high-frequency potential is applied between first and second impedance measurement electrodes 321 and 323 causing current flow between first and second impedance measurement electrodes 321 and 323 as indicated by current flux lines 322. As the first and second electrodes 321 and 323 emerge from the epicardium 268 into cavity 318 surrounding the heart, the change in electrical impedance is measured, and may be indicated by an audible signal and/or may be used as a direct feedback control signal to interrupt the application of voltage to the electrosurgical catheter 100 by generator or power supply 28 (FIG. 1). By this method, the forward advancement of the electrosurgical catheter 100 can be limited to a pre-selected distance L6 between the bottom of channel 264 and the surface of the epicardium 268.

In a fifth embodiment shown in FIG. 13, a guidance system utilizes impedance measurement circuitry integrated with active electrodes 110 to detect when probe 100 is adjacent blood vessels and/or the outer or inner boundaries of the heart wall. Specifically, the current limiting circuitry includes a number of impedance monitors coupled to each active electrode 110 to determine the impedance between the individual active electrode 110 and the return electrode 102. Thus, for example, if the measured impedance suddenly decreases at active electrodes 110 at the tip of the probe 100, the applied voltage will be interrupted to avoid power delivery to blood filled ventricular cavity 258 of the heart, thereby avoiding formation of a thrombus or damage to other tissue structures within the ventricular cavity 258.

Figure 17:
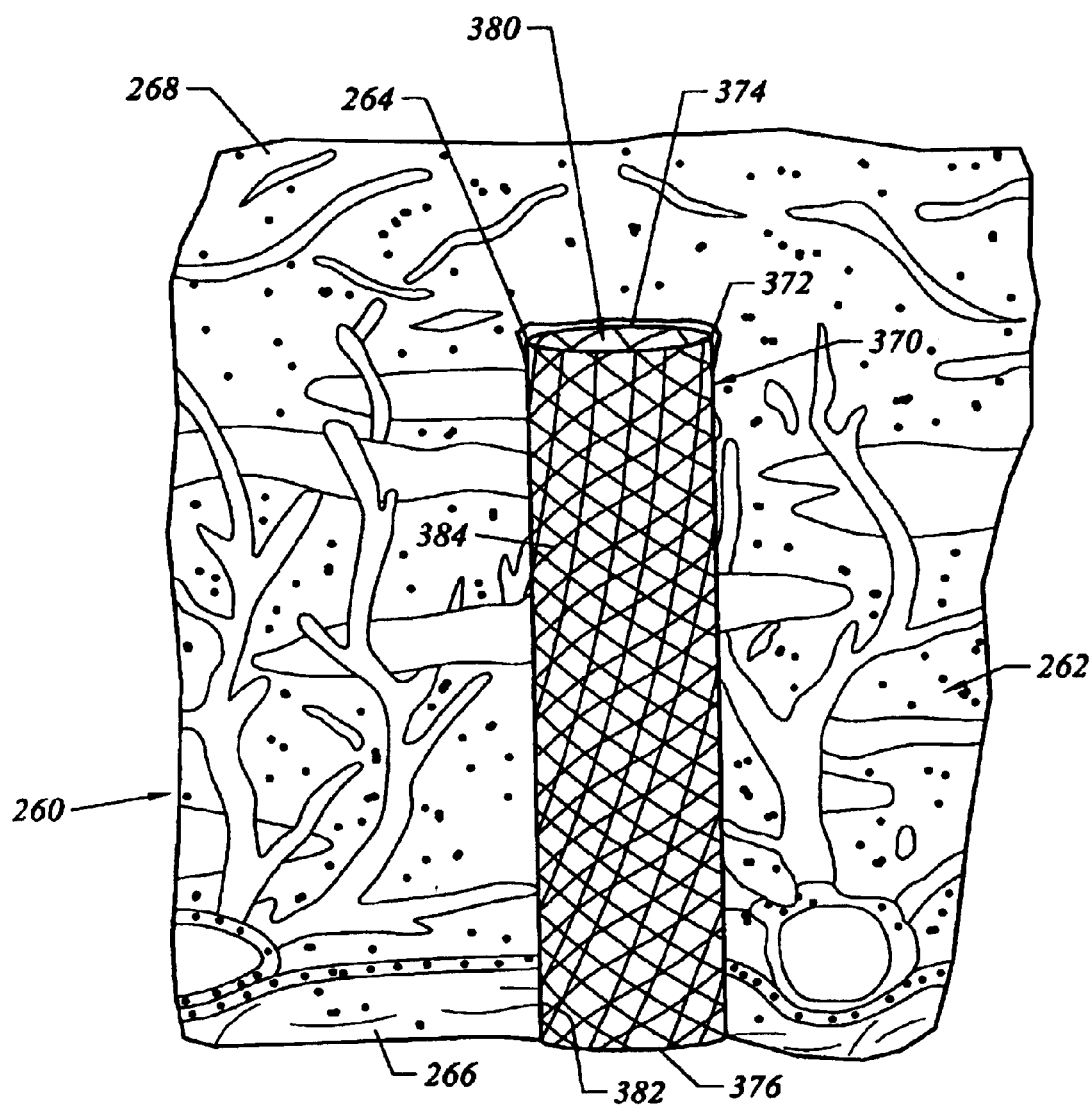
FIG. 17 schematically illustrates a lumenal prosthesis positioned in a revascularizing channel during a percutaneous procedure to maintain lumen patency.

FIG. 17 illustrates a method for implanting a luminal prosthesis, such as a stent or stent-graft 370, into the artificial channels 264 formed by one of the electrosurgical probes or catheters of the present invention to maintain the patency of these channels 264. The stents 370 are usually compressed into a narrow-diameter configuration (not shown), and advanced endoluminally to one of the artificial channels 264 in the heart wall with a conventional or specialized delivery catheter (not shown). Alternatively, the electrosurgical probe may be designed to deliver and implant the stents 370 at the target site. The stents 370 will typically comprise a resilient, radially compressible, tubular frame 372 having a proximal end 374, a distal end 376, and an axial lumen 380 therebetween. The tubular frame 372 includes a plurality of openings or slots (not shown) that allow frame 272 to be expanded radially outward into the enlarged configuration shown in FIG. 17 by conventional methods, such as shape memory alloys, expandable balloons, and the like. The stent 370 exerts a radial force against the inner channel walls 382 to maintain lumen patency and/or mechanically augment luminal wall strength, thereby maintaining the blood flow from the ventricular cavity to the myocardium. The stent 370 may also include a graft or liner 384 for inhibiting cell proliferation and occlusion through the openings and slots of frame 372.

In a first embodiment shown in FIG. 17, the stent 370 is introduced into the artificial channel 264 during a percutaneous procedure as illustrated in FIG. 11. In this embodiment, the length of each channel 264 and hence the length of each stent 370 extends only partially through the entire thickness of heart wall 260.

Figure 21:
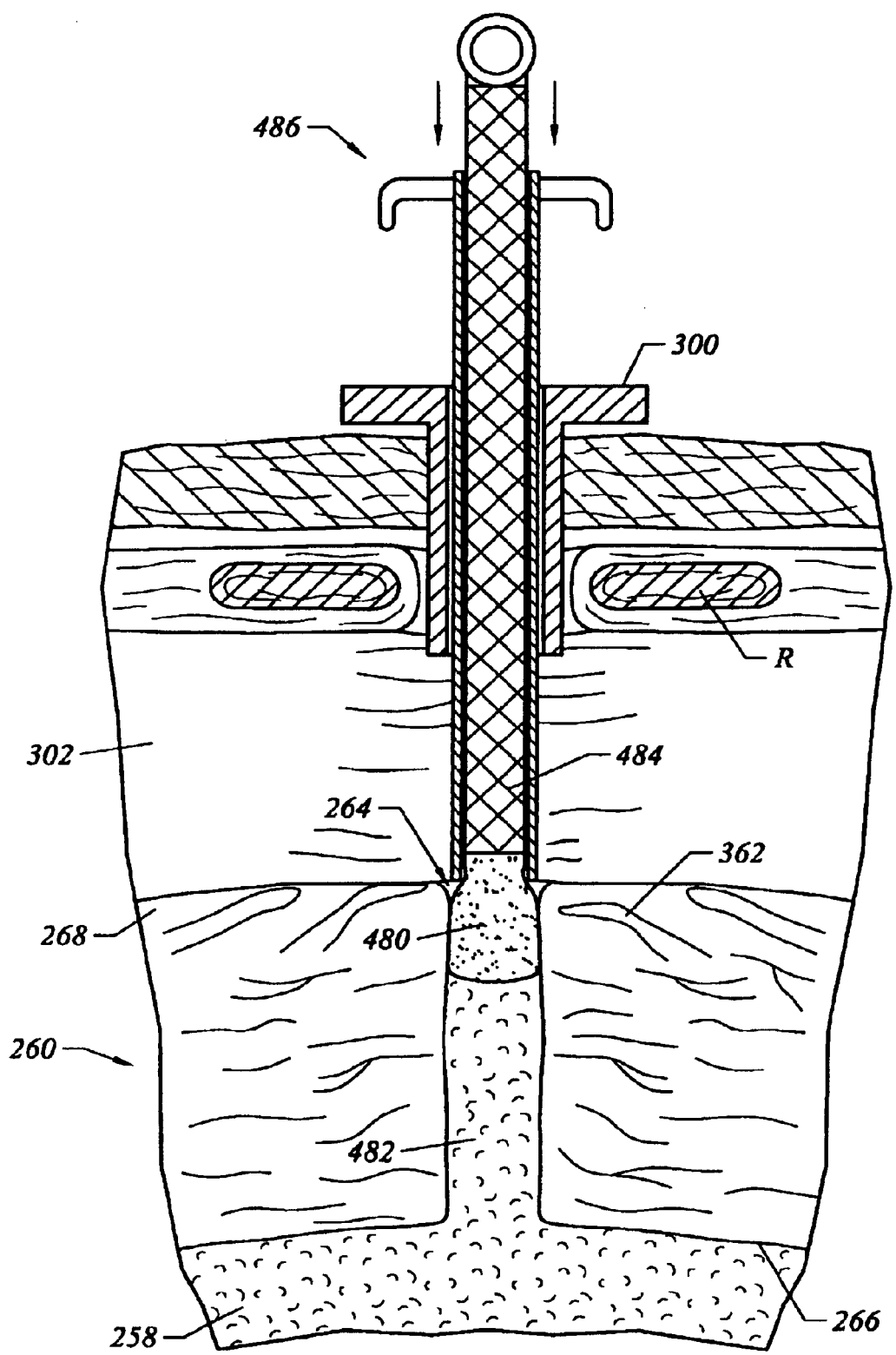
FIG. 21 is a schematic cross-sectional view of a hemostasis device for sealing artificial revascularizing channels formed by one of the electrosurgical instruments of the present invention.
Figure 22:
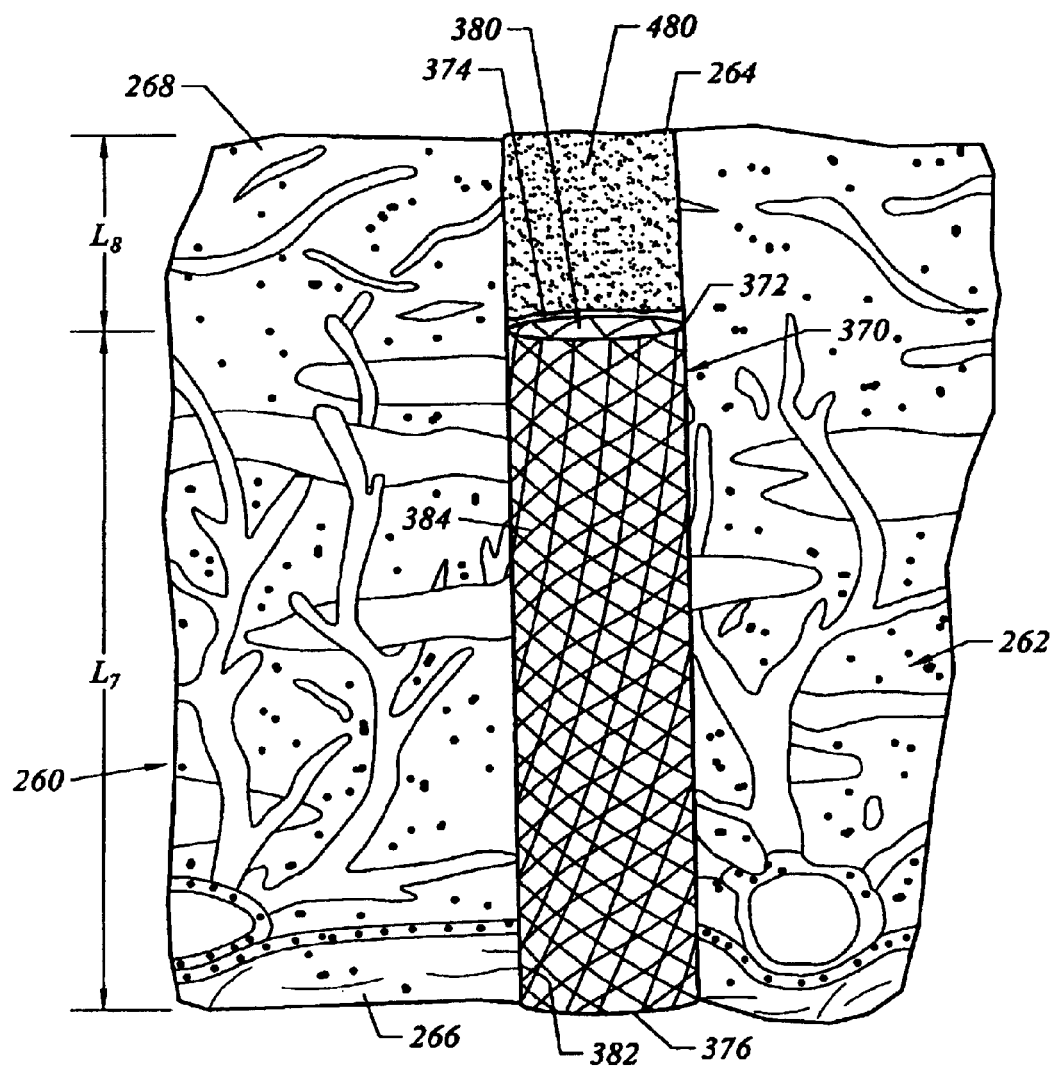
FIG. 22 schematically illustrates a lumenal prosthesis positioned in a revascularizing channel during a thoracoscopic procedure to maintain lumen patency.

In a second embodiment shown in FIG. 22, the stent is introduced into the artificial channel 264 during a thoracoscopic procedure as illustrated in FIG. 12. In this embodiment, the length of each artificial channel 264 may extend completely through the heart wall 260. However, in this embodiment, the stent 370 is placed in the distal portion of the artificial channel 264 as shown in FIG. 22 extending to the endocardium 266 to maintain patency of the artificial channel 264 over length L7 of heart wall 260. Following insertion and deployment of stent 370, the proximal portion of artificial channel 264 may be sealed using collagen hemostasis device 480, or the like, and syringe-like delivery system 486, as described hereinabove with reference to FIG. 21. The collagen hemostasis device 480 attracts and activates platelets from the blood 482, rapidly forming a "glue"-like plug near the surface of the epicardium 268 of the newly formed artificial channel 264. Alternatively, a collagen hemostasis device may be deployed through a central lumen integral with the electrosurgical probe or catheter (e.g., lumen 59, FIG. 2A). The collagen hemostasis device can be compressed to fit within a lumen 59 whose diameter is smaller than that of the artificial channel 264. When ejected form the confining lumen 59, the collagen hemostasis device 480 expands to fill the full diameter of the artificial channel 264 over length L8 as shown in FIG. 22. Also, such a system for the deployment of a collagen hemostasis device 480 or the like may be integrated with probe 100/catheter 200 used for the percutaneous canalization of artificial channels 264 according to the method illustrated in FIG. 11. Referring to FIGS. 2A, 11, and 22, in a percutaneous approach using this sealing method, the artificial channel 264 would be formed through the entire thickness of the heart wall 260. Once the surface of the epicardium 268 is penetrated, probe 202 of catheter 200 is retracted a distance L8. Next, a collagen hemostasis device 480, or the like, is deployed to fill channel 264 over length L8 (FIG. 22). When ejected from the confining lumen 59, collagen hemostasis device 480 expands to fill the full diameter of the artificial channel 264 over length L8 as shown in FIG. 22 to effect a seal which prevents blood loss through the opening in the epicardium 268. Alternatively, suturing techniques may be employed, either percutaneously, thoracoscopically, or in an open chest procedure, to seal the opening of the artificial channels at the surface of the epicardium 268.

The stent frame 372 of the present invention is typically manufactured from a tubular member, such as tubing made out of shape memory alloy having elastic or pseudo-elastic properties, such as Nitinol™, Elgiloy™, or the like. Alternatively, stent frame 372 may comprise malleable materials other than shape memory alloys, such as stainless steel. In the latter situation, stent frames 372 will preferably be expanded at the target site by conventional methods, e.g., an expandable balloon at the distal end of a catheter shaft. The tubular member is usually significantly smaller in diameter as compared to the final diameter of the stent in the expanded configuration within channel 264. Slots may be cut into the tubular member via laser cutting methods, photo etching, or other conventional methods to form the separate stent frames 372. For example, these methods include coating the external surface of a tube with photoresist material, optically exposing the etch pattern using a laser beam while translating and rotating the tubular member, and then chemically etching the desired slot pattern of the stent using conventional techniques. A description of this technique can be found in U.S. Pat. No. 5,421,955 to Lau, the complete disclosure of which is incorporated herein by reference. In other methods, laser cutting technology is used in conjunction with computer controlled stages to directly cut a pattern of slots in the wall of the hypodermic tubing to obtain the desired stent geometry. A description of a typical laser cutting method is disclosed in U.S. Pat. No. 5,345,057 to Muller, the complete disclosure of which is incorporated herein by reference.

In an exemplary configuration, the stent frame 372 is formed from a resilient shape memory alloy material that is capable of being deformed by an applied stress, and then recovering to its original unstressed shape. The alloy material will usually exhibit thermoelastic behavior so that the stents will transform to the original unstressed state upon the application of heat (i.e., an Af temperature below body temperature). The stents may also exhibit stress-induced martensite, in which the martensite state is unstable and the prosthesis transforms back to the original state when a constraint has been moved (i.e., when the stent is released from an introducing catheter within a body lumen). The material for the shape memory alloy will be selected according to the characteristics desired of a particular prosthesis. Preferably, the shape memory alloy will comprise a nickel titanium based alloy (i.e., NitinolTM), which may include additional elements which affect the characteristics of the prosthesis, such as the temperature at which the shape transformation occurs. For example, the alloy may incorporate additional metallic elements, such as copper, cobalt, vanadium, chromium, iron, or the like.

It should be noted that the stents 370 described above and shown in FIGS. 17 and 22 are only representative of the lumenal prostheses that may be used with the present invention. The present invention may incorporate a variety of representative conventional stent structures made from metallic tubular materials that are currently marketed as implants for coronary, peripheral, biliary and other vessels including the Palmaz-Schatz™ balloon expandable stent, manufactured by Johnson and Johnson Interventional Systems, Co. and the Memotherm™ stent manufactured by Angiomed, a division of C. R. Bard, Inc. A variety of stent or graft designs can be incorporated into the present invention. Some of these include a coiled structure, such as that described in U.S. Pat. No. 5,476,505 to Limon, an open mesh or weave stent structure formed of helically wound and/or braided strands or filaments of a resilient material, described in U.S. Pat. No. 5,201,757 to Heyn, a filament knitted into a mesh cylinder, described in U.S. Pat. No. 5,234,457 to Andersen, a tubular structure having diamond shaped openings, described in U.S. Pat. No. 5,242,399 to Lau or U.S. Pat. No. 5,382,261 to Palmaz, Z-shaped stents as described in U.S. Pat. No. 5,282,824 to Gianturco, continuous wire stents, such as the one described in U.S. Pat. No. 5,292,331 to Boneau, stents formed of filaments that are wound into spiral or other suitable shapes as described in U.S. Pat. No. 5,314,471 to Fountaine, a continuous helix of zig-zag wire and loops described in U.S. Pat. No. 5,405,377 to Cragg, the full disclosures of which are incorporated herein by reference.

In another aspect, systems and apparatus of the present invention can be used to promote or increase blood flow to, or within, a connective tissue, such as a meniscus, a tendon, a ligament, and the like. For example, in one aspect the present invention can be used to selectively ablate a target tissue, and to create one or more channels or voids within a meniscus, a tendon, or other target tissue, such that blood can flow through the channel(s) or void(s). In one embodiment, the invention may be used to increase the blood supply within a meniscus of the knee. In another aspect, the invention can be used to promote vascularization, e.g., the formation of new blood vessels, in an avascular or sparsely vascularized tissue, such as a meniscus, a tendon, or other target tissue. In yet another aspect, the invention can be used to promote revascularization, e.g., the reestablishment of a blood supply in a target tissue. In one embodiment, increasing the blood flow to a target tissue may involve angiogenesis. According to one aspect of the invention, increasing the blood supply to a target tissue may involve promoting vascularization of the tissue by eliciting a wound healing response by the controlled application of electrical energy to one or more regions of the target tissue.

Figure 24A:
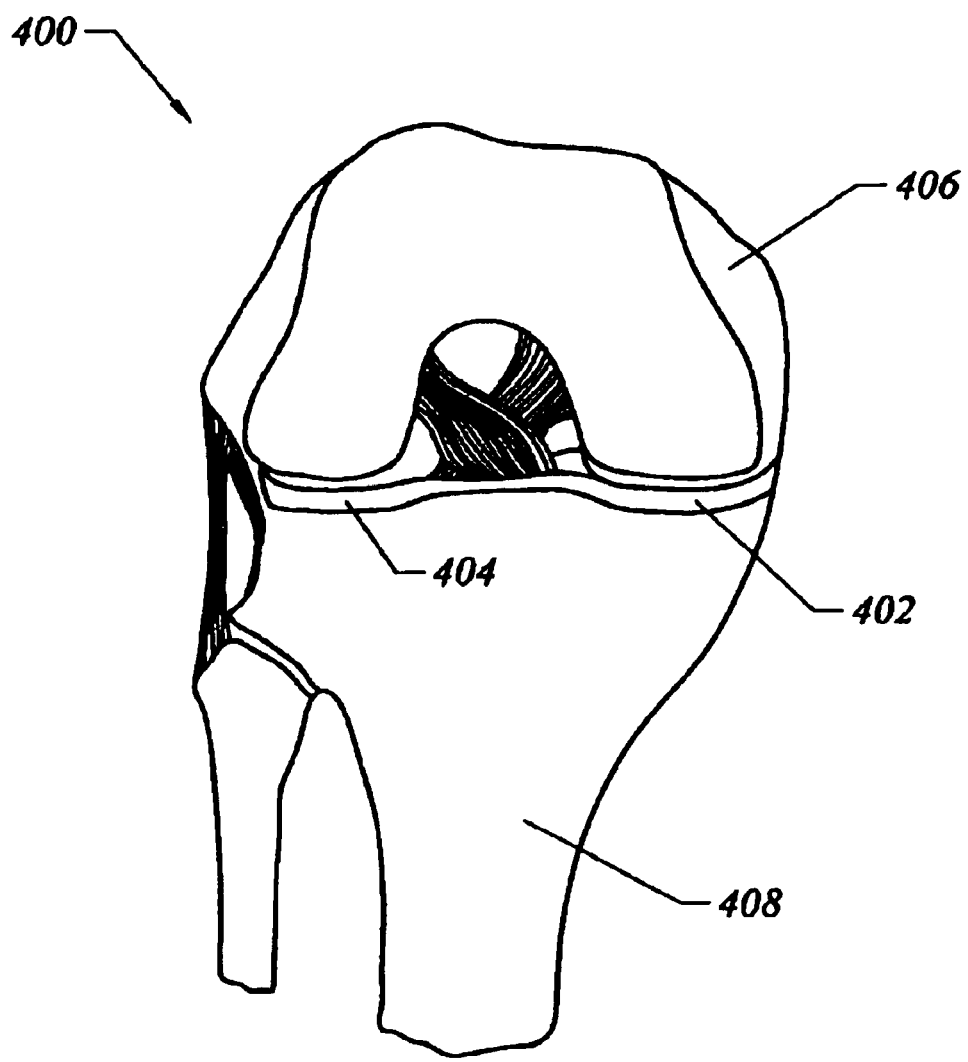
FIG. 24A is an anterior view of a right knee.
Figure 24B:
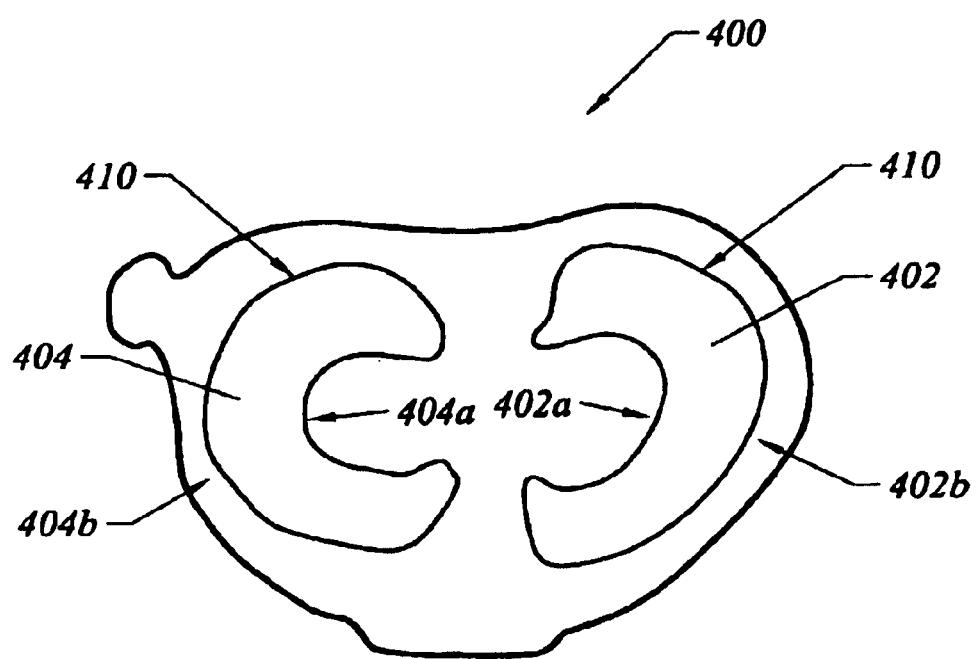
FIG. 24B is a superior view of the interior of the knee showing the medial and lateral meniscus.

FIG. 24A is an anterior view of a right knee 400 in flexion, with the patella omitted to illustrate the medial meniscus 402 and the lateral meniscus 404. Medial meniscus 402 and lateral meniscus 404 are located between the femur 406 and the tibia 408. With reference to FIG. 24B, each of the medial meniscus 402 and the lateral meniscus 404 is a crescent-shaped fibrocartilaginous structure. The majority of the meniscus tissue has a very limited blood supply (this is particularly true for the inner portions or inner aspect 402a, 404a of the meniscus). For that reason, when damaged, the meniscus is unable to undergo the normal healing process that occurs in most other tissues of the body. In addition, with age, the meniscus begins to deteriorate, often developing degenerative tears. Typically, when the meniscus is damaged, the torn pieces begin to move in an abnormal fashion inside the joint. Because the space between the bones of the joint is very small, when the abnormally mobile piece of meniscal tissue (meniscal fragment) moves, it may become caught between the bones of the joint (femur and tibia). When this happens, the knee becomes painful, swollen, and lacks the mobility of a normal knee joint.

Figure 25:
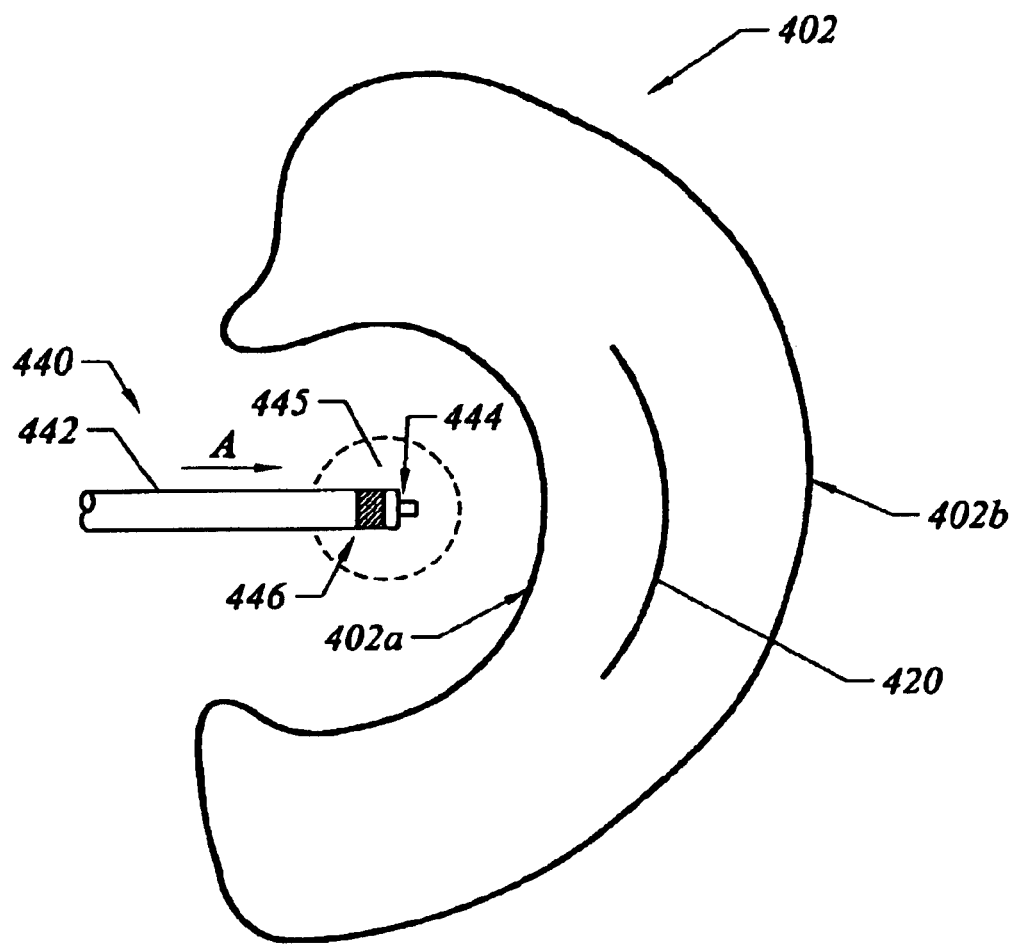
FIG. 25 schematically represents treatment of a meniscus with an electrosurgical probe, according to the present invention.

FIG. 25 schematically represents treatment of a meniscus with an electrosurgical instrument 440, according to one embodiment of the invention. The peripheral portion of the meniscus, termed the menisco-capsular junction 410 (FIG. 24B), has a richer blood supply than the inner portion. Accordingly, in one aspect the present invention provides systems and methods for increasing the blood supply to the inner portion of the meniscus by forming artificial channels or lumens, e.g., one or more channels extending from the menisco-capsular junction 410 to the inner aspect of the meniscus, as will be described in detail hereinbelow (e.g., FIGS. 26A, 26B). An electrosurgical instrument 440 may be introduced into the knee cavity either arthroscopically, or in an open procedure. In an arthroscopic procedure, the knee cavity is typically flooded with electrically conductive fluid 445, while in an open procedure, the fluid 445 may be delivered to the target site (either via instrument 440, or from a separate fluid supply instrument). As shown, instrument 440 is a bipolar probe having a shaft 442, one or more active electrode(s) 444 at the distal end of shaft 442, and a proximally spaced return electrode 446. However, alternative configurations for instrument 440 are also possible under the invention.

Shaft 442 typically has a maximum lateral dimension in the range of from about 3.0 to 1.0 mm, and often less than about 1.0 mm. A direction of advancement of instrument 440, during ablation of meniscus tissue, is indicated by the arrow marked A. Active electrode(s) 444 are positioned adjacent to a target area on the inner aspect 402a of meniscus 402, and a high frequency voltage difference is applied between active electrode(s) 444 and return electrode 446 such that electric current flows through the electrically conductive fluid 445 therebetween. The high frequency voltage is sufficient to convert the electrically conductive fluid 445 between the target tissue and active electrode(s) 444 into an ionized vapor, or plasma (not shown). As a result of the applied voltage difference between active electrode(s) 444 and the target tissue (i.e., the voltage gradient across the plasma layer), charged particles (e.g., electrons) in the plasma are accelerated towards the tissue. At sufficiently high voltages, these charged particles gain sufficient energy to cause dissociation of the molecular bonds of target tissue components. This molecular dissociation is accompanied by the volumetric removal (i.e., ablative sublimation) of tissue, and the production of low molecular weight ablation by-products, e.g., gases, such as oxygen, nitrogen, carbon dioxide, hydrogen and methane.

Depending on the procedure, during application of the high frequency voltage between active electrode 444 and return electrode 446, the surgeon may translate the distal end of shaft 442 relative to the target tissue to form holes, channels, stripes, divots, craters or the like within the tissue. In the representative embodiment, the surgeon axially translates the active electrodes 444 into meniscus tissue, as the tissue is volumetrically removed, to form one or more channels (e.g., channels 424a–n, FIG. 26A) in the meniscus 402. In one embodiment, channels formed in the meniscus according to the procedure described above are substantially cylindrical. Typically, channels 424 have a diameter of less than about 2 mm, and usually less than about 1 mm. As described in detail hereinabove, one advantage of the present invention is the ability to precisely ablate channels or holes within a target tissue without causing necrosis or thermal damage to the underlying or surrounding non-target tissues.

Figure 26A:
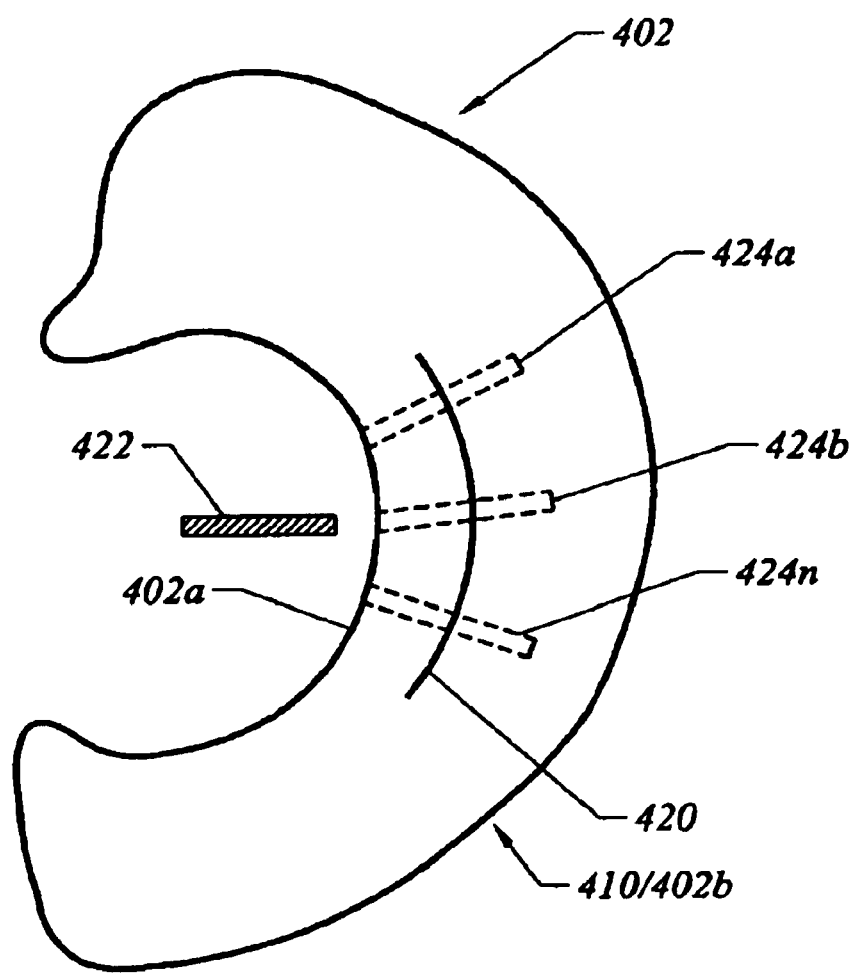
FIG. 26A schematically represents a procedure for treating a meniscus, according to one embodiment of the invention.

With reference to FIG. 26A, the volumetric removal of meniscus tissue is performed in a controlled manner by careful manipulation of instrument 440 to form a channel (e.g., channel 424a) of a selected length and width. Thereafter, instrument 440 is withdrawn from channel 424a, and instrument 440 may be re-positioned with respect to meniscus 402, and instrument 440 again advanced into meniscus 402 for formation of a subsequent channel, e.g., channel 424b. According to one embodiment of the invention, the length, or depth, of a channel 424a–n can be controlled with the aid of a sensing unit (e.g., FIG. 19) adapted for determining a boundary of the target tissue (e.g., meniscus inner or outer aspect, 402a, 402b). In one embodiment, such a sensing unit includes a sensing element, e.g., an ultrasonic transducer located on shaft 442, substantially as described hereinabove with reference to FIGS. 18 and 19.

During the ablation process, the ablation by-products may be aspirated from the surgical site via an aspiration device (not shown). The aspiration device may be integral with instrument 440, or may be on a separate instrument. The aspiration device may include a suction tube or lumen suitably coupled to a vacuum source. In addition, excess electrically conductive fluid, and other fluids (e.g., blood) may be aspirated from the target site to improve the surgeon's view of the surgical site. During ablation of the tissue, the residual heat generated by the current flux lines, will usually be sufficient to coagulate any severed blood vessels at the site. (Typically, the tissue is exposed to a temperature less than about 150° C.) If not, the surgeon may switch power supply 28 (FIG. 1) into the coagulation mode by lowering the voltage to a level below the threshold for fluid vaporization, as discussed above. Thus, the invention can provide simultaneous ablation and hemostasis using a single instrument, resulting in less bleeding and facilitating the procedure.

Procedures which involve forming one or more channels in a meniscus, a tendon, or other poorly vascularized tissue, may be performed alone, or in combination with other arthroscopic procedures, such as a meniscus repair procedure. For example, in prior art meniscus repair procedures, implants are often used for arthroscopic fixation of meniscus lesions. In one conventional procedure, an arrow-like implant is inserted across a lesion to hold the inner and outer portions of the lesion together. The arrow-like implant may comprise a resorbable material that is absorbed into the body after the meniscus has healed. One such implant is called the Meniscus Arrow™ and is commercially available from Bionx Implants, Inc. (Blue Bell, Pa.).

According to one method of the present invention, treatment of the meniscus 402, 404 to improve the flow of blood thereto may be performed in conjunction with various procedures for repairing the meniscus. A longitudinal ("bucket-handle") meniscus lesion 420 is shown in FIG. 26A. Specifically, one or more artificial channels or lumens 424a–n are created from the inner aspect 402a to the outer aspect 402b of the meniscus, as described hereinabove, to allow blood to flow from outer aspect 402b through channels 424a–n to inner aspect 402a. In an alternative embodiment, one or more artificial channels may be formed from outer aspect 402b to inner aspect 402a (e.g., channel 424', FIG. 26B). Three channels are shown in FIG. 26A, however, in practice a larger number of channels may be formed.

With reference to FIGS. 25 and 26A, distal end of instrument 440 is usually advanced distally beyond lesion 420 towards outer aspect 402b, which has a blood supply, to create at least one channel, e.g., channel 424a, of suitable length and width to allow blood to flow into the inner aspect 402a. The resulting increased blood flow within the meniscus, e.g., 402, promotes healing of any tears, ruptures, or other injury, (e.g., tear 420, FIG. 26A). Applicant has found that systems, apparatus, and methods of the present invention can quickly and cleanly create such channels 424 as well as holes, craters, furrows, and the like, in meniscus tissue and other hard connective tissue, using the cold ablation process (known as Coblation™) described herein. A more complete description of methods for forming holes or channels in tissue can be found in U.S. Pat. No. 5,683,366, the complete disclosure of which is incorporated herein by reference for all purposes.

Again with reference to FIG. 26A, after formation of one or more channels, e.g., channels 424a–n, via electrosurgical ablation of the target tissue, an elongate implant 422 may be advanced through each of one or more of channels 424a–n, such that elongate implant 422 extends across lesion 420 to hold the meniscus in place during healing. In this situation, implant 422 serves as a splint, bridging lesion 420. In one aspect of the invention, a proportion of channels 424a–n may be left as voids, i.e., no implant is inserted into the distal portion of channels 42a–n, in order to promote greater blood flow through the vacant channels.

According to another embodiment of the invention, an elongate implant 422 inserted into a channel 424a–n, may comprise a stent to promote patency of such channel(s). Thus, the present invention facilitates the insertion of implants 422 into damaged tissue, and also increases blood flow to the inner aspect 402a of the meniscus 402. The use of stents to maintain patency of a channel formed in a target tissue using an electrosurgical device, is described hereinabove, e.g., with reference to FIGS. 17 & 22.

Figure 26B:
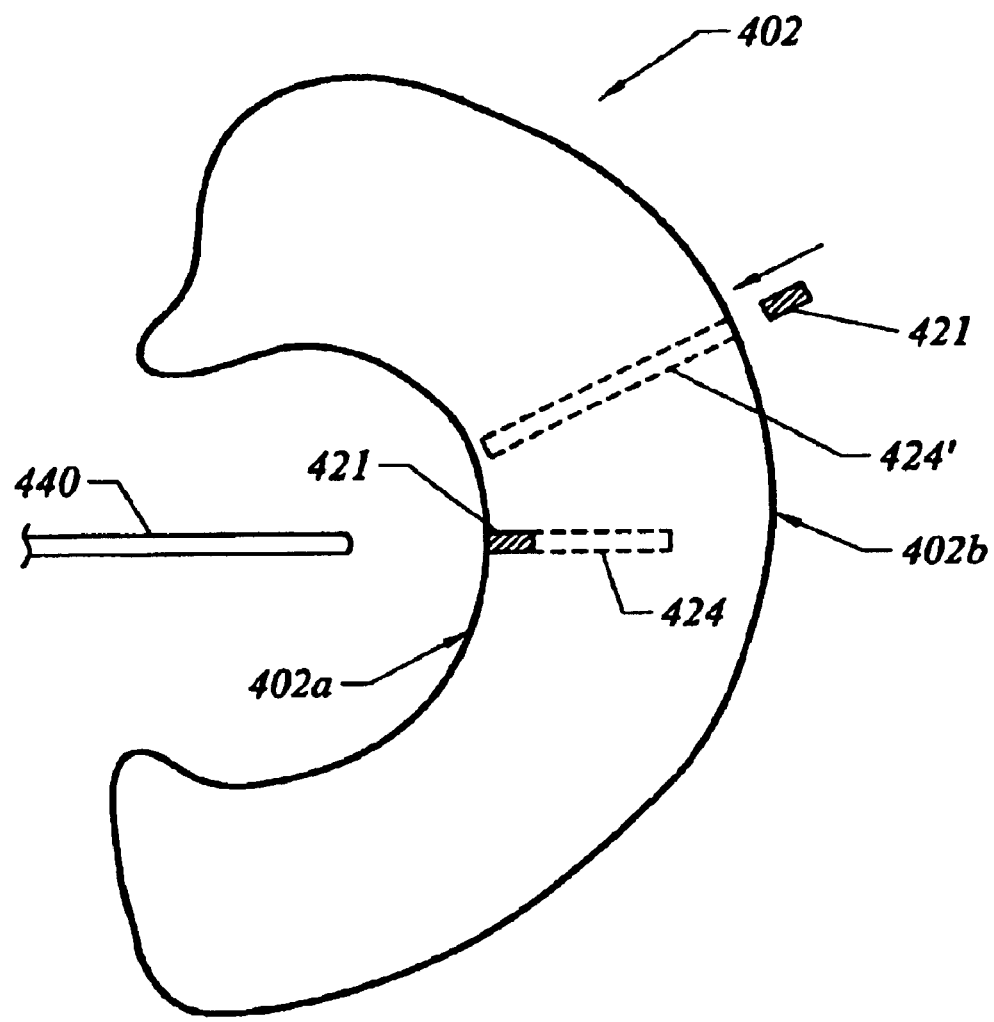
FIG. 26B schematically represents a procedure for treating a meniscus according to another embodiment of the invention.

FIG. 26B schematically represents a procedure for forming one or more channels in a medial meniscus 402 via localized electrosurgical ablation of meniscus tissue, according to another aspect of the invention. As shown, a channel 424 is formed from the inner aspect 402a towards the outer aspect 402b. Such a channel 424 may be formed by axial advancement of the shaft distal end of an electrosurgical instrument 440 towards meniscus 402. As an example, instrument 440 may have a configuration as shown in FIG. 25, including shaft 442, a distal electrode assembly comprising a terminal active electrode, or electrode array, 444 and return electrode 446 located proximal to active electrode 444. Concurrently with the axial advancement, or other manipulation, of instrument 440, a high frequency voltage is applied between active electrode 444 and return electrode 446, to effect the volumetric removal of tissue components, with the concomitant formation of channel 424. Alternatively, or additionally, one or more channels (424')

may be formed from outer aspect 402*b* towards inner aspect 402*a*. Channels 424, 424' may serve as conduits to increase the flow of blood within the meniscus.

Again with reference to FIG. 26B, in one embodiment, a relatively short implant 421 may be inserted in a proximal portion of channel 424, 424' to act as a hemostasis plug, and to prevent any flow of blood from channel 424/424' into the joint cavity. Implant 421 may comprise a collagenous material, for example, substantially as described for hemostasis device 480 (FIG. 21). In one embodiment, patency of one or more channels 424, 424' may be maintained by insertion of a stent therein. In one aspect of the invention, a stent may be used in channel 424 (or channel 424') to maintain patency in a distal portion of channel 424, in conjunction with a hemostasis plug (e.g., implant 421) located in a proximal portion of channel 424.

Although the above canalization procedures are described primarily with reference to forming channels within a meniscus of the knee, systems, apparatus, and methods of the invention are also applicable to the treatment of other joints, and other tissue, such as tendons and ligaments. Thus, apparatus and methods of the present invention can also be used to treat a broad range of musculoskeletal injuries and disorders, such as strains, sprains, tendinitis, fasciitis, arthritis, bursitis and tenosynovitis of various joints, including the shoulder, elbow, knee, ankle, and wrist.

According to one aspect of the invention, a connective tissue having an injury or disorder may be treated using an electrosurgical instrument, e.g., instrument 440, to stimulate or elicit the body's wound healing response in a region of the tissue thus treated. This wound healing response can result in a variety of metabolic, physiological, or anatomical changes, including the stimulation of greater blood flow, collagen growth, alteration of cellular function, or other metabolic events that promote healing and regeneration of injured tissue. In some embodiments, these induced changes may include increased cell metabolism, increased collagen synthesis in fibroblasts, transformation of fibroblasts to myofibroblasts, increased capillary formation with resultant enhanced microcirculation, and/or enhanced clearance of noxious substances associated with the inflammatory response. In other embodiments, the wound healing response can include an increased blood flow to, and vascularization or revascularization of, the treated region, thereby promoting healing and regeneration of injured tissue. In yet other embodiments, the wound healing response can include stimulating the growth of new collagen in the treatment area.

In a specific embodiment, blood flow in a tendon is increased by creating damage to the tendon to invoke a wound healing response. One of the more common afflictions to the tendons is tendinitis, which is an inflammatory condition characterized by pain at tendinous insertions into bone. Common sites of tendonitis include the rotator cuff of the shoulder, insertion of the wrist extensors (tennis elbow), flexors at the elbow, patellar, and popliteal tendons, the iliotibial band at the knee, insertion of the posterior tibial tendon in the leg (shin splints), the wrist (carpal tunnel syndrome), and the Achilles tendon at the heel. Treatment of tendons, according to the invention, increases blood flow therein, e.g., via canalization or by stimulating vascularization thereof, in order to expedite and improve the healing process.

Figure 27:
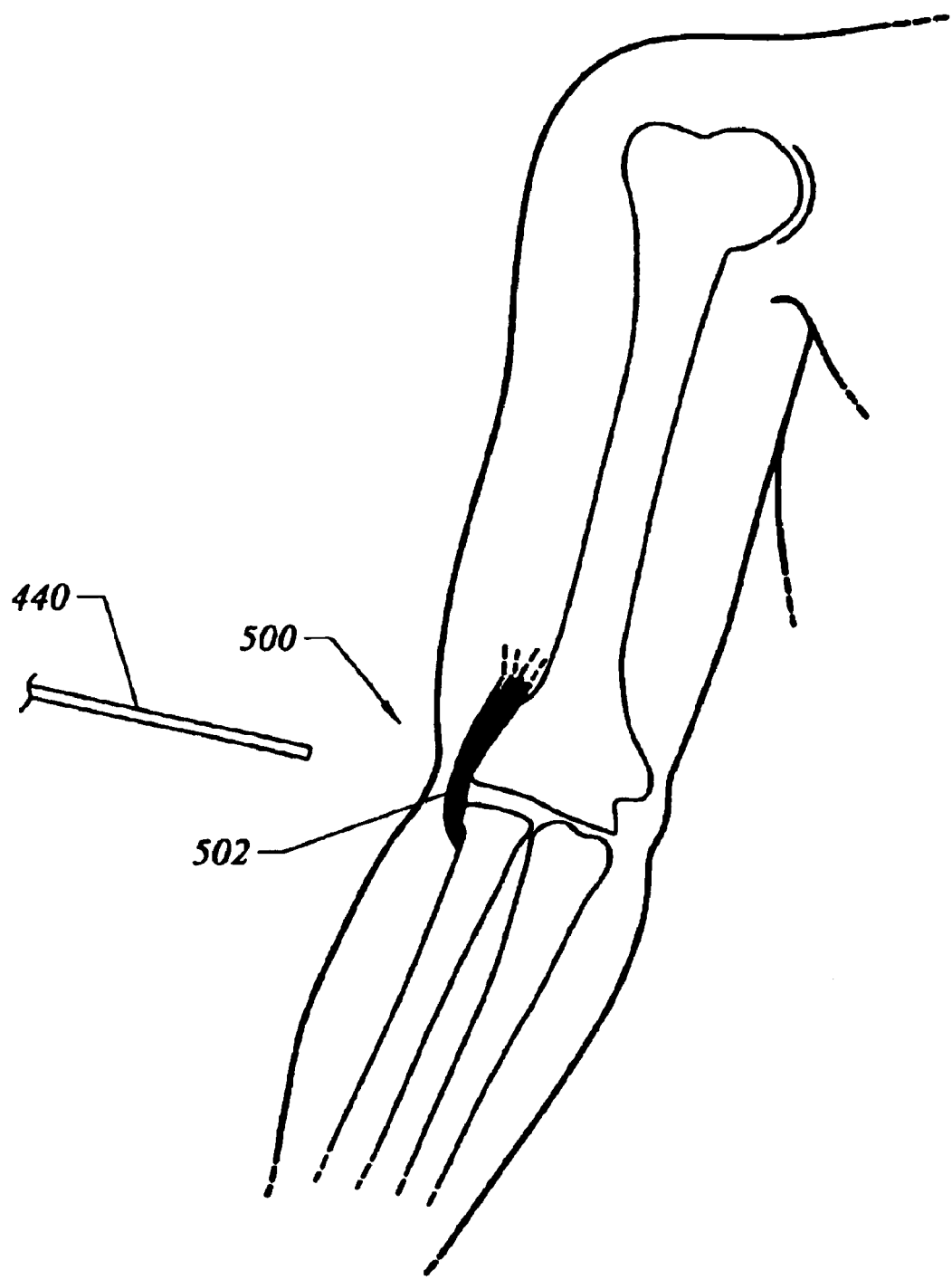
FIG. 27 schematically represents treatment of a tendon using an electrosurgical probe, according to another embodiment of the invention.

The methods of the present invention may be performed alone, or in combination with other open or arthroscopic procedures to treat a tendon. For example, FIG. 27 shows a simplified view of an elbow joint 500. A common disorder of the elbow is known as tennis elbow, or lateral epicondylitis. When a person has tennis elbow, there is often pain and inflammation in the joint due to tendon damage. The damage to the tendon, e.g., tendon 502, typically consists of tiny tears that allow collagen to leak from the injured area and cause inflammation of the tendon. The inflammation can cut off the flow of blood and pinch the radial nerves. Because tendons have much less blood flow as compared with most tissues, e.g., muscles, tendons generally take much longer to heal as compared with most other tissues of the body. If conventional surgical intervention is required to treat a damaged tendon, a patient typically requires about three months to recover.

The present invention, in one aspect, improves and expedites healing, and increases the blood supply to tendon tissue by heating the tendon so as to cause neovascularization. In one embodiment, such heating causes controlled damage to the tendon tissue. In exemplary embodiments, the heating of the tendon is effected by the bipolar or monopolar delivery of RF energy. It should be appreciated, however, that while the methods of the present invention are described primarily with respect to the use of bipolar or monopolar RF energy, that alternative heating methods can be used to treat the tendon tissue. For example, instead of RF heating, the tendons can be treated with resistive heating, or the like.

In some embodiments, methods for promoting healing of a tendon include creating artificial channels, lumens, or craters within the tendon to expose internal portions of the tendon. Such openings facilitate the neovascularization of the inner portions of the tendon. Applicants have found that the creation of damage in tissue, including tendon tissue, elicits a wound healing response and causes an inflammatory cell response so that blood clot(s) fill the opening(s) in the tendon. Accordingly, blood products and the inflammatory process can be the major elicitors of angiogenesis within the tendon. In one embodiment, following electrosurgical treatment of tendon tissue, a vascular scar is formed, which in its early stages is hypoxic, and triggers neovascularization in the tendon. In some embodiments, the tendon is heated and damaged only along the surface. Applicants believe that heat alone, applied in a controlled manner, and typically at a temperature below about 150° C., may be sufficient to trigger vascularization of the tendon.

According to one method of the present invention, treatment of a tendon to stimulate its vascularization may be performed in conjunction with a surgical repair procedure. In one embodiment, one or more artificial voids, channels, lumens, or the like, are created in the tendon to increase blood flow within the tendon. Such channels may be formed either before or after the tendon, e.g., tendon 502, has been otherwise repaired or treated. For the formation of an artificial channel or void in a tendon, according to the instant invention, an electrosurgical instrument, e.g., instrument 440 may be introduced into a patient, e.g., percutaneously, arthroscopically or through an open procedure, such that the distal end of instrument 440 is in at least close proximity to a target site on the tendon to be treated. For example, instrument 440 may be introduced arthroscopically into the joint cavity of the elbow (FIG. 27). Typically, electrosurgical instrument 440 comprises a bipolar probe having a distal electrode assembly including one or more active electrodes 444 and a proximally spaced return electrode 446 (FIG. 25). The active electrode(s) 444 may be in the form of an electrode array, as described hereinabove (e.g., with reference to FIGS. 6–10). In arthroscopic procedures, the joint cavity can be flooded with an electrically conductive fluid, e.g., isotonic saline. In an open procedure, electrically conductive fluid may be delivered to the target site via instrument 440, or from a separate fluid supply device (not shown). In either situation, electrically conductive fluid is provided at the distal end of instrument 440 so as to provide a current flow path between active electrode(s) 444 and return electrode 446.

During a tendon vascularization procedure according to the invention, active electrode(s) 444 are typically positioned adjacent to a target site on the tendon 502, and a high frequency voltage is applied between active electrode(s) 444 and return electrode 446 such that electric current flows through the electrically conductive fluid. The high frequency voltage is sufficient to convert the electrically conductive fluid between the target tissue and the active electrode 444 into an ionized vapor, or plasma (not shown). As a result of the applied voltage difference between active electrode(s) 444 and the tendon 502, charged particles in the plasma are accelerated towards the tendon. At sufficiently high voltage differences, the charged particles gain sufficient energy to cause dissociation of the molecular bonds of the tendon tissue components. The molecular dissociation is accompanied by the volumetric removal (i.e., ablative sublimation) of tendon tissue and the production of low molecular weight ablation by-products.

Figure 28A:
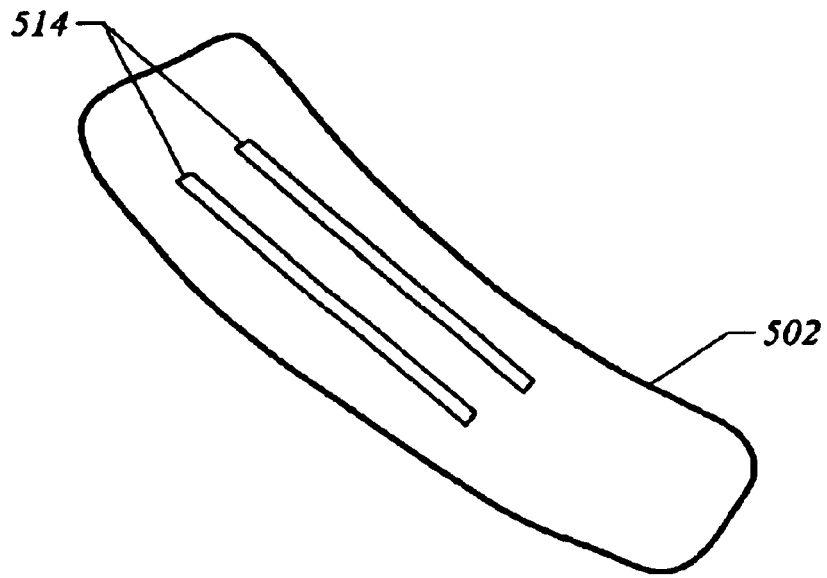
FIG. 28A shows a tendon having a plurality of channels therein.
Figure 28B:
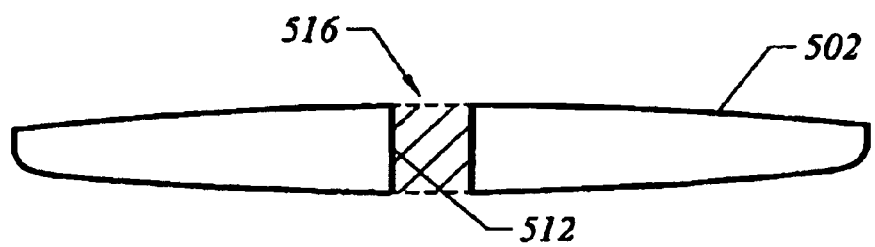
FIG. 28B is a side view of a tendon having a hole therethrough.
Figure 28C:
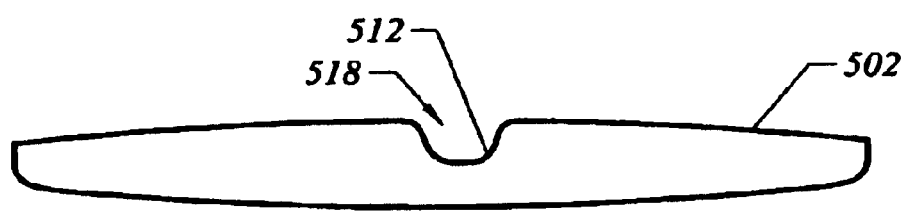
FIG. 28C is a side view of a tendon having a crater in the surface thereof.

With reference to FIG. 28A, an electrosurgical device, (e.g., instrument 440, FIG. 25), can be axially advanced into a tendon or other tissue to form one or more channels 514 therein. Alternatively, or in addition, instrument 440 can be manipulated to form a variety of other openings or voids through a tendon, or on a surface of a tendon. For example, FIG. 28B shows a bore or hole 516 through tendon 502, whereas FIG. 28C illustrates a furrow or crater 518 formed in the surface of tendon 502. During formation of such channels or voids, e.g., 514, 516, 518, internal portions 512 of the tendon are exposed to heat as a result of radio frequency voltage applied between active and return electrodes 444, 446, respectively. Channels or voids 514, 516, 518 created for the purpose of vascularization of tendon 502 will typically have a width or diameter in the range of from about 0.5 mm to about 2.0 mm, usually less than about 1 mm, and most typically about 0.5 mm. Furthermore, opening(s) 514, 516, 518 will typically have a depth in the range of from about 0.5 mm to 4.0 cm, and usually from about 1.0 mm to 2.0 mm. The channels, holes, or craters 514, 516, 518 can be formed randomly along the tendon, at regular intervals along the tendon, or may be strategically located adjacent to a region of the tendon that has undergone repair, for example, repair involving a conventional procedure, such as suturing. It should be appreciated, that the size, depth, number, and spacing of the channel(s), hole(s), and crater(s) may vary depending on the tendon being treated, the condition of the tendon, and the like.

Figure 30A:
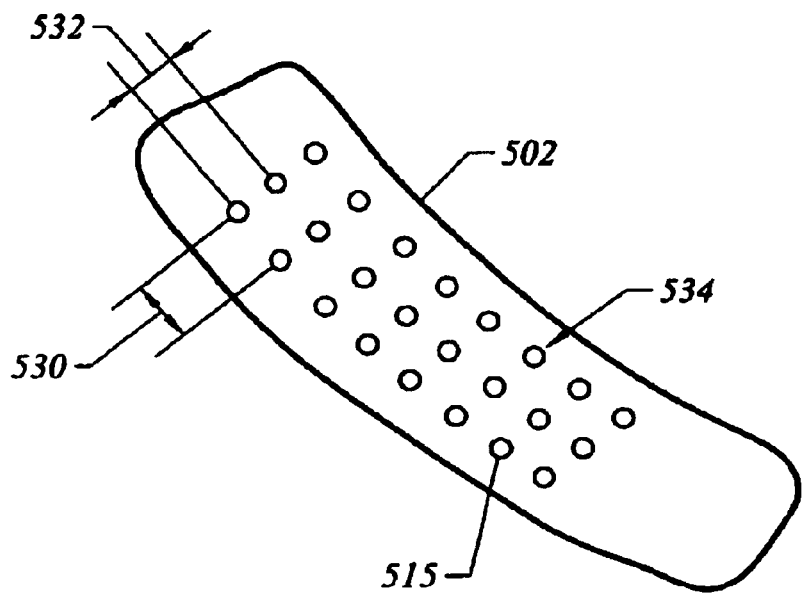
FIGS. 30A–30D represent treatment of tissue by creating a pattern of voids.

One variation of the invention may include treatment of the tissue in regular intervals creating a treatment pattern. For example, referring to FIG. 30A, a number of opening 515 are created in the tissue in a repeated grid-pattern. The grid-pattern may be somewhat curved to accommodate the natural boundaries of the tissue or to accommodate the boundary of the surgical incision(s) created to access the tendon 502. One benefit of creating the openings 515 in such a pattern is that a consistent treatment may be applied rapidly. Moreover, a particular grid-spacing may be selected in combination with the size of the openings created in the tissue. Therefore, selection of a particular grid-spacing or a combination of grid-spacing and opening size give the surgeon the ability to select a specific treatment regimen. Such treatment regimens may provide varying degrees of treatment (e.g., aggressive, moderate, or mild treatment regimens) based upon the needs of the particular patient or the tissue being treated.

The spacing of the grid may vary as required. For example, the spacing may range from 0.5 mm to 10 mm, preferably 5 mm. However, the grid spacing is not limited as such. Obviously, the spacing range will depend upon the area of tissue being treated. It is also noted it is not necessary for the grid spacing to be constant. The grid spacing may increase, decrease, or be variable throughout the treatment area. For example, the grid spacing at the edges of the tissue may differ from the spacing of the openings at the center of the tissue. Moreover, the grid-pattern of the treatment area may be a M×N array where both M and N are greater than or equal to 1. As such, the treatment may be a single row of openings in the tissue or it may be a series of rows placed as appropriate. It is further noted that the grid may be comprised of holes, channels, craters, divots, etc., or a combination thereof.

Figure 30B:
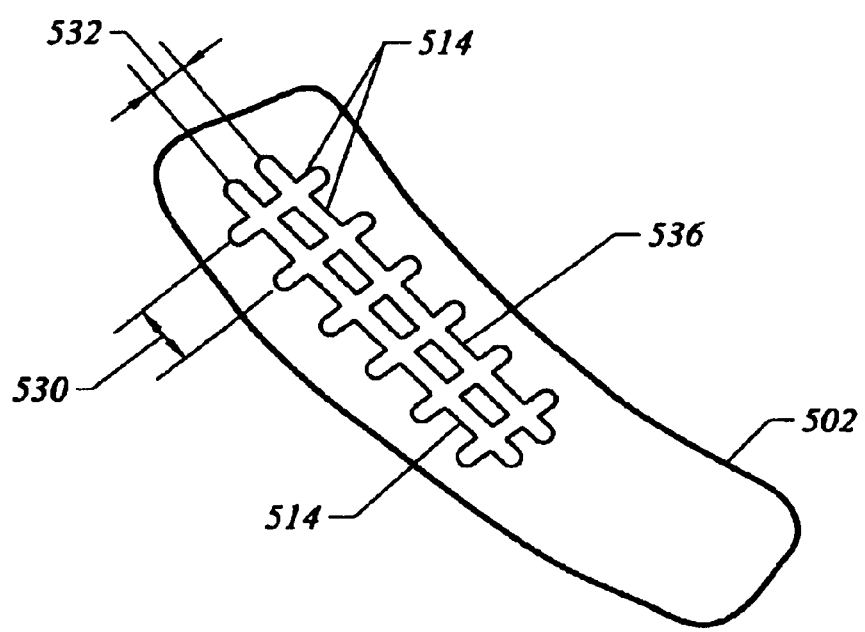
Figure 30C:
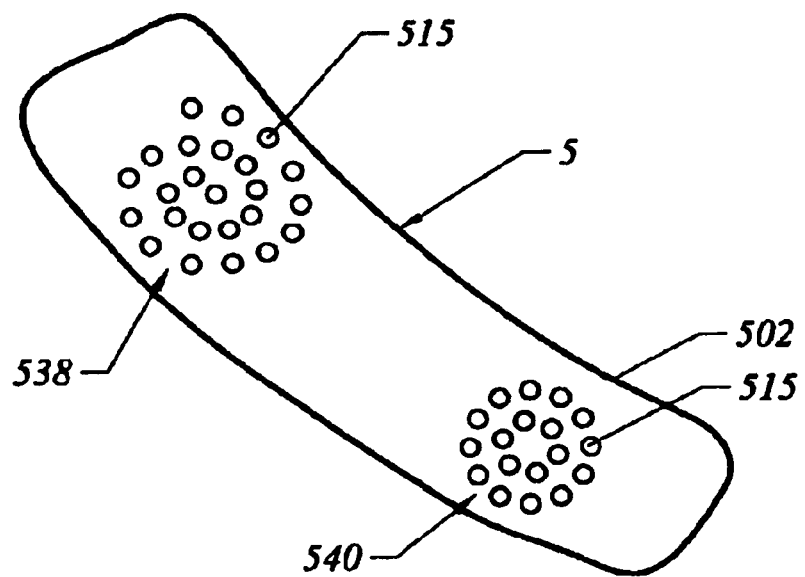
Figure 30D:
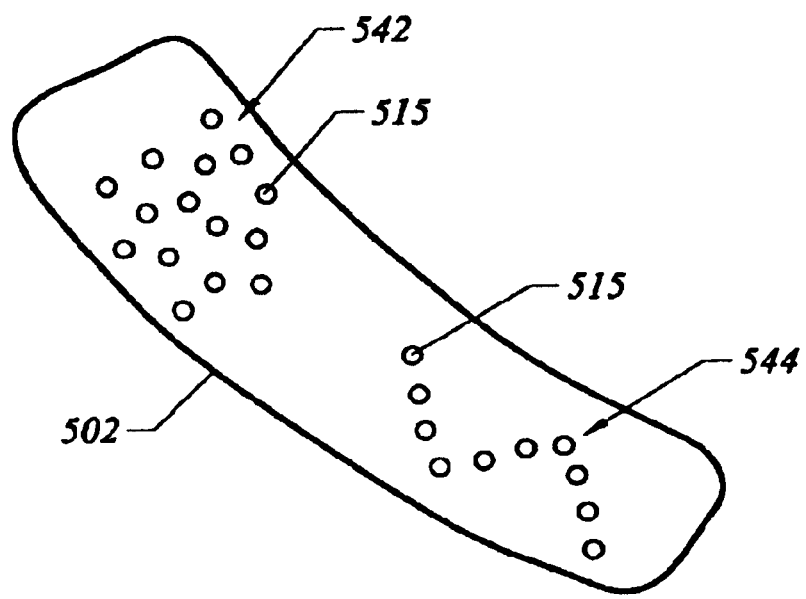

FIG. 30B illustrates a treatment area (e.g., a tendon 502) having a treatment pattern comprising a grid-pattern formed from a series of channels in the tissue. As illustrated, the intersection of the channels may define the spacing or pitch of the grid. It is noted that the invention is not limited to treatment of tissue in a grid-pattern. For example, the treatment may comprise, for example, concentric circular patterns, helical patterns, linear or non-linear patterns, random patterns, or a combination thereof. FIGS. 30C–30D illustrates a helical pattern 538, a circular pattern with concentric circles 540, a random pattern 542, and a non-linear pattern 544. It is appreciated that the patterns may be chosen based upon density of the voids 515, or based upon patterns observed to provide highly beneficial results. Obviously, pertinent aspects of the grid pattern, as described above, may also apply to the other patterns as well.

It is noted that while the invention is discussed in terms of creating the pattern of treatment with RF energy, other modes of creating the pattern of treatment are included within the scope of the invention. For example, the treatment pattern may be made mechanically, ultrasonically, or with any energy-based system.

To create a pattern of treatment the surgeon may be required to simply 'eye-ball' the pattern or use a sterile guide (e.g., a ruler) to estimate where to treat the tissue. However, excessive subjectivity in creating the pattern of treatment may prevent the patient from obtaining the maximum benefit of the procedure. Also, the use of a sterile guide may not be sufficient since some guides (e.g., rulers) may still introduce subjectivity into the procedure.

Figure 31:
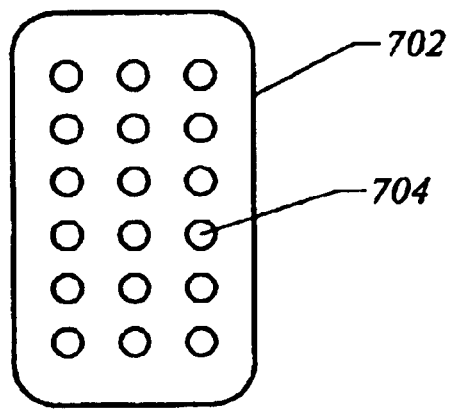
FIGS. 31 and 32A–32B represent template devices for use in assisting the surgeon in creating the pattern of voids.

To increase accuracy and predictability of the procedure's benefits, the invention further includes a template that facilitates placement of the treatment procedure patterns described herein. For example, as illustrated in FIG. 31, a template 702 can function as a map by which the surgeon is able to precisely provide the treatment in a pre-configured pattern. The template 702 illustrated in FIG. 31 contains a 3×6 array of holes 704 through which the surgeon can place the working end of a probe to deliver therapy. First, the surgeon will create an opening to access the tissue. Next, the surgeon will place the template 702 into the opening and adjacent or in contact with the target tissue. Alternatively, the template 702 will be held over the target site while the voids are made in tissue. In such a case, the template 702 may include a handle (not shown) that facilitates holding the template 702 over the target tissue. Next, the surgeon may then use the openings 704 as a guide for a treatment device to provide treatment to the target tissue. Although not illustrated, the template 702 may also have incremental markings along the pattern to denote the spacing of voids in the event a surgeon desires to create an opening in a select number of openings.

The template 702 is not limited to the illustrated pattern. Instead, the template 702 may contain a pattern to provide any of the treatment grid-patterns described herein. Furthermore, a surgeon may be provided with a number of templates 702 each having a distinct pattern or each comprising templates having a range of sizes. The assortment of templates provides the surgeon with a range of treatment options. Thus, the surgeon may select the option that best fits the type of tissue being treated and/or the needs of the patient. The openings 704 of the template 702 may also be configured to have a shoulder that mates with a shoulder of a treatment device. Such a feature will limit advancement of a treatment device to a pre-set depth when making each opening in the tissue. The invention also contemplates using the template as a guide for marking locations where voids are to be created and removing the template prior to creation of the voids.

In one variation of the invention, the template 702 is coated or fabricated from a material that is non-reactive to RF energy (e.g., a polymeric material.) The template 702 may also be configured such that it is clear (e.g., a polycarbonate material), thereby permitting visualization of the tissue being treated. Moreover, the template 702 may also have such features to further aid the procedure. For example, it may be desirable for the template 702 to be designed such that it does not contribute to the unwanted heating of the target tissue. For example, the following is a list of non-exhaustive variations of the template: the side of the template 702 immediately adjacent to the target tissue may be configured such that the template 702 is offset from the tissue to allow sufficient ventilation so that the heat may be vented from the tissue area; the tissue treatment side of the template 702 may have a coating that prevents heat generated by the ablation process from being reflected back to the target site; the template 702 may comprise a mesh or other porous structure that allows the venting of heat from the ablation site; the tissue treatment side of the template 702 may have openings 704 that are in fluid communication, thereby allowing circulation of conductive fluids between the openings; the template 702 may have fluid delivery channels to permit the continual supply of conductive fluid to the tissue treatment site; the template 702 may have fluid evacuation channels to permit the removal or circulation of conductive fluid at the treatment site; etc.

Figure 32A:
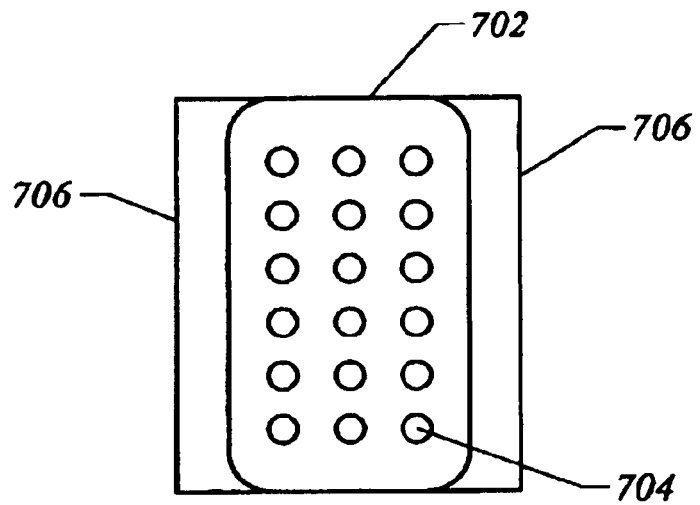
Figure 32B:
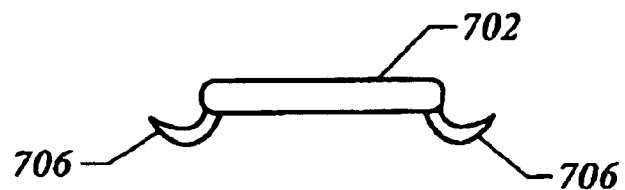

As illustrated in FIGS. 32A and 32B, the template 702 may also be configured to function as a tissue retractor. During the procedure, a surgeon may require an assistant to retract the skin and other tissue so that the target tissue may be accessed and treated. After the surgeon creates an incision, the template 702 may be used in lieu of conventional retractors of forceps to create an open space. Alternatively, the template 702 may be inserted at the target site after conventional retractors or forceps create the initial space. As shown in FIGS. 32A and 32B, this variation of the template 702 will have one or more portions that functions as a tissue retractor (e.g., 706.) As shown in FIG. 32B, which is a bottom view of the template 702 of FIG. 32A, the tissue retractor portion may protrude from the template 702. Alternatively, or in addition, the sides of the template could be adapted to separate tissue. It is understood that a variety of modes may be incorporated with the template 702 to serve as the tissue retracting portion and the variations shown are for illustrative purposes.

It is contemplated that templates of the present invention may be provided separately from or in a kit with devices capable of performing the procedure.

Figure 33:
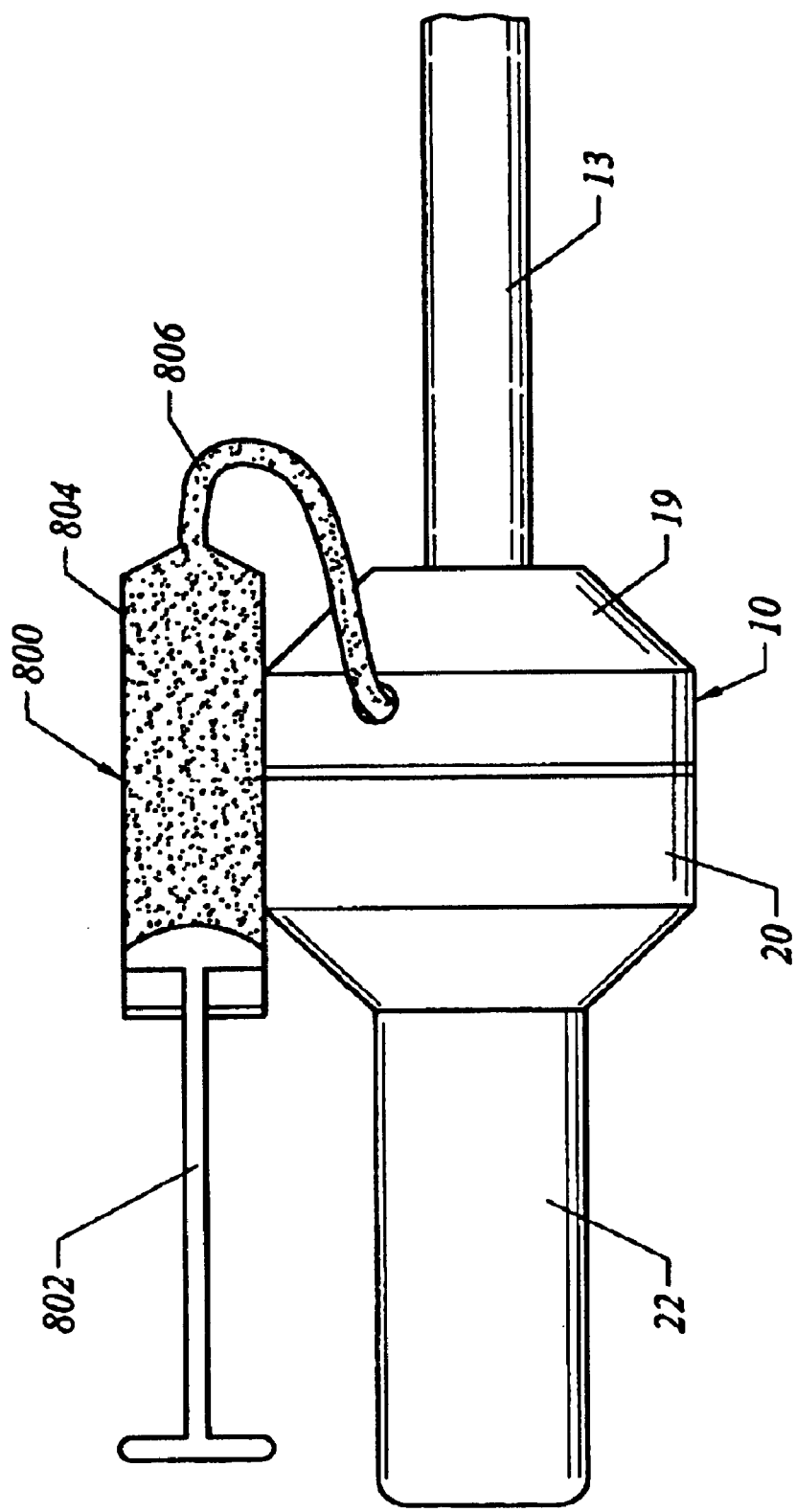
FIG. 33 represents a self-contained fluid supply unit attached to an electrosurgical device.

FIG. 33 illustrates another variation of the device comprising a probe 10, handle 22, and connector 20. In this variation, the probe 10 is provided with a self-contained fluid supply 800. The self-contained fluid supply 800 preferably has a fluid-driving member 802 (e.g., a plunger assembly, a siphon, etc.) for moving the fluid from the fluid supply 800 through the probe 10 to the target site. The self-contained fluid supply 800 also comprises a reservoir 804, and a connector lumen 806. The fluid driving member 802 may be moveably located in the fluid reservoir 804 to drive fluid out of the fluid supply 800. The connector lumen 806 may fluidly couple the fluid supply 800 to the probe 10 (preferably to a fluid delivery lumen within the probe.) The connector lumen 806 may be fluidly coupled to the fluid delivery lumen of the device via the probe instrument shaft 13, the probe connector 19, the handle connector 20, or handle 22.

The fluid supply 800 may be adapted to be incorporated into existing probes that previously required a discrete fluid supply source (e.g., an IV unit with sterile saline.) Although FIG. 33 illustrates the fluid supply 800 as being external to the device, the fluid supply 800 may be incorporated interior to the body of the device. Therefore, instead of being refillable or connectable to discrete sources of conductive fluid, the probes may be pre-loaded with sufficient doses of conductive fluid when provided to a surgeon. Such a configuration allows a more self-contained, disposable treatment probe. Alternatively, the fluid supply 800 may have a port allowing for re-filling of the conductive fluid.

It may be preferable that the device is configured such that the surgeon is able to manipulate the device and actuate the self-contained fluid supply 800 using a single hand. It is further noted that either the probe or the fluid supply 800 may be gated such that fluid does not leak or accidentally discharged from the device.

During the volumetric removal of tendon tissue, ablation by-products, together with any excess electrically conductive fluid, and other fluids (e.g., synovial fluid, blood), may be aspirated from the surgical site, substantially as described hereinabove. During ablation of the tissue, the residual heat generated by the current flux lines, will usually be sufficient to coagulate any severed blood vessels at the site. If not, the surgeon may switch the power supply 28 (FIG. 1) into the coagulation mode, as discussed above, to effect hemostasis of the treated tissue.

Figure 29:
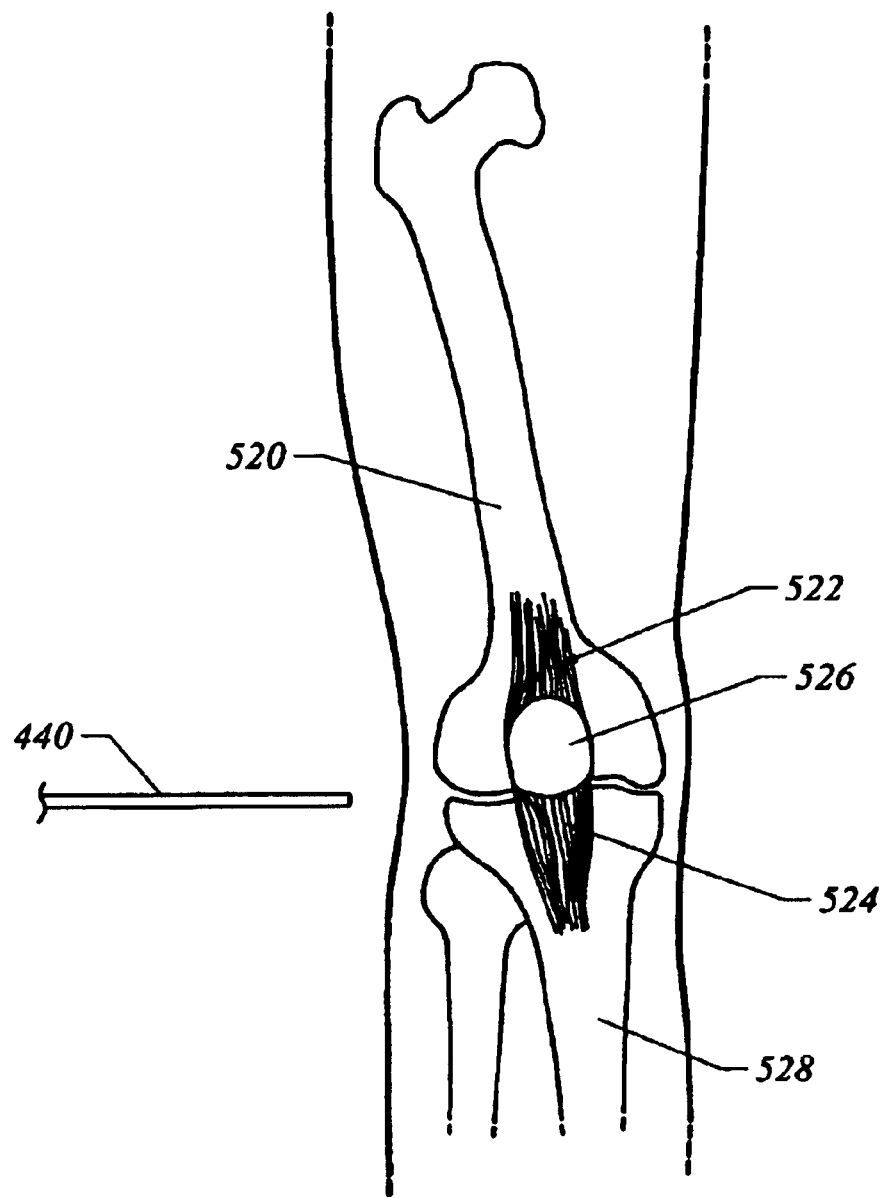
FIG. 29 schematically represents electrosurgical treatment of a patellar tendon or patellar ligament, according to another embodiment of the invention.

As a further example, systems, apparatus, and methods of the present invention may be used to improve the blood supply and increase the vascularity of the patellar tendon and/or the patellar ligament. FIG. 29 is an anterior view of the right leg showing the patellar tendon 522 and the patellar ligament 524 in relation to the patella 526. As described hereinabove, the instant invention may be used for vascularization of tissue, such as a tendon, or a ligament, in conjunction with other surgical procedures. When the patellar tendon or patellar ligament sustain a tear or rupture due to injury, the patella 526 may lose its anchoring support to the tibia 528. Such an injury requires surgical intervention. For example, an open procedure may be performed to reattach the patella to the tibia 528, to repair the patellar tendon, or to perform other repairs. After the patella and/or patellar tendon has been repaired, the surgeon can use the systems, apparatus, and methods of the present invention to increase the vascularity of the patellar tendon and/or the patellar ligament. For example, after the patellar tendon has been repaired, an electrosurgical instrument 440 can be positioned adjacent to the patellar tendon 522. An electrically conductive fluid may be delivered to the target site via instrument 440, or from a separate fluid supply device (not shown), to provide a current flow path between active electrode(s) 444 and return electrode 446. A high frequency voltage difference is applied between active electrode(s) 444 and return electrode 446 such that electric current flows through the electrically conductive fluid. As described above, the high frequency voltage is sufficient to convert the electrically conductive fluid between the target tissue and active electrode 444 into an ionized vapor, or plasma (not shown) so as to cause localized molecular dissociation of the tendon tissue. The molecular dissociation is accompanied by the volumetric removal (i.e., ablative sublimation) of the tendon tissue, and the production of low molecular weight ablation by-products. In one embodiment, the surgeon advances a distal surface of the active electrode(s) 444 into the tendon tissue to form openings such as holes, channels, stripes, divots, craters, or the like, to promote blood flow within the tendon. In one embodiment, treatment of a tissue to improve blood flow thereto is performed in conjunction with a surgical repair, of the tissue, and thereafter one or more channels or voids may be placed adjacent to the surgical repair site so as to promote blood flow to the repair site, thereby stimulating the healing process.

It should be appreciated that the size and shape of the electrosurgical systems and devices used to canalize or vascularize the tendon will vary depending on the type of procedure (i.e., creation of holes, channels, or craters) and the position of the tendon to be accessed. If the tendon is treated endoscopically or arthroscopically through a small joint, a smaller wand-type electrosurgical probe will typically be used to perform the vascularization. Alternatively, if the tendon is treated through an open procedure, a larger probe may be used. Although certain of the treatments for increasing blood flow within a tissue are described hereinabove primarily with respect to a tendon of the elbow, apparatus and methods of the invention are also applicable to the treatment of other joints, and to target tissue other than tendons.

While the exemplary embodiments of the present invention have been described in detail, by way of example and for clarity of understanding, a variety of changes, adaptations, and modifications will be apparent to those of skill in the art. Therefore, the scope of the present invention is limited solely by the appended claims.

What is claimed is:

1. A method of inducing a controlled inflammatory response in tissue, the method comprising:
   selecting a target tissue from an area of soft tissue;
   applying energy to the target tissue; and
   forming at least one pattern of voids by repeating the applying act.

2. The method of claim 1 comprising:
   selecting a target tissue from an area of soft tissue;
   positioning an active electrode in at least close proximity to the target tissue;
   removing a void in the tissue by applying a high frequency voltage to the active electrode, the high frequency voltage being sufficient to volumetrically remove a portion of the target tissue; and
   forming at least one pattern of voids by repeating the positioning and applying acts.

3. The method of claim 2, wherein selecting the target tissue comprises selecting target tissue from a group consisting of a tendon, a ligament, and a meniscus.

4. The method of claim 2, wherein the pattern comprises a pattern selected from a group consisting of a grid, a circle, at least two circles, at least two concentric circles, a helical pattern, a linear pattern, a non-linear pattern, a random pattern, and a combination thereof.

5. The method of claim 4, wherein a spacing between voids ranges between 0.5 mm and 10 mm.

6. The method of claim 4, wherein a spacing between voids is constant.

7. The method of claim 4, wherein a spacing between voids varies.

8. The method of claim 4, further comprising placing a template adjacent to the target tissue prior to the positioning step, wherein the template comprises a plurality of holes arranged in a layout similar to the pattern.

9. The method of claim 8, wherein the forming step comprises using the template as a guide for positioning the active electrode.

10. The method of claim 8 wherein the template further serves to separate tissue adjacent to the target tissue.

11. The method of claim 2, wherein the void has a lateral dimension in the range of from about 0.5 mm to about 2.0 mm.

12. The method of claim 2, wherein the void has a depth in the range of from about 0.5 mm to about 4.0 cm.

13. The method of claim 2, wherein the void comprises an opening in tissue selected from the group consisting of a channel, a hole, a furrow, a crater, a divot, and a combination thereof.

14. The method of claim 13, wherein the act of removing the void comprises applying the high frequency voltage between the active electrode and a return electrode.

15. The method of claim 13, wherein the return electrode is located on an external surface of a patient's body.

16. The method of claim 13, wherein the return electrode and the active electrode are both located on an electrosurgical probe.

17. The method of claim 13, further comprising placing an electrically conductive fluid between the active electrode and the return electrode, the electrically conductive fluid providing a current flow path between the active electrode and the return electrode.

18. The method of claim 16, wherein the electrically conductive fluid comprises isotonic saline.

19. The method of claim 2, wherein the active electrode comprises a single electrode adjacent to a distal end of an electrosurgical probe.

20. The method of claim 19, wherein the active electrode comprises an electrode array comprising a plurality of electrically isolated active electrodes, and wherein said applying step comprises applying the high frequency voltage to the electrode array.

21. The method of claim 2, further comprising providing an electrically conductive fluid between the active electrode and the target tissue.

22. The method of claim 2, further comprising introducing at least a distal end of an electrosurgical probe into a patient's knee, shoulder, or elbow; wherein said positioning step comprises positioning the distal end of the probe in at least close proximity to the tendon within the knee, the shoulder, or the elbow.

23. A method of treating soft tissue comprising:
   selecting a target tissue from the group consisting of a tendon, ligament, and meniscus;

applying energy to the target tissue; and forming at least one pattern of voids by repeating the applying act.

24. A method of treating soft tissue comprising inducing a healing response in said tissue by creating at least one void in said tissue with an elongate apparatus, said apparatus comprising at least one active electrode arranged on a distal end of said apparatus, said electrode being electrically connected with a high frequency voltage source, wherein said at least one void is created by positioning said active electrode in at least close proximity to the tissue and activating said electrode with a selected voltage.

* * * * *